United States Patent
Black et al.

(10) Patent No.: US 11,937,892 B2
(45) Date of Patent: Mar. 26, 2024

(54) VARIABLE JAW CLOSURE OF A ROBOTIC SURGICAL SYSTEM

(71) Applicant: Cilag GmbH International, Zug (CH)

(72) Inventors: Brian D. Black, Loveland, OH (US); Charles J. Scheib, Loveland, OH (US); Matthew T. Stone, Mason, OH (US); Mark D. Overmyer, Cincinnati, OH (US); Christopher A. Denzinger, Cincinnati, OH (US); Andrew T. Beckman, Cincinnati, OH (US); Neil T. Markwardt, Redwood City, CA (US)

(73) Assignee: Cilag GmbH International, Zug (CH)

( * ) Notice: Subject to any disclaimer, the term of this patent is extended or adjusted under 35 U.S.C. 154(b) by 190 days.

(21) Appl. No.: 17/245,332

(22) Filed: Apr. 30, 2021

(65) Prior Publication Data

US 2022/0346897 A1 Nov. 3, 2022

(51) Int. Cl.
*A61B 17/068* (2006.01)
*A61B 17/28* (2006.01)
(Continued)

(52) U.S. Cl.
CPC .............. *A61B 34/37* (2016.02); *A61B 34/70* (2016.02); *B25J 5/00* (2013.01); *B25J 9/102* (2013.01);
(Continued)

(58) Field of Classification Search
CPC . A61B 17/29; A61B 17/068; A61B 17/22031; A61B 17/3201; A61B 2017/2932; A61B 2017/2933; A61B 2017/2934; A61B 2017/2936; A61B 2017/2937; A61B 2017/2913; A61B 2017/2915; A61B 2017/2916; A61B 2017/2917; A61B 2017/22035;
(Continued)

(56) References Cited

U.S. PATENT DOCUMENTS 7,404,508 B2 7/2008 Smith et al.
7,434,715 B2 10/2008 Shelton, IV et al.
(Continued)

OTHER PUBLICATIONS

U.S. Appl. No. 17/245,100.
(Continued)

*Primary Examiner* — Katherine M Rodjom
*Assistant Examiner* — Lindsey R. Rivers
(74) *Attorney, Agent, or Firm* — Frost Brown Todd LLP

(57) ABSTRACT

A surgical instrument includes a drive housing, a spline, a carriage, an elongate shaft assembly, an end effector, and an activating mechanism. The at least one spline includes a drive gear rotatable with the spline. The elongate shaft assembly extends from the carriage. The activating mechanism includes a barrel cam extending along a rotational axis and having a first cam profile radially extending about the rotational axis. The barrel cam is operatively coupled to the drive gear such that rotation of the drive gear is configured to actuate the activating mechanism to move at least a portion of the end effector. The first cam profile defines a plurality of slopes relative to the rotational axis such that the first cam profile is configured to drive movement of the end effector or the elongate shaft assembly at different rates according to the plurality of slopes.

20 Claims, 28 Drawing Sheets

(51) Int. Cl.
    *A61B 17/29*     (2006.01)
    *A61B 17/3201*     (2006.01)
    *A61B 34/00*     (2016.01)
    *A61B 34/37*     (2016.01)
    *B25J 5/00*     (2006.01)
    *B25J 9/10*     (2006.01)
    *A61B 17/00*     (2006.01)
    *A61B 17/072*     (2006.01)

(52) U.S. Cl.
    CPC ............ *B25J 9/109* (2013.01); *A61B 17/068* (2013.01); *A61B 17/282* (2013.01); *A61B 2017/2936* (2013.01); *A61B 17/3201* (2013.01)

(58) Field of Classification Search
    CPC ........ A61B 2017/0488; A61B 18/1442; A61B 18/1445; A61B 18/1447; A61B 10/06; A61B 34/70
    See application file for complete search history.

(56) References Cited

U.S. PATENT DOCUMENTS

| | | | |
|---|---|---|---|
| 7,721,930 | B2 | 5/2010 | McKenna et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 8,663,220 | B2 | 3/2014 | Wiener et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,949,785 | B2 | 4/2018 | Price et al. |
| 10,092,292 | B2 | 10/2018 | Boudreaux et al. |
| 10,349,939 | B2 | 7/2019 | Shelton, IV et al. |
| 2006/0079874 | A1 | 4/2006 | Faller et al. |
| 2007/0191713 | A1 | 8/2007 | Eichmann et al. |
| 2008/0200940 | A1 | 8/2008 | Eichmann et al. |
| 2011/0093007 | A1* | 4/2011 | Abbott ............... A61B 17/0644 606/213 |
| 2015/0083772 | A1* | 3/2015 | Miller .................. A61B 17/068 227/175.1 |
| 2015/0327850 | A1* | 11/2015 | Kostrzewski .... A61B 17/07207 74/57 |
| 2017/0340325 | A1* | 11/2017 | Baril .................... A61B 17/105 |
| 2019/0231330 | A1* | 8/2019 | Xu ......................... A61B 17/29 |
| 2021/0393340 | A1 | 12/2021 | Beckman et al. |

OTHER PUBLICATIONS

U.S. Appl. No. 17/245,332.
U.S. Appl. No. 17/245,340.
U.S. Appl. No. 17/245,351.
U.S. Appl. No. 17/022,520, entitled "Method of Applying Buttress to End Effector of Surgical Stapler," filed Sep. 19, 2020.
U.S. Appl. No. 17/077,067, entitled "Surgical Instrument and Carrier KART Supporting Ultrasonic Transducer," filed Oct. 22, 2020.
U.S. Appl. No. 17/077,086, entitled "Carrier KART and Jaw Closure of an Ultrasonic Surgical Instrument," filed Oct. 22, 2020.
U.S. Appl. No. 17/076,956, entitled "Surgical Instrument with an Articulatable Shaft Assembly and Dual End Effector Role," filed Oct. 22, 2020.
U.S. Appl. No. 17/076,959, entitled "Ultrasonic Surgical Instrument with a Distally Grounded Acoustic Wave," filed Oct. 22, 2020.
U.S. Appl. No. 17/077,098, entitled "Ultrasonic Surgical Instrument with a Multiplanar Articulation Joint," filed Oct. 22, 2020.
U.S. Appl. No. 17/077,110, entitled "Ultrasonic Surgical Instrument with a Mid-Shaft Closure System and Related Methods," filed Oct. 22, 2020.
U.S. Appl. No. 17/077,130, entitled "Surgical Instrument with Clamping Sensor Feedback and Related Methods," filed Oct. 22, 2020.
U.S. Appl. No. 17/077,136, entitled "Surgical Instrument with Non-Clamping Sensor Feedback and Related Methods," filed Oct. 22, 2020.
U.S. Appl. No. 17/077,139, entitled "Ultrasonic Surgical Instrument with a Fixed Transducer Grounding," filed Oct. 22, 2020.
U.S. Appl. No. 17/077,146, entitled "Ultrasonic Surgical Instrument with a Shaft Assembly and Elongated Waveguide Support Arrangement," filed Oct. 22, 2020.
U.S. Appl. No. 17/077,152, entitled "Damping Rings for an Ultrasonic Surgical Instrument," filed Oct. 22, 2020.
U.S. Appl. No. 17/077,250, entitled "Ultrasonic Surgical Instrument with a Carrier KART and Reusable Stage," filed Oct. 22, 2020.
U.S. Appl. No. 17/077,373, entitled "Surgical Instrument with a Carrier KART and Various Communication Cable Arrangements," filed Oct. 22, 2020.
U.S. Appl. No. 17/245,100, entitled "Translatable Barrel Cam of a Robotic Surgical System," filed Apr. 30, 2021.
U.S. Appl. No. 17/245,340, entitled "Robotic Surgical System with an Articulation Lockout," filed Apr. 30, 2021.
U.S. Appl. No. 17/245,351, entitled "Multi-Zone Jaw Closure of a Robotic Surgical System," filed Apr. 30, 2021.

\* cited by examiner

VARIABLE JAW CLOSURE OF A ROBOTIC SURGICAL SYSTEM

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. patents is incorporated by reference herein in its entirety.

Additional examples of such surgical instruments include an ultrasonic surgical instrument with end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned; U.S. Pub. No. 2007/0191713, entitled "Ultrasonic Device for Cutting and Coagulating," published Aug. 16, 2007, now abandoned, U.S. Pub. No. 2008/0200940, entitled "Ultrasonic Device for Cutting and Coagulating," published Aug. 21, 2008, now abandoned, U.S. Pat. No. 9,949,785, entitled "Ultrasonic Surgical Instrument with Electrosurgical Feature," issued Apr. 24, 2018, and U.S. Pat. No. 8,663,220, entitled "Ultrasonic Surgical Instruments," issued Mar. 4, 2014. The disclosure of each of the above-cited U.S. Patent Publications and U.S. patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
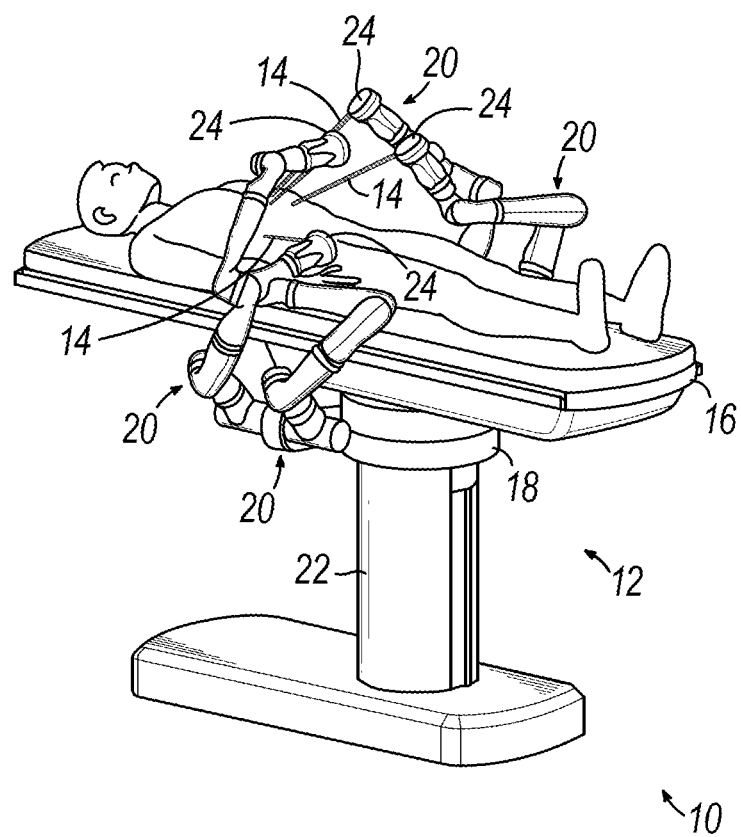
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "longitudinal," "inner," "outer," and "upper," also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Exemplary Robotically-Enabled Medical System

FIG. 1 shows an exemplary robotically-enabled medical system, including a first example of a table-based robotic system (10). Table-based robotic system (10) of the present example includes a table system (12) operatively connected to a surgical instrument (14) for a diagnostic and/or therapeutic procedure in the course of treating a patient. Such procedures may include, but are not limited, to bronchoscopy, ureteroscopy, a vascular procedure, and a laparoscopic procedure. To this end, surgical instrument (14) is configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
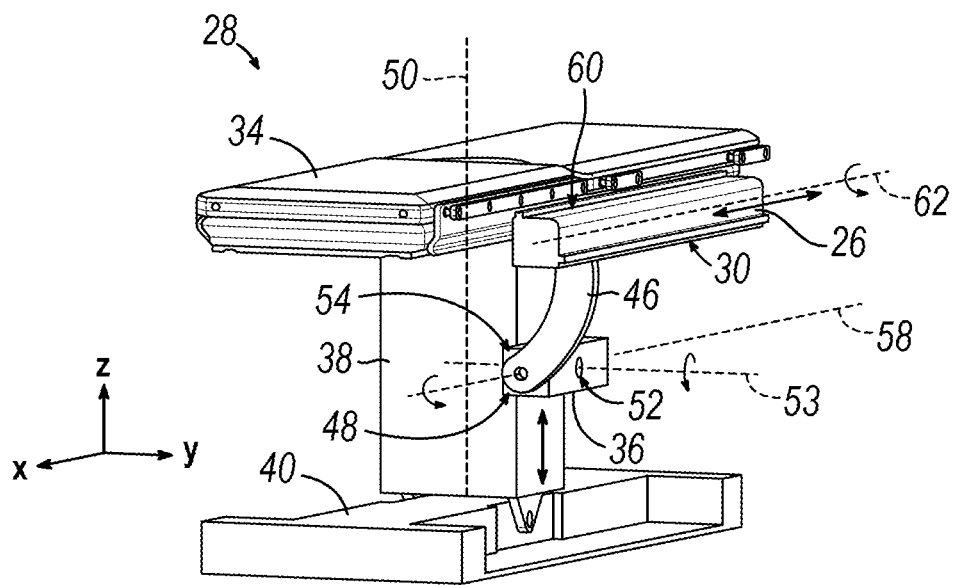
FIG. 2 depicts a perspective view of a second example of a table-based robotic system.
Figure 3:
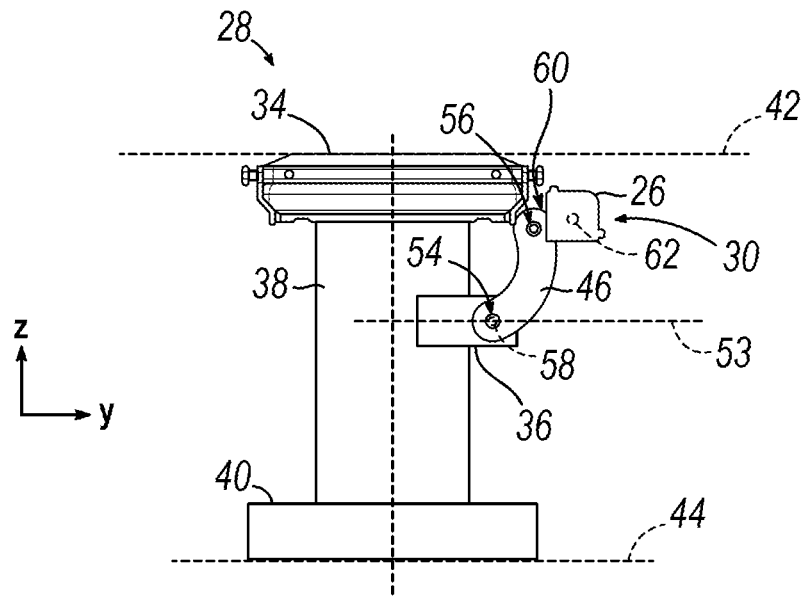
FIG. 3 depicts an end elevational view of the table-based robotic system of FIG. 2.
Figure 4:
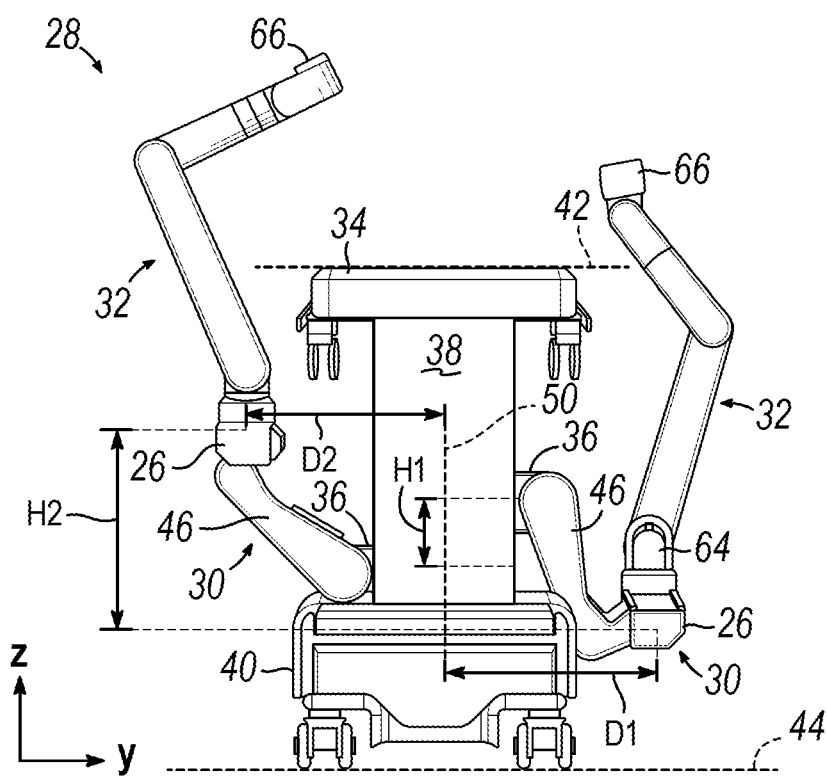
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as surgical instrument (14) (see FIG. 6A), the instrument includes an instrument-based insertion architecture.

Figure 5:
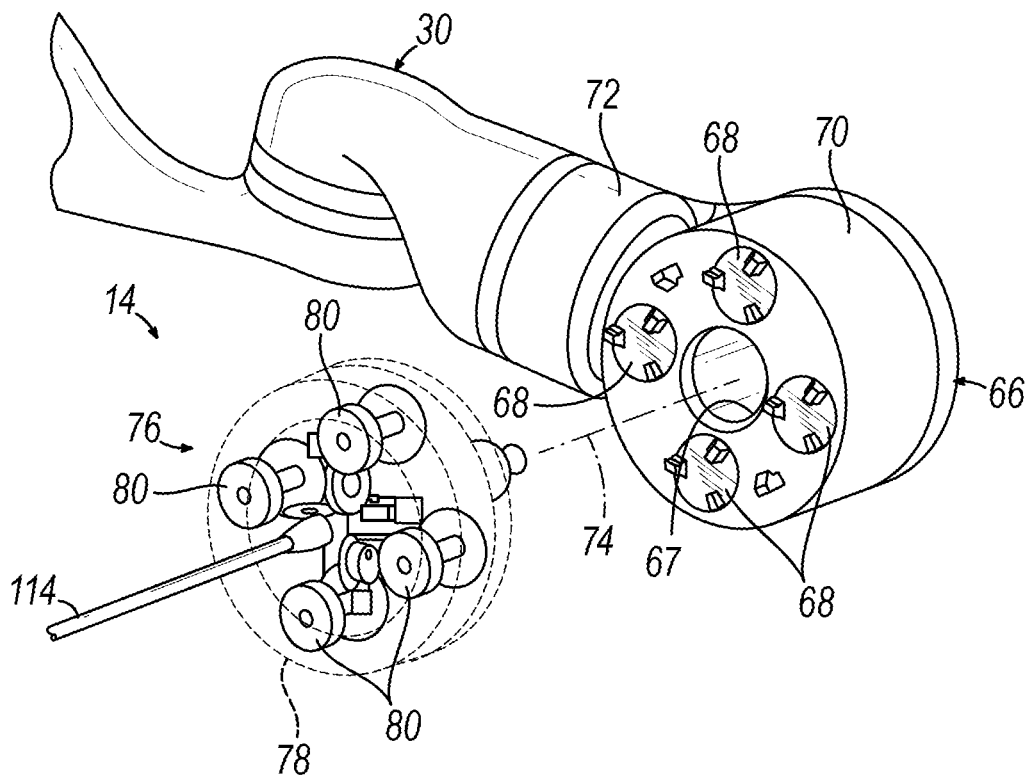
FIG. 5 depicts a partially exploded perspective view of the robotic arm of FIG. 4 having an instrument driver and a first exemplary surgical instrument.

FIG. 5 shows one example of instrument driver (66) in greater detail with surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. Exemplary Surgical Instrument

Figure 6A:
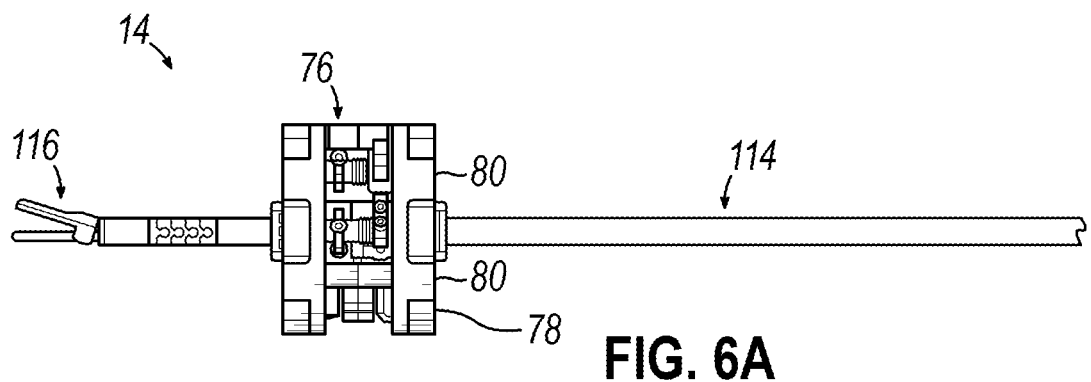
FIG. 6A depicts a side elevational view of the surgical instrument of FIG. 5 in a retracted position.
Figure 6B:
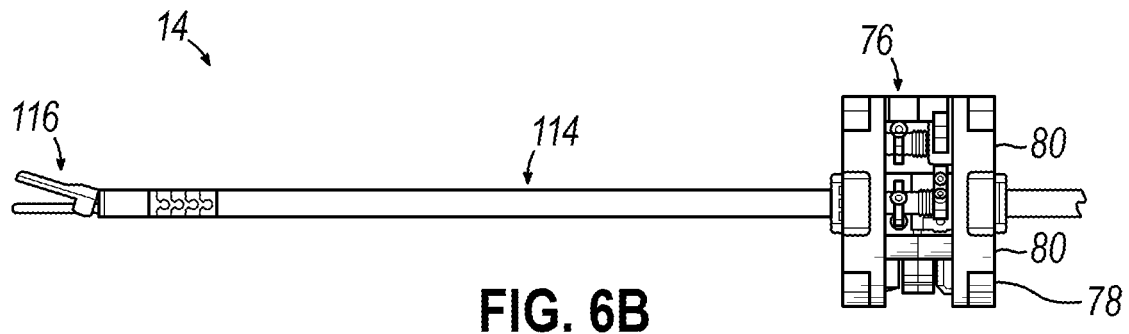
FIG. 6B depicts the side elevational view the surgical instrument similar to FIG. 6A, but in an extended position.

With respect to FIGS. 5-6B and in cooperation with instrument driver (66) discussed above, surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of instrument base (76) with an axis substantially parallel to the axes of the drive inputs (80) as discussed briefly above. With shaft assembly (114) positioned at the center of instrument base (76), shaft assembly (114) is coaxial with instrument driver axis (74) when attached and movably received in clearance bore (67). Thus, rotation of rotational assembly (70) causes shaft assembly (114) of surgical instrument (14) to rotate about its own longitudinal axis while clearance bore (67) provides space for translation of shaft assembly (114) during use.

To this end, FIGS. 5-6B show surgical instrument (14) having the instrument-based insertion architecture as discussed briefly above. Surgical instrument (14) includes elongated shaft assembly (114), end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriages, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

II. Exemplary Surgical Stapler

In some instances, it may be desirable to use various alternative surgical instruments with robotic systems (10, 28) described above in addition to, or in lieu of, surgical instrument (14). Such alternative surgical instruments may be desirable to provide improved operability when used with robotic systems (10, 28). For instance, as described above, surgical instrument (14) may move between a retracted position and extended position. Additionally, it may be beneficial to translate a portion of surgical instrument (14) along a support structure to provide increased surgical access without increasing the dimensions of surgical instrument (14). As also described above, use of rotational assembly (70) of robotic arm (20, 32) may enable rotation of the entire surgical instrument (14), rather than specific structures of surgical instrument (14) being rotatable.

One such example of these alternative surgical instruments includes a second exemplary surgical instrument (210), which may also be referred to as surgical stapler (210) and is discussed below in greater detail. Additional examples of alternative surgical instruments and/or associated features for incorporation with robotic systems (10, 28) are described in U.S. patent application Ser. No. 16/946,363, entitled "Articulation Mechanisms for Robotic Surgical Tools," filed on Jun. 18, 2020, published as U.S. Pub. No. 2021/0393340 on Dec. 23, 2021; U.S. patent application Ser. No. 17/077,067, entitled "Surgical Instrument and Carrier KART Supporting Ultrasonic Transducer," filed on Oct. 22, 2020, published as U.S. Pub. No. 2022/0125465 on Apr. 28, 2022; U.S. patent application Ser. No. 17/077,086, entitled "Carrier KART and Jaw Closure of an Ultrasonic Surgical Instrument," filed on Oct. 22, 2020, published as U.S. Pub. No. 2022/0125466 on Apr. 28, 2022; U.S. patent application Ser. No. 17/077,130, entitled "Surgical Instrument with Clamping Sensor Feedback and Related Methods," filed on Oct. 22, 2020, published as U.S. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020, published as U.S. Pub. No. 2022/0125470 on Apr. 28, 2022; U.S. patent application Ser. No. 17/077,250, entitled "Ultrasonic Surgical Instrument with a Carrier KART and Reusable Stage," filed on Oct. 22, 2020, published as U.S. Pub. No. 2022/0125472 on Apr. 28, 2022; U.S. patent application Ser. No. 17/077,373, entitled "Surgical Instrument with a Carrier KART and Various Communication Cable Arrangements," filed on Oct. 22, 2020, published as U.S. Pub. No. 2022/0125473 on Apr. 28, 2022; U.S. patent application Ser. No. 17/077,139, entitled "Ultrasonic Surgical Instrument with a Fixed Transducer Grounding," filed on Oct. 22, 2020, published as U.S. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. No. 2022/0125460 on Apr. 28, 2022; U.S. patent application Ser. No. 17/077,152, entitled "Damping Rings for an Ultrasonic Surgical Instrument," filed on Oct. 22, 2020, issued as U.S. Pat. No. 11,806,037 on Nov. 7, 2023 ; U.S. patent application Ser. No. 17/077,110, entitled "Ultrasonic Surgical Instrument with a Mid-shaft Closure System and Related Methods," filed on Oct. 22, 2020, published as U.S. Pub. No. 2022/125468 on Apr. 28, 2022; U.S. patent application Ser. No. 17/076,956, entitled "Surgical Instrument with an Articulatable Shaft Assembly and Dual End Effector Roll," filed on Oct. 22, 2020, published as U.S. Pub. No. 2022/0125463 on Apr. 28, 2022; U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022; and/or U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022. The disclosure of each of the above-cited U.S. patent applications is incorporated by reference herein in its entirety. Various features of these alternative examples of surgical instruments may be readily incorporated into a surgical robotic system, such as robotic systems (10, 28), such that the invention is not intended to be unnecessarily limited to these particular alternative surgical instruments discussed herein.

A. Overview

Figure 7:
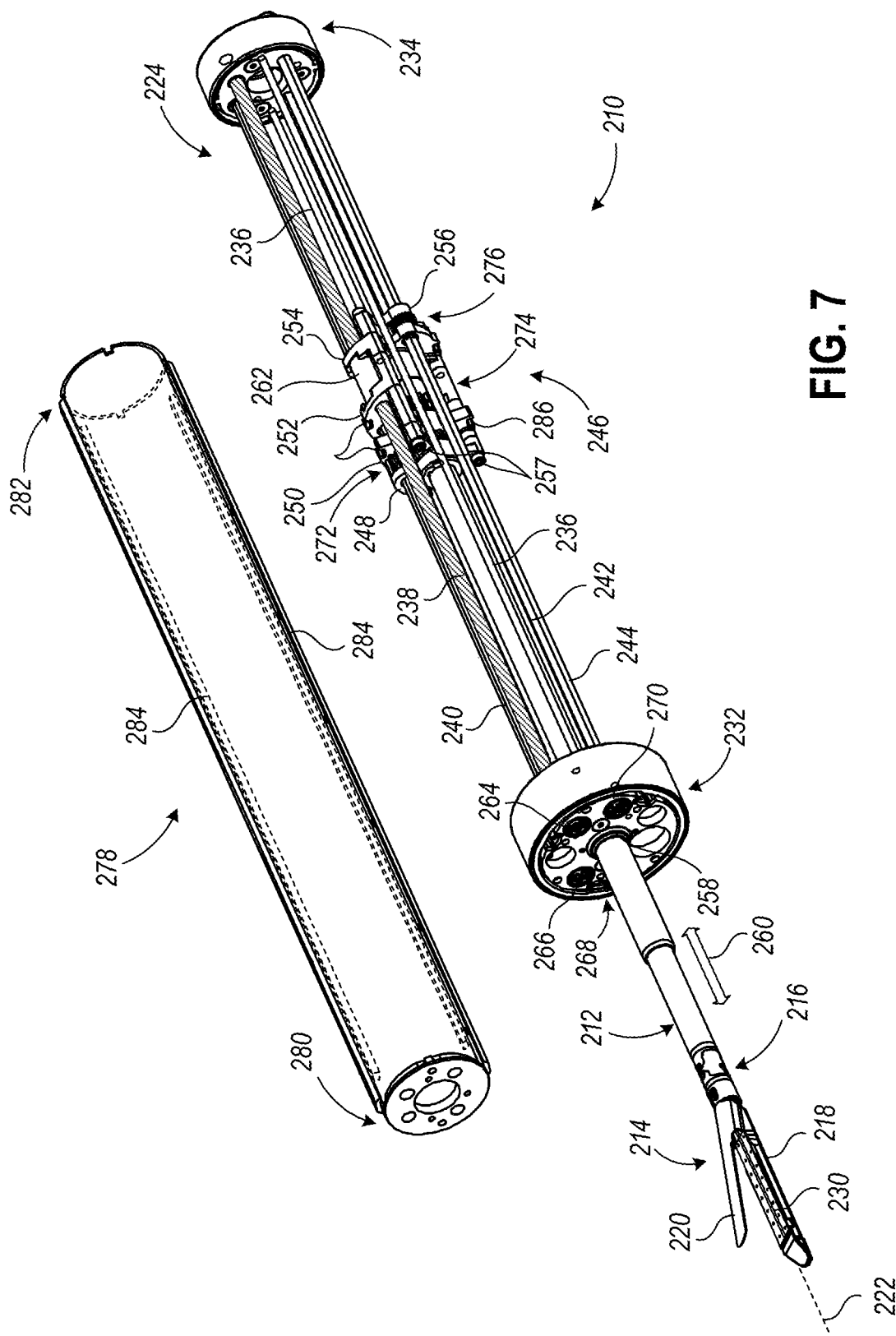
FIG. 7 depicts a perspective view of a second exemplary surgical instrument having a first example of a carriage operatively connected to an end effector configured for cutting and sealing transected tissue with a plurality of staples.

FIG. 7 is an exemplary surgical instrument (210) that may incorporate some or all of the principles of the present disclosure. Surgical instrument (210) may be similar in some respects to any of the instruments described above with reference to FIGS. 1-6B and, therefore, may be used in conjunction with a robotic surgical system, such as robotic systems (10, 28) of FIGS. 1-6B. As illustrated, surgical instrument (210) includes an elongated shaft (212), an end effector (214) arranged at a distal end of shaft (212), and an articulable wrist (216), which may also be referred to herein as a "wrist joint," that interposes and couples end effector (214) to the distal end of shaft (212).

Surgical instrument (210) can have any of a variety of configurations capable of performing one or more surgical functions. In the present example, end effector (214) comprises a surgical stapler, which may also be referred to herein as an "endocutter," configured to cut and staple tissue for fastening. As illustrated, end effector (214) includes opposing jaws (218, 220) configured to move, which may also be referred to as "articulate," between open and closed positions. Alternatively, end effector (214) may comprise other types of instruments requiring opposing jaws such as, but not limited to, other surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In another example, end effector (214) may instead comprise any end effector or instrument capable of being operated in conjunction with a robotic system, such as robotic systems (10, 28), and related methods. Such end effectors, and more generally instruments, include, but are not limited to, a suction irrigator, an endoscope (e.g., a camera), an ultrasonic instrument, an RF instrument, or any combination thereof.

One or both of jaws (218, 220) may be configured to pivot and actuate end effector (214) between open and closed positions. In the illustrated example, upper jaw (220) is rotatable, and more particularly pivotable, relative to lower jaw (218) to move between an open, unclamped position and a closed, clamped position. In other examples, however, lower jaw (218) may move relative to upper jaw (220). In still other examples, both lower and upper jaws (218, 220) may move to actuate end effector (214) between open and closed positions.

In the present example, lower jaw (218) is referred to as a "cartridge" or "channel" jaw, and upper jaw (220) is referred to as an "anvil" jaw. Lower jaw (218) may include a frame that houses or supports a staple cartridge, and upper jaw (220) is pivotally supported relative to upper jaw (220) and defines a surface that operates as an anvil to deform staples ejected from the staple cartridge during operation.

Wrist (216) enables end effector (214) to pivot relative to shaft (212) and thereby position end effector (214) at various desired orientations and locations relative to a surgical site. In the present example, wrist (216) is configured such that end effector (214) pivots laterally left and laterally right relative to a longitudinal axis (222) of shaft (212). In other examples, wrist (216) may alternatively provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a robotic surgical system (e.g., end effector (214)) with respect to a given reference Cartesian frame. As used herein, "surge" refers to forward and backward translational movement, "heave" refers to translational movement up and down, and "sway" refers to translational movement left and right. With regard to rotational terms, "roll" refers to tilting side to side, "pitch" refers to tilting forward and backward, and "yaw" refers to turning left and right.

Still referring to FIG. 7, surgical instrument (210) includes a drive housing (224) that houses an actuation system designed to facilitate articulation of wrist (216) and actuation of end effector (214) (e.g., clamping, firing, rotation, articulation, energy delivery, etc.). Drive housing (224), alternately referred to as a "stage," provides various coupling features that releasably couple surgical instrument (210) to an instrument driver of a robotic surgical system. Drive housing (224) includes a plurality of drive members (226, 228) (see FIG. 8A) that extend to wrist (216) and end effector (214). Selective actuation of one or more of drive members (226, 228) causes end effector (214) to pivot relative to shaft (212) at wrist (216). Selective actuation of one or more other drive members (not shown) causes end effector (214) to actuate, such as by closing and/or opening jaws (218, 220) and thereby enabling end effector (214) to clamp tissue. Once tissue is clamped between opposing jaws (218, 220), actuating end effector (214) may further include "firing" end effector (214), which may refer to causing a cutting element (not shown), such as a knife, to distally advance within a slot (230) defined in lower jaw (218). While moving distally, cutting element (not shown) transects tissue clamped between opposing jaws (218, 220). Moreover, as cutting element (not shown) advances, a plurality of staples (not shown) contained within staple cartridge (e.g., housed within lower jaw (218)) are urged into deforming contact with corresponding anvil surfaces, such as pockets, provided on upper jaw (220). In one example, the deployed staples may form multiple rows of staples configured to seal opposing sides of the transected tissue.

Drive housing (224) has a distal end (232) and an opposing, proximal end (234).

Distal end (232) may also be referred to herein as a "handle." In some examples, one or more struts (236), such as two such struts (236), extend longitudinally between the distal and proximal ends (232, 234) to fix a distance between distal and proximal ends (232, 234), provide structural stability to drive housing (224), and secure distal end (232) relative to proximal end (234).

Drive housing (224) also includes a lead screw (238) and one or more splines (240, 242, 244), which also extend longitudinally between the distal and proximal ends (232, 234). In the present example, drive housing (224) includes a first spline (240), a second spline (242), and a third spline (244). While three splines (240, 242, 244) are depicted in the drive housing (224), more or less than three such splines (240, 242, 244) may be included in an alternative drive housing (224) in another example. Unlike struts (236), lead screw (238) and splines (240, 242, 244) are rotatably mounted to distal and proximal ends (232, 234). To this end, selective rotation of lead screw (238) and splines (240, 242, 244) causes various functions of drive housing (224) to transpire, such as translating end effector (214) along longitudinal axis (222), pivoting end effector (214) at wrist (216), opening or closing jaws (218, 220), and/or firing end effector (214).

Drive housing (224) further includes a carriage (246) movably mounted along lead screw (238) and splines (240, 242, 244) and houses various activating mechanisms configured to cause operation of specific functions of end effector (214). Carriage (246) may comprise two or more layers, shown in the present example as a first layer (248), a second layer (250), a third layer (252), a fourth layer (254), and a fifth layer (256). Lead screw (238) and splines (240, 242, 244) each extend through portions of one or more of layers (248, 250, 252, 254, 256) to allow carriage (246) to translate along longitudinal axis (222) with respect to lead screw (238) and splines (240, 242, 244). In some examples, layers (248, 250, 252, 254, 256) may be secured to each other in series using one or more mechanical fasteners (257) extending between first layer (248) and fifth layer (256) and through coaxially aligned holes defined in some or all of layers (248, 250, 252, 254, 256). While five layers (248, 250, 252, 254, 256) are shown in the present example, more or less than five such layers may be included in an alternative carriage (246) such that the invention is not intended to be unnecessarily limited to five layers (248, 250, 252, 254, 256).

Shaft (212) is coupled to and distally extends from carriage (246) through a central aperture (258) in distal end (232). Carriage (246) is movable between distal and proximal ends (232, 234) along longitudinal axis (222) and is thereby able to advance or retract end effector (214) relative to drive housing (224), as indicated by the arrows (260). More specifically, in some examples, carriage (246) includes a carriage nut (262) mounted to lead screw (238) and secured between third and fourth layers (252, 254). The outer surface of lead screw (238) defines outer helical threading and carriage nut (262) defines corresponding internal helical threading configured to be received within outer helical threading. As a result, rotation of lead screw (238) causes carriage nut (262) to advance or retract carriage (246) along longitudinal axis (222) and correspondingly advance or retract end effector (214) relative to drive housing (224).

As indicated above, lead screw (238) and splines (240, 242, 244) are rotatably mounted to distal and proximal ends (232, 234). More specifically, distal end (232) of drive housing (224) may include one or more rotatable drive inputs actuatable to independently rotate lead screw (238) and splines (240, 242, 244). In the present example, drive housing (224) includes a first drive input (264), a second drive input (266), a third drive input (268), and a fourth drive input (270). As described below, each drive input (264, 266, 268, 270) may be matable with a corresponding drive output of an instrument driver such that rotation of a given drive output correspondingly rotates the associated drive input (264, 266, 268, 270) and thereby rotates the mated lead screw (238) or spline (240, 242, 244). While four drive inputs (264, 266, 268, 270) are shown in the present example, more or less than four may be included in an alternative drive housing such that the invention is not intended to be unnecessarily limited to four such drive inputs (264, 266, 268, 270).

First drive input (264) as shown is operatively coupled to lead screw (238) such that rotation of first drive input (264) correspondingly rotates lead screw (238), which causes carriage nut (262) and carriage (246) to advance or retract along longitudinal axis (222), depending on the rotational direction of lead screw (238). Second drive input (266) as shown is operatively coupled to first spline (240) such that rotation of second drive input (266) correspondingly rotates first spline (240). In one example, first spline (240) is operatively coupled to a first activating mechanism (272) of carriage (246), and first activating mechanism (272), in turn, is operable to open and close jaws (218, 220). Third drive input (268) as shown is operatively coupled to second spline (242) such that rotation of third drive input (268) correspondingly rotates second spline (242). In one example, second spline (242) is operatively coupled to a second activating mechanism (274) of carriage (246), and second activating mechanism (274) is operable to articulate end effector (214) at wrist (216). Fourth drive input (270) as shown is operatively coupled to third spline (244) such that rotation of fourth drive input (270) correspondingly rotates third spline (244). In one example, third spline (244) is operatively coupled to a third activating mechanism (276) of carriage (246), and third activating mechanism (276) is operable to fire cutting element (not shown) of end effector (214).

Drive housing (224) of the present example also includes a shroud (278) sized to receive and otherwise surround carriage (246), lead screw (238), and splines (240, 242, 244). Shroud (278) comprises a tubular structure having a distal end (280) matable with distal end (232) of drive housing (224), and a proximal end (282) matable with proximal end (234) of drive housing (224). Rails (284) extend longitudinally and parallel to lead screw (238) and are sized to be received within corresponding notches (286) defined on an outer periphery of carriage (246) and, more particularly, on the outer periphery of one or more of carriage layers (248, 250, 252, 254, 256). As carriage (246) translates along longitudinal axis (222), rails (284) are configured to maintain an angular position of carriage (246) and bear any torsional loading that may otherwise adversely affect movement and/or operation of carriage (246) during use.

Figure 8A:
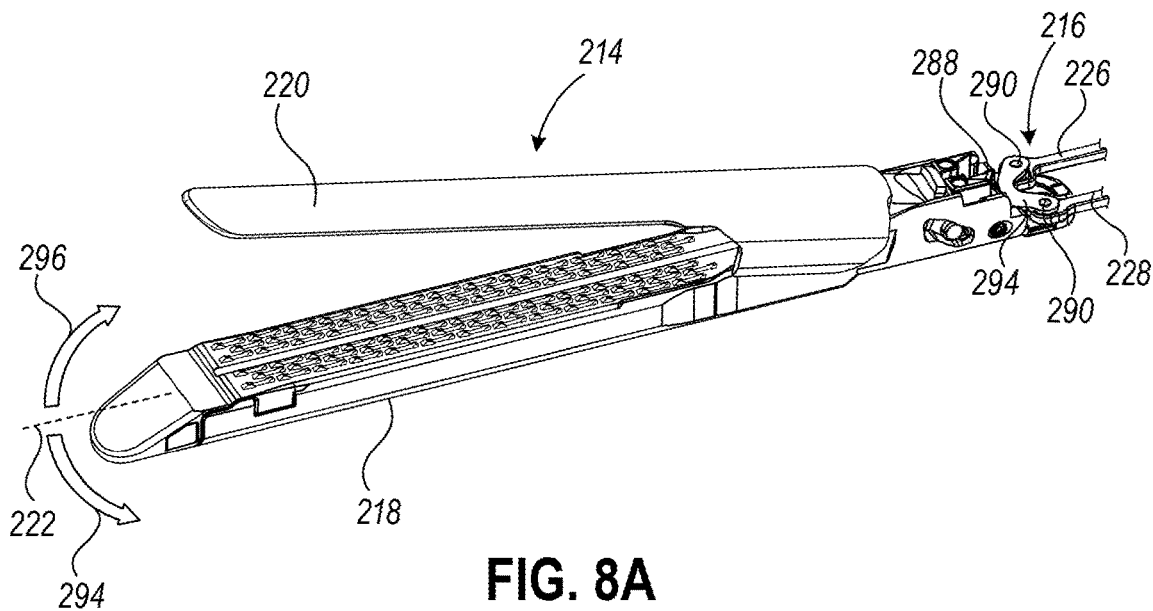
FIG. 8A depicts an enlarged perspective view of the end effector of FIG. 7 showing a wrist configured to articulate the end effector.

As shown in FIG. 8A, wrist (216) more particularly has drive members (226, 228) interconnected with end effector (214) and configured to articulate end effector (214) relative to longitudinal axis (222). End effector (214) is mounted to an end effector mount (288) having two articulation pins (290), and a distal end of each drive member (226, 228) is rotatably mounted to a corresponding one of articulation pins (290). Drive members (226, 228) are also interconnected at distal ends via a distal link (292), which together comprise a linkage configured to support articulation of end effector mount (288) and, in turn, articulation of end effector (214).

Drive members (226, 228) translate antagonistically and parallel along longitudinal axis (222), such that as first drive member (226) moves distally second drive member (228) moves proximally, and vice versa. Moreover, distal movement of first drive member (226) and simultaneous proximal movement of second drive member (228) cooperatively act on end effector mount (288) to cause end effector (214) to rotate counterclockwise, as indicated by an arrow (294). In contrast, proximal movement of first drive member (226) and simultaneous distal movement of second drive member (228) cooperatively act on end effector mount (288) to cause end effector (214) to rotate clockwise, as indicated by an arrow (296).

Figure 8B:
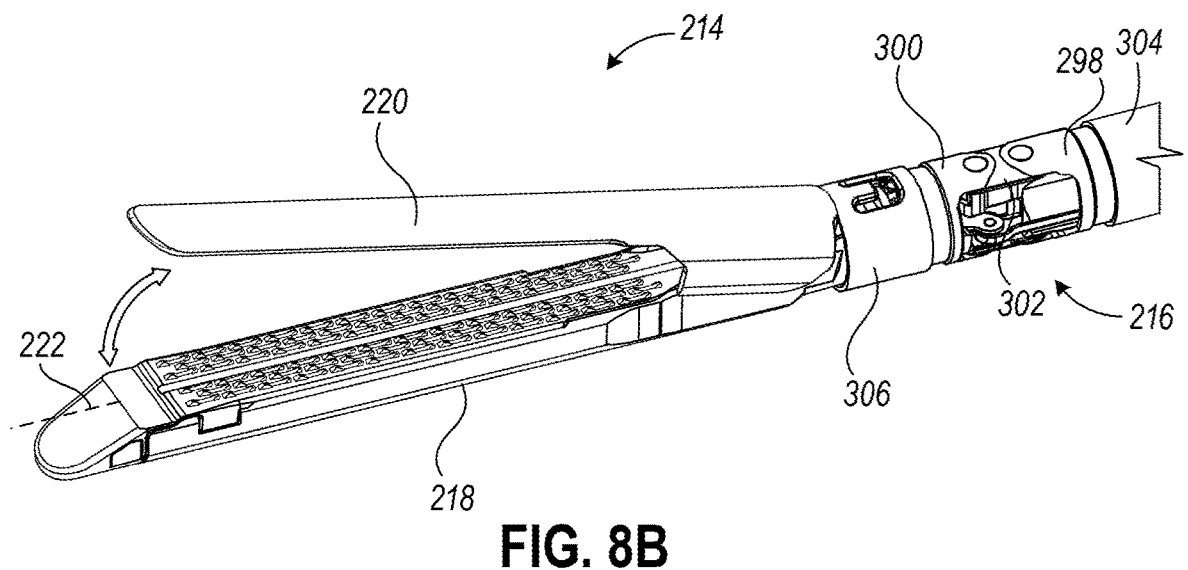
FIG. 8B depicts the enlarged perspective view of the end effector similar to FIG. 8A, but showing an upper jaw configured to selectively move between open and closed positions relative to a lower jaw.

FIG. 8B shows end effector (214) having jaws (218, 220) configured to selectively move between open and closed positions. To this end, wrist (216) has a proximal clevis (298), distal clevis (300), and a closure link (302) configured to operatively couple proximal and distal devises (298, 300) across wrist (216). Proximal clevis (298) of the present example is coupled a distal end of a closure tube (304) whereas distal clevis (300) is coupled to a closure ring (306). Axial movement of closure tube (304) along longitudinal axis (222) correspondingly moves proximal clevis (298) in the same axial direction, and closure link (302) is configured to transmit the axial load through wrist (216) to close jaws (218, 220) of end effector (214). Closure link (302) transmits closure load via translation of closure tube (304) from distal clevis (300) to proximal clevis (298) such that closure ring (306) correspondingly pushes or pulls on upper jaw (220) to open or close upper jaw (220) relative to lower jaw (218) as applicable.

While the above articulation of end effector (214) relative to longitudinal axis (222) and movement of upper jaw (220) between open and closed positions is shown as described herein, it will be appreciated that such articulation and movement may be performed at end effector (214) with alternative structures. The invention is thus not intended to be unnecessarily limited to the particular end effector (214) with associated wrist (216) and shown and described herein.

Figure 9:
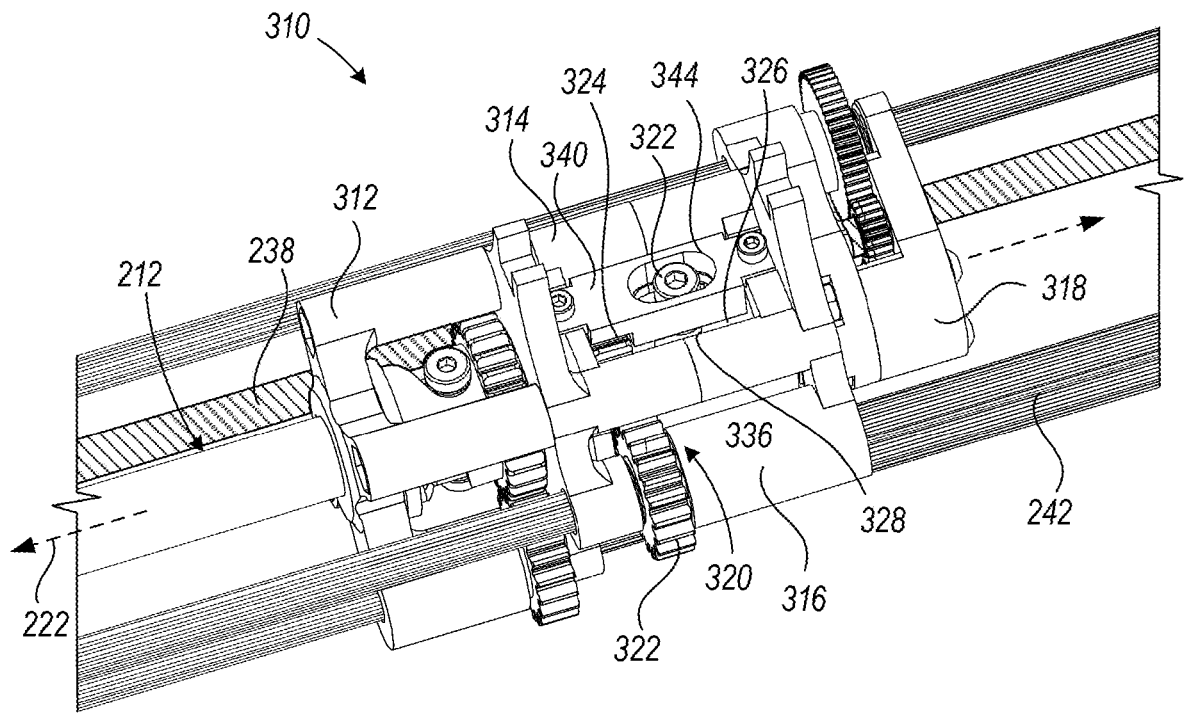
FIG. 9 depicts an enlarged perspective view of a second example of a carriage incorporated into the surgical instrument of FIG. 7 and having an articulation activating mechanism.
Figure 10:
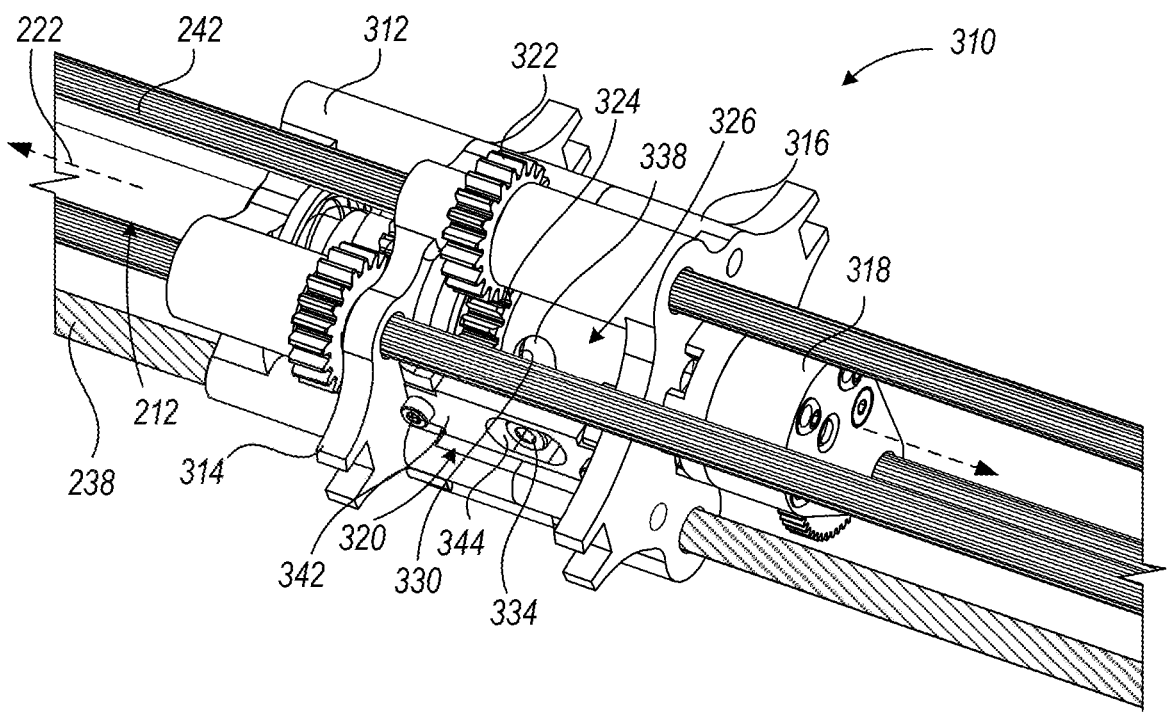
FIG. 10 depicts another enlarged perspective view of the carriage of FIG. 9 incorporated into the surgical instrument of FIG. 7.

B. Activating Mechanisms for Articulation and Jaw Movement i. Articulation Activating Mechanism with Barrel Cam FIGS. 9 and 10 show another example of a carriage (310) similar in some respects to carriage (246) (see FIG. 7) discussed above and may replace carriage (246) (see FIG. 7) in one or more examples such that like numbers below indicate like features discussed above. Carriage (310) is thus like carriage (246) (see FIG. 7) unless noted otherwise below. Carriage (310) more particularly has two or more layers, such as a first layer (312), a second layer (314), a third layer (316), and a fourth layer (318). Shaft (212) is coupled to and extends distally from carriage (310) such that carriage (310) is configured to move along longitudinal axis (222) to correspondingly advance or retract end effector (214) shown in FIG. 8A.

With reference to FIGS. 8A and 9-10, carriage (310) includes an activating mechanism (320) configured to articulate end effector (214) relative to longitudinal axis (222) (see FIG. 8A) at wrist (216). Second spline (242) is operatively coupled to activating mechanism (320) such that rotating second spline (242) correspondingly actuates activating mechanism (320) and thereby causes wrist (216) to articulate. More specifically, a drive gear (322) is included with second spline (242) and positioned to intermesh with a driven gear (324) coupled to an articulation barrel (326). As spline (242) rotates, drive gear (322) drives driven gear (324) and correspondingly rotates articulation barrel (326) about longitudinal axis (222).

Articulation barrel (326) of the present example includes a first cam profile (328) and a second cam profile (330). Activating mechanism (320) further includes a first follower pin (332) and a second follower pin (334). First follower pin (332) extends through first cam profile (328) and is coupled to a first carrier (336), and second follower pin (334) extends through second cam profile (330) and is coupled to a second carrier (338). Each cam profile (328, 330) extends about a circumference of articulation barrel (326) (e.g., in a helical pattern), but cam profiles (328, 330) are defined at opposite angles relative to each other. As drive gear (322) drives driven gear (324), articulation barrel (326) correspondingly rotates about longitudinal axis (222), thus urging follower pins (332, 334) to traverse the oppositely-angled cam profiles (328, 330), respectively. As follower pins (332, 334) traverse cam profiles (328, 330), underlying carriers (336, 338) are urged in equal but opposite axial directions along longitudinal axis (222). Depending on a rotational direction of drive gear (322), carriers (336, 338) may be drawn axially toward each other or moved axially away from each other.

In one or more examples, activating mechanism (320) further includes a first articulation torque bar (340) and a second articulation torque bar (342). Articulation torque bars (340, 342) extend between second and third layers (314, 316) and are secured to each layer (314, 316). Each articulation torque bar (340, 342) defines a slot (344) sized to receive heads of corresponding follower pins (332, 334). During use of activating mechanism (320), articulation torque bars (340, 342) are configured to maintain an axial position of corresponding follower pins (332, 334).

Figure 11:
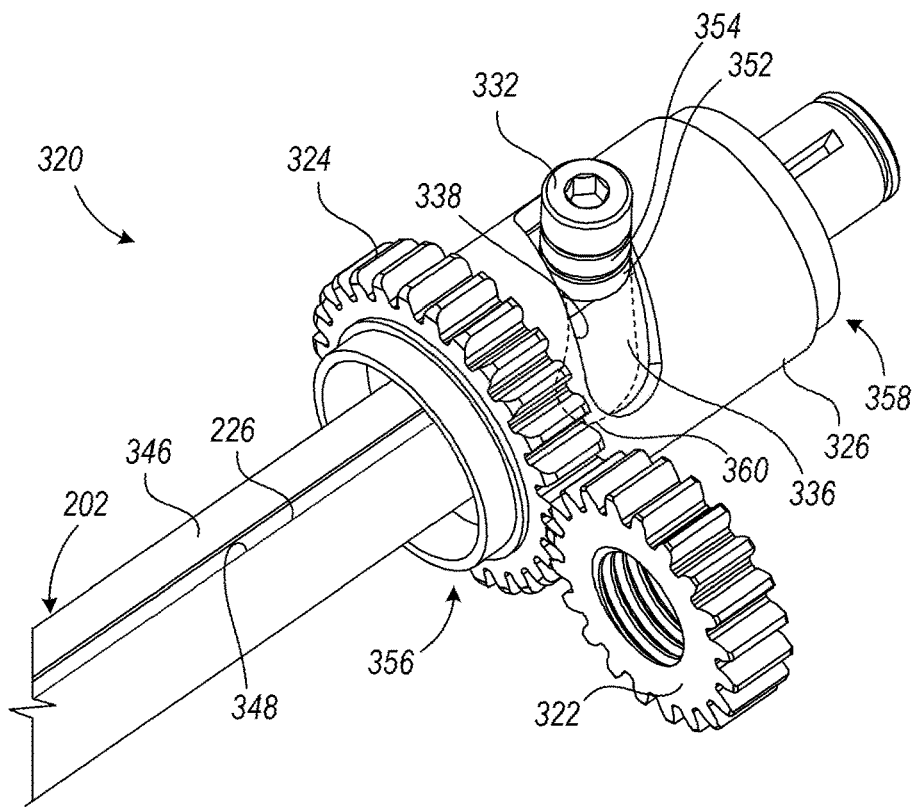
FIG. 11 depicts a perspective view of the articulation activating mechanism of FIG. 9.
Figure 12:
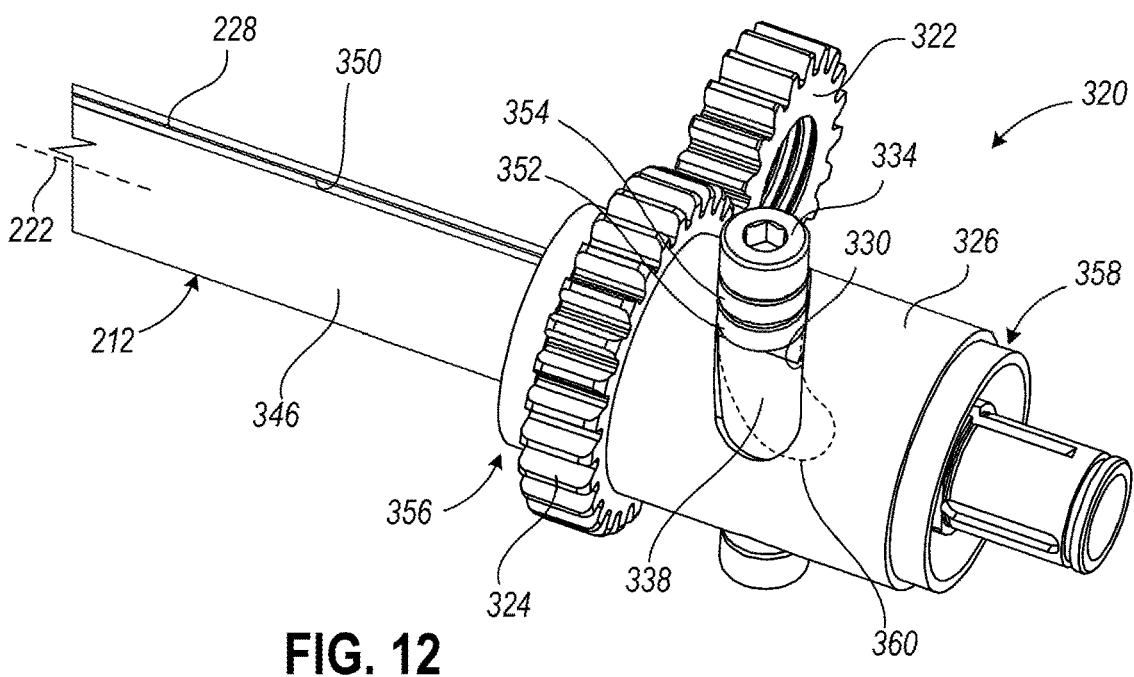
FIG. 12 depicts another perspective view of the articulation activating mechanism of FIG. 9.

FIGS. 11 and 12 more particularly show articulation barrel (326) having a generally cylindrical structure that extends about shaft (212) about an inner grounding shaft (346). First and second carriers (336, 338) interpose inner grounding shaft (346) and articulation barrel (326) and are independently movable along longitudinal axis (222). First carrier (336) is operatively coupled to first drive member (226), which extends distally to wrist (216) (see FIG. 8A) at least partially within a slot (348) defined in inner grounding shaft (346). Additionally, second carrier (338) is operatively coupled to second drive member (228), which extends distally to wrist (216) (see FIG. 8A) at least partially within a slot (350) defined in inner grounding shaft (346).

Follower pins (332, 334) extend through corresponding cam profiles (328, 330) and are coupled to associated carriers (336, 338), respectively. In one example, one or both of follower pins (332, 334) may include bearings, such as a first bearing (352) and a second bearing (354). Such first and second bearings (352, 354) are stacked on top of each other with a shaft of each follower pin (332, 334) extending through first and second bearings (352, 354). First bearings (352) are configured to bear against the inner walls of cam profiles (328, 330) as articulation barrel (326) rotates and follower pins (332, 334) are urged to traverse cam profiles (328, 330) respectively, reducing friction thereagainst. Second bearings (354) are configured to bear against the inner walls of slot (344) (see FIGS. 9-10) defined in corresponding torque articulation bars (340, 342) (see FIGS. 9-10) to prevent rotational movement of follower pins (332, 334) as articulation barrel (326) rotates.

Articulation barrel (326) has a distal end (356) and a proximal end (358), and driven gear (324) may be defined proximate to distal end (356) in one example, provided proximate to proximal end (358) in another example, or alternatively positioned anywhere in between distal and proximal ends (356, 358) in still other examples. Cam profiles (328, 330) are positioned between distal and proximal ends (356, 358) and may comprise straight slots extending at a constant angle about a circumference of articulation barrel (326), but at opposite angular directions. In one example with straight cam profiles (328, 330), movement and force applied to carriers (336, 338) and drive members (226, 228) is constant during articulation of end effector (214) (see FIG. 8A). In such an example, cam profiles (328, 330) may be more particularly described as helical cam slots and follower pins (332, 334) may be more particularly described as linear cam followers.

In another example, cam profiles (328, 330) may not be entirely straight, but may alternatively diverge at one or more inflection points along a length, which may also be referred to as a "path," of cam profile (328, 330). More specifically, cam profiles (328, 330) may diverge from straight and define a more or less aggressive path, such as path (360), depending on a direction at the inflection point. Higher or lower angles of cam profiles (328, 330) alter mechanical advantage obtained as follower pins (332, 334) traverse cam profiles (328, 330) and act on interconnected carriers (336, 338), respectively. Such differing mechanical advantages may be beneficial in one or more uses of articulating end effector (214) relative to longitudinal axis (222).

ii. Jaw Activating Mechanism with Barrel Cam

Figure 13:
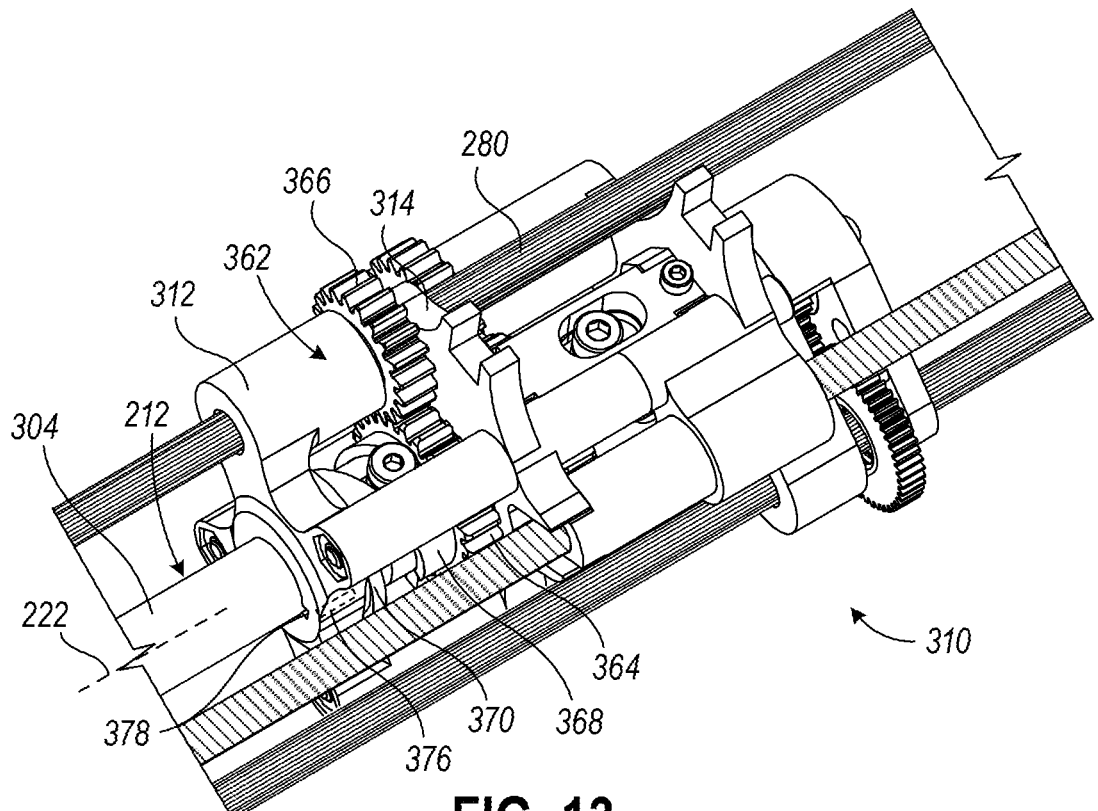
FIG. 13 depicts an enlarged perspective view of the carriage of FIG. 9 having a jaw activating mechanism.
Figure 14:
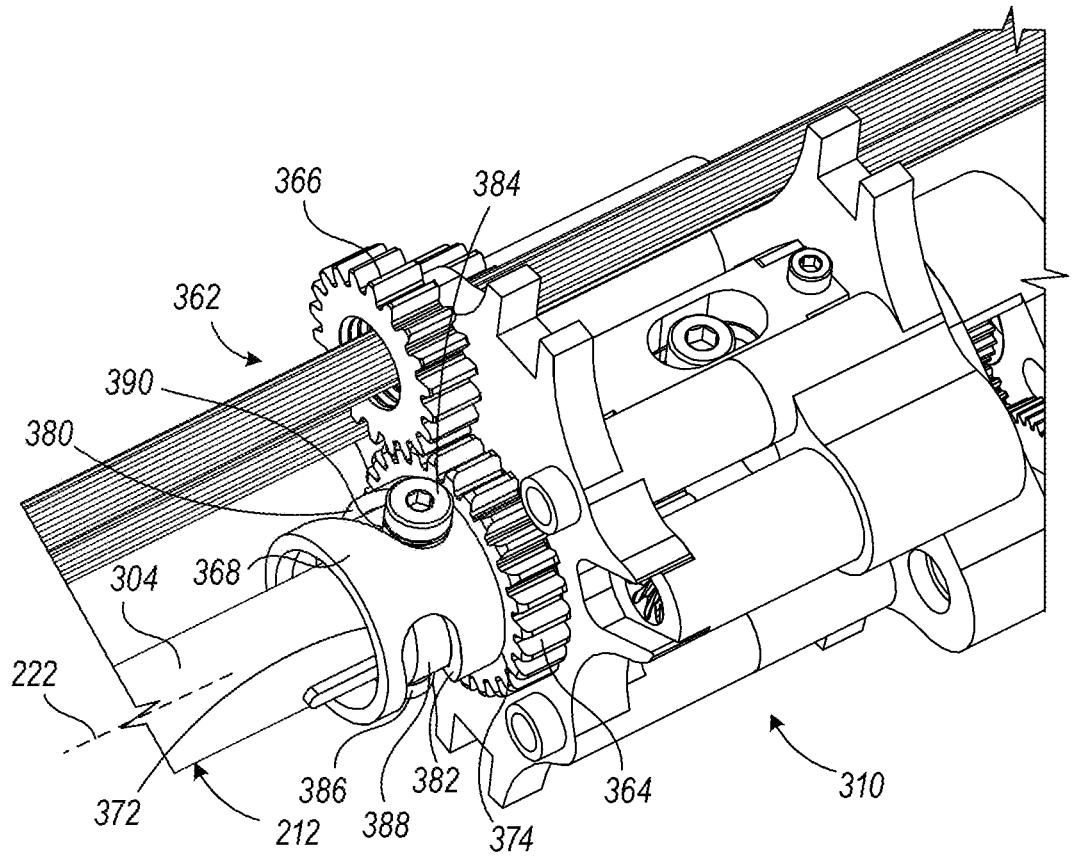
FIG. 14 depicts another enlarged perspective view of the carriage of FIG. 13 with the jaw activating mechanism.

FIGS. 13-14 show carriage (310) discussed above including another activating mechanism (362) configured to move upper jaw (220) relative to lower jaw (218) between the open and closed positions as shown with further reference to FIG. 8B. To this end, first spline (240) is configured to direct such movement of upper jaw (220) such that rotating first spline (240) (e.g., via rotation of second drive input (266) (see FIG. 7) correspondingly actuates activating mechanism (362) and thereby causes closure tube (304) of shaft (212) to advance or retract along longitudinal axis (222).

Activating mechanism (362) further includes a driven gear (364) that intermeshes with a drive gear (366) of first spline (240) such that rotation of drive gear (366) correspondingly rotates driven gear (364). As shown in the present example, driven gear (364) is coupled with a closure barrel (368). As spline (240) rotates, drive gear (366) drives driven gear (364) and causes closure barrel (368) to rotate about longitudinal axis (222). Closure barrel (368) is positioned in carriage (310) between first and second layers (312, 314). One or more thrust bearings may be arranged at one or both axial ends of closure barrel (368) to effectively bear axial loading on closure barrel (368) and reduce friction during use of activating mechanism (362). More particularly, a plurality of thrust bearings (370) in the present example is arranged at a distal end (372) of closure barrel (368), which is opposite from a proximal end (374) of closure barrel (368) and interpose closure barrel (368) and first layer (248). Additionally, activating mechanism (362) further includes a key (376) on the outer surface of closure tube (304). Key (376) is received within a slot (378) defined in first layer (312) of carriage (310). Actuating activating mechanism (362) causes closure tube (304) to translate along longitudinal axis (222) and correspondingly causes key (376) to translate longitudinally within slot (378) to thereby prevent closure tube (304) from rotating during longitudinal movement of closure tube (304).

Closure barrel (368) has a generally cylindrical structure that extends about closure tube (304) and defines a first cam profile (380) and a second cam profile (382). Each cam profile (380, 382) extends a distance about a circumference of closure barrel (368) (e.g., in a generally helical pattern). While closure barrel (368) provides two cam profiles (380, 382) the invention is not intended to be unnecessarily limited to two such cam profiles (380, 382) such that an alternative number of cam profiles may be similarly incorporated into closure barrel (368).

Activating mechanism (362) further includes a first follower pin (384) and a second follower pin (386) extending through first and second cam profiles (380, 382), respectively, and are operatively coupled to a proximal end of closure tube (304). In one example, first and second follower pins (384, 386) are each coupled to a carrier (388) arranged at the proximal end of closure tube (304). Carrier (388) is configured to receive the proximal end of closure tube (304) and may radially interpose a portion of closure tube (304) and closure barrel (368), and movement of carrier (388) along longitudinal axis (222) will correspondingly move closure tube (304) in a like axial direction.

As drive gear (364) drives driven gear (364), closure barrel (368) correspondingly rotates about longitudinal axis (222), thus urging follower pins (384, 386) to traverse cam profiles (380, 382), respectively. In turn, carrier (388) moves along longitudinal axis (222) and closure tube (304) is urged in the same axial direction. Depending on the rotational direction of drive gear (366), carrier (388) and closure tube (304) may move distally (i.e., to the left in FIG. 14) or proximally (i.e., to the right in FIG. 14) and thereby close or open jaws (218, 220) of end effector (214) as shown in FIG. 8B.

In one example, one or both of follower pins (384, 386) may include one or more bearings (390), and shaft of each follower pin (384, 386) extends through bearings (390). Bearings (390) are configured to bear against inner walls of cam profiles (380, 382) as closure barrel (368) rotates and follower pins (384, 386) traverse cam profiles (380, 382) thereby reducing friction during use.

Figure 15:
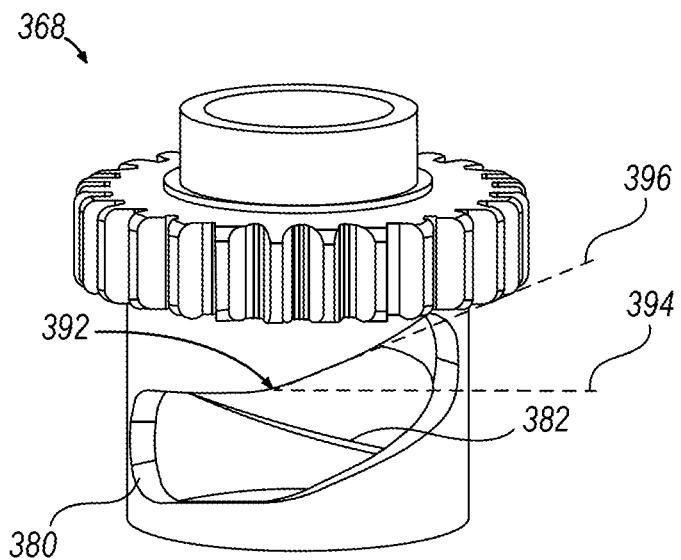
FIG. 15 depicts a first exemplary barrel cam of the jaw activating mechanism of FIG. 13.

FIG. 15 shows one example of the closure barrel (368) in greater detail. As discussed briefly above, each cam profile (380, 382) has a slot extending generally helically about a portion of the circumference of closure barrel (368). In such an example, cam profiles (380, 382) may be more particularly described as helical cam slots, and follower pins (384, 386) may be more particularly described as linear cam followers. Each cam profile (380, 382) has a straight slot extending helically at a constant angle, which may also be referred to herein as a slope, about the circumference of closure barrel (368). The movement applied to carrier (388) and converted into an axial load on closure tube (304) (see FIGS. 13-14) may be constant during actuation of activating mechanism (362) (FIGS. 13-14) through this constant angle.

In one example, one or both of cam profiles (380, 382) may not be entirely straight, but may alternatively diverge at one or more inflection points (392) along a helical length of cam profile (380, 382). More specifically, at inflection point (392), cam profiles (380, 382) change from extending a first distance about the circumference of closure barrel (368) at a first slope (394) to a second distance at a second slope (396) such that second slope (396) has a more or less aggressive path as compared to first slope (394). A higher or lower slope of cam profile (380, 382) will correspondingly alter a mechanical advantage obtained as follower pins (384, 386) traverse cam profiles (380, 382) and act on interconnected carrier (388). Such mechanical advantage may result in higher axial loads being applied to closure tube (304) (see FIGS. 13-14) and allow jaws (218, 220) (see FIG. 8B) to clamp down with enhanced force and/or greater precision during use.

III. Exemplary Alternative Closure Barrels

In some examples it may be desirable to incorporate certain alternative closure barrels similar to closure barrel (368) into instrument (210) described above or other suitable instruments. For instance, in some examples it may be desirable to include certain features to modify mechanical advantage associated with the closure barrel. In some examples, mechanical advantage may be modified to support certain instrument (210) outputs such as the speed and/or power of actuating lower jaw (218) and/or upper jaw (220). In addition, or in the alternative, mechanical advantage may be modified to support certain instrument (210) inputs to support manual and/or motor-based drive inputs.

Although the examples described below are described in the context of structures similar to closure barrel (368), it should be understood that the same features may be readily applied to other structures of instrument. For instance, structures similar to articulation barrel (326) described above may have at least some overlapping features with structures similar to closure barrel (368). Thus, the same features described below with respect to structures similar to closure barrel (368) may be readily applied to structures similar to articulation barrel (326).

A. Closure Barrel with Exponential Cam Profile

Figure 16:
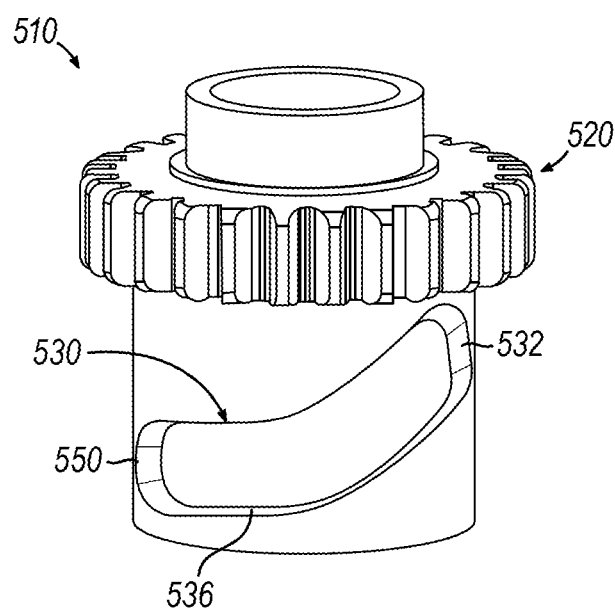
FIG. 16 depicts a perspective view of an exemplary alternative barrel cam for use with the jaw activating mechanism of FIG. 13.

FIG. 16 shows an exemplary alternative closure barrel (510) (alternatively referred to as a barrel cam) that may be readily incorporated into instrument (210) in addition to or in lieu of closure barrel (368). Closure barrel (510) is substantially similar to closure barrel (368) described above in that closure barrel (510) includes a driven gear (520) configured to mesh with drive gear (366) (see FIG. 14) or other similar structures to drive rotation of closure barrel (510). Similarly, closure barrel (510) includes a cam profile (530) configured to receive one or both of follower pins (384, 386) to drive actuation of jaws (218, 220) or other similar structures via rotation of closure barrel (510).

As noted above, closure barrel (510) includes cam profile (530). Cam profile (530) is similar in function as cam profiles (380, 382) described above. However, unlike cam profiles (380, 382) described above, cam profile (530) of the present example defines an exponential profile to alter the drive characteristics provided by closure barrel (510). As will be described in greater detail below, the exponential profile of cam profile (530) approximately corresponds to the shape of an exponential curve. Thus, rather than including a profile with a constant slope or a plurality of sections with different constant slopes, cam profile (530) of the present example includes a profile with a consistently increasing or decreasing slope. In some examples, this configuration may be desirable to vary the speed of actuation over the length of cam profile (530) without relying on variable drive input speed. Additionally, or in the alternative, this configuration may be desirable to vary the mechanical advantage of actuation over the length of cam profile (530).

Figure 17:
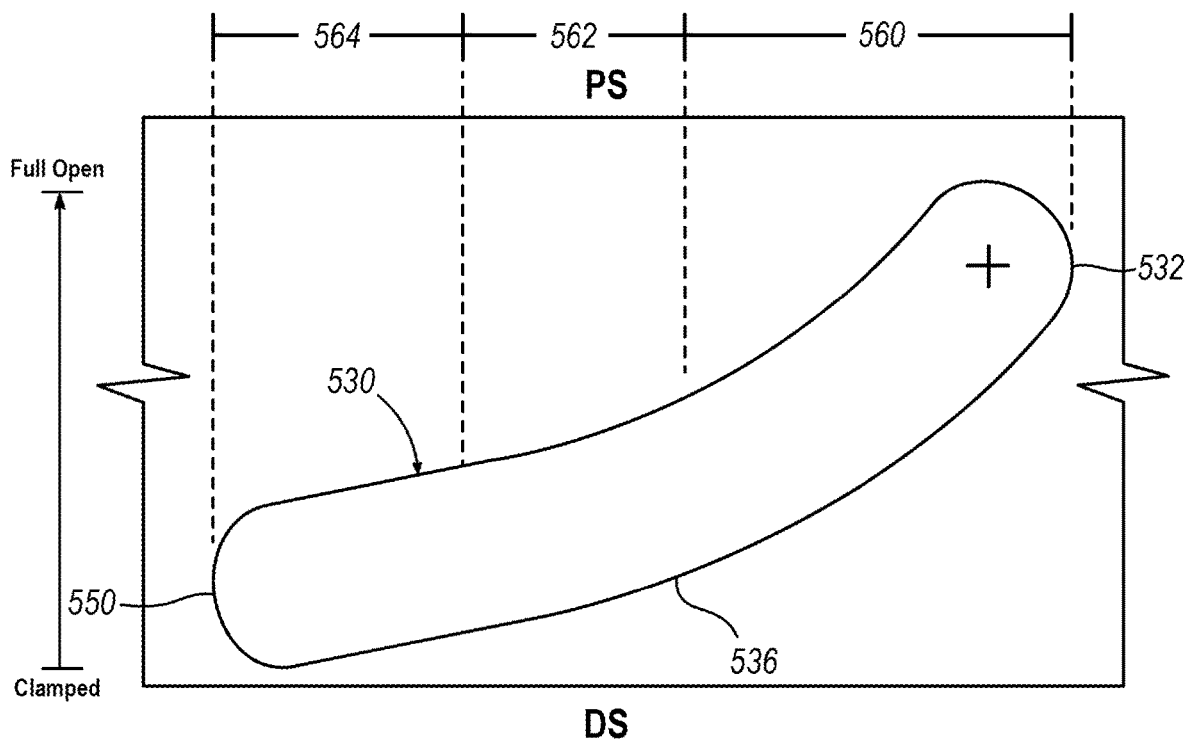
FIG. 17 depicts a schematic view of the barrel cam of FIG. 16.

Cam profile (530) of the present example is shown in greater detail in FIG. 17. In the view shown in FIG. 17, cam profile (530) is shown schematically in an "un-rolled" configuration. In this "un-rolled" configuration, cam profile (530) is shown as if closure barrel (510) shown in FIG. 16 was cut along a longitudinal rotation axis (531) and laid out in a plane. In addition, the orientation of the schematic of FIG. 17 is the same as the perspective in FIG. 16. Specifically, the distal side (DS) of cam profile (530) is oriented downwardly in the present figures, while the proximal side (PS) of cam profile (530) is oriented upwardly in the present figures.

As used herein, a cam profile "slope" refers to an angle of a cam profile, such as cam profile (530), taken at a point relative to the rotation axis (531) when un-rolled in a plane, such as in FIG. 17. The slope essentially extends as a line from this point and intersects the rotation axis (531) to collectively define supplementary angles cumulatively equal to 180°. As also used herein, a relatively higher slope is formed with a greater difference between these supplementary angles, whereas a relatively lower slope is formed with less difference between these supplementary angles. For instance, an example of a relatively high slope is the intersection of a cam profile slope and the rotation axis forming a 1° angle and a 179° angle set of supplementary angles, whereas an example of a relatively low slope is the intersection of a cam profile slope and the rotation axis forming an 89° angle and a 91° angle set of supplementary angles. By way of further example, a "zero" slope is the intersection of a cam profile slope and the rotation axis forming a 90° angle and another 90° angle set of supplementary angles. Generally, higher slope applications of a cam profile have less mechanical advantage, but rotational input (e.g., a rotational input distance), yields greater linear output (e.g., a linear output distance), such that the linear output moves more quickly (e.g., speed). In contrast, lower slope applications of a cam profile have more mechanical advantage, but the same rotational input (e.g., a rotational input distance), yields less linear output (e.g., a linear output distance), such that the linear output moves more slowly (e.g., speed). This relationship between mechanical advantage and speed may be referred to in any of these terms and, in conjunction with high and low slopes, applies to each example of a cam profile discussed herein.

Although closure barrel (510) of the present example is shown as including a single cam profile (530), it should be understood that in other examples closure barrel (510) may include multiple cam profiles (530) to provide a cam profile (530) for each follower pin (384, 386). In some such examples, closure barrel (510) may include two cam profile (530) on opposite sides of closure barrel (510) similar to the configuration of closure barrel (368) and cam profiles (380, 382) discussed above. In other such examples, closure barrel (510) may include two cam profiles (530) staggered along the length of closure barrel (510). Of course, various other suitable configurations of multiple cam profiles (530) will be readily apparent to those of ordinary skill in the art in view of the teachings herein.

Cam profile (530) includes a first end (532) and a second end (550). Both ends define a physical stop for one or more of follower pins (384, 386) or other structures similar to follower pins (384, 386). As will be described in greater detail below, first end (532) is generally configured to engage one or more of follower pins (384, 386) such that jaws (218, 220) may be in a generally open position when one or more of follower pins (384, 386) are positioned at first end (532). Similarly, second end (550) is generally configured to engage one or more of follower pins (384, 386) such that jaws (218, 220) may be in a generally closed position when one or more of follower pins (384, 386) are positioned at second end (550).

Cam profile (530) extends between each end (532, 550) and defines an exponential portion (536). Specifically, exponential portion (536) defines a curve having a continuously decreasing slope from first end (532) to second end (550). In other words, exponential portion (536) defines a maximum slope adjacent to first end (532) and a minimum slope adjacent to second end (550) with the slope continuously decreasing between the maximum and minimum slope. Additionally, in some examples, the decrease of slope between first end (532) and second end (550) may decrease at a varying rate along the length of cam profile (530). For instance, in some examples, the slope may decrease at a relatively rapid rate initially, but then decrease at a slower rate later along cam profile (530).

Figure 18:
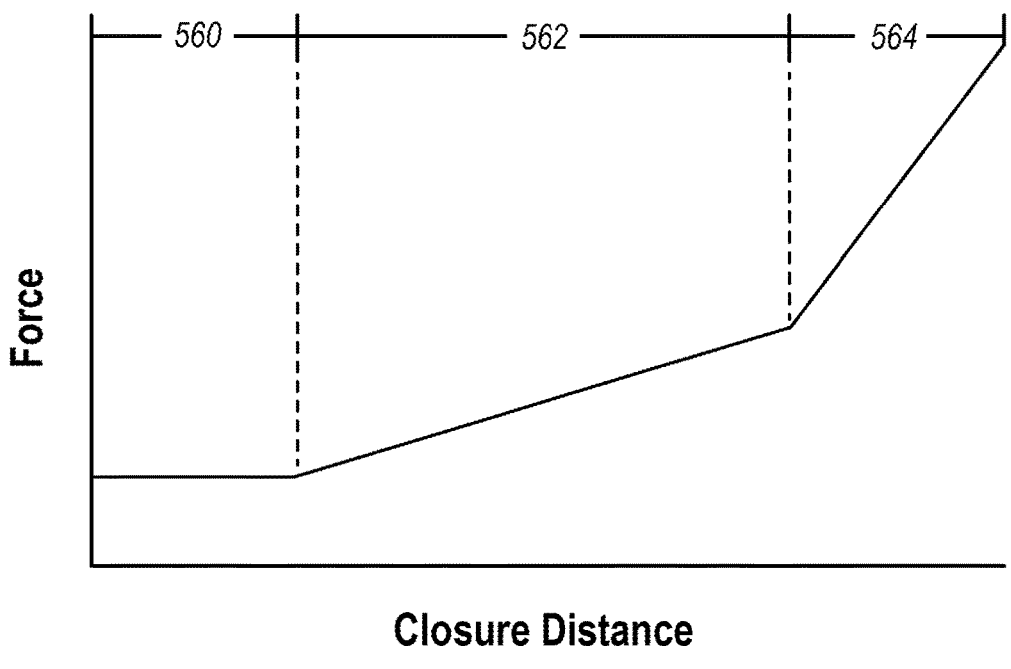
FIG. 18 depicts a plot of a force profile associated with the barrel cam of FIG. 16.

As best seen in FIG. 18, the varying slope of exponential portion (536) may be conceptualized as forming three zones (560, 562, 564) generally corresponding to three separate drive profiles provided by cam profile (530). Although zones (560, 562, 564) are shown in the present example as being bound by discrete lines, it should be understood that zones (560, 562, 564) are not so limited and may be of different lengths or overlap. Indeed, zones (560, 562, 564) are used herein to provide a conceptual framework to describe how various portions of cam profile (530) may function in practice. In addition, although the function of zones (560, 562, 564) are described herein in relation to the function of jaws (218, 220), it should be understood that the same principles may be readily applied to other functions of instrument (210) or other similar instruments.

In a first zone (560) corresponding to a portion of cam profile (530) proximate first end (532), the slope of cam profile (530) is high, such as steep, relative to the rotation axis (531) of closure barrel (510). Consequently, assuming a constant rotary input is applied to driven gear (520), one or more of follower pins (384, 386) may move relatively quickly within first zone (560) relative to the other zones (562, 564) per unit of rotation of closure barrel (510). Yet, the force applied to one or more follower pins (384, 386) is over a shorter distance, so follower pins (384, 386) may be driven with less force per unit of rotation of closure barrel (510). In other words, first zone (560) may provide relatively quick movement of one or more of follower pins (384, 386) (and by extension jaws (218, 220)), but with less force or mechanical advantage. As will be described in greater detail below, the net result of the configuration of first zone (560) is that jaws (218, 220) (or other suitable instrument (210) functions) may be actuated at a relatively fast speed with relatively low force.

In a second zone (562) corresponding to a portion of cam profile (530) proximate to first zone (560) and between first end (532) and second end (550), the slope of cam profile (530) is low, such as less steep, relative to the slope associated with first zone (560). Consequently, assuming a constant rotary input is applied to driven gear (520), one or more of follower pins (384, 386) may move with some relative speed within second zone (562) per unit of rotation of closure barrel (510), but with less speed than in first zone (560). Yet, the force applied to one or more of follower pins (384, 386) is over a greater distance in comparison to first zone (560), so one or more of follower pins (384, 386) may be driven with more force per unit of rotation of closure barrel (510). In other words, second zone (562) may provide a balance between speed of movement of one or more of follower pins (384, 386) and force or mechanical advantage. As will be described in greater detail below, the net result of the configuration of second zone (562) is that jaws (218, 220) (or other suitable instrument (210) functions) may be actuated at a relatively moderate speed with relatively moderate force.

In a third zone (564) corresponding to a portion of cam profile (530) proximate second end (550), the slope of cam profile (530) is relatively shallow relative to the rotation axis (531) of closure barrel (510). Consequently, assuming a constant rotary input is applied to driven gear (520), one or more follower pins (384, 386) may move relatively slowly within third zone (560) relative to first zone (560) and second zone (562) per unit of rotation of closure barrel (510). Yet, the force applied to one or more follower pins (384, 386) is over a larger distance, so one or more follower pins (384, 386) may be driven with greater force per unit of rotation of closure barrel (510). In other words, third zone (564) may provide relatively slow movement of one or more follower pins (384, 386) (and by extension jaws (218, 220)), but with greater force or mechanical advantage. As will be described in greater detail below, the net result of the configuration of third zone (564) is that jaws (218, 220) (or other suitable instrument (210) functions) may be actuated at a relatively slow speed with relatively high force.

In use with instrument (210) described above, closure barrel (510) may be beneficial to provide different operational profiles for different conditions. For instance, during closure of jaws (218, 220) from the open position to the closed position (see FIG. 8B), different speed and/or mechanical advantage profiles may be desirable depending on the conditions generally encountered by jaws (218, 220). For instance, during initial actuation of jaws (218, 220) from the open position, high speed operation with limited force may be desirable because jaws (218, 220) may not initially encounter or manipulate tissue. With respect to closure barrel (510), this condition may correspond to one or more of follower pins (384, 386) being positioned within first zone (560) adjacent to first end (532). The slope(s) of cam profile (530) associated with first zone (560) may therefore drive jaws (218, 220) at a relatively high speed and a relatively low force customized for the conditions generally encountered when initially closing jaws (218, 220).

As jaws (218, 220) close further, jaws (218, 220) may encounter tissue either for the purpose of dissection or for compressing, cutting, and/or sealing tissue. At this stage, at least some increased force may be desirable for the purpose of tissue grasping and/or manipulation. Meanwhile, some speed of closure may still be desirable to improve overall procedure efficiency. With respect to closure barrel (510), this condition may correspond to one or more of follower pins (384, 386) being positioned within second zone (562). The slope(s) of cam profile (530) associated with second zone (562) may therefore drive jaws (218, 220) at a relatively moderate speed and with a moderate force customized for the conditions generally encountered when partially closing jaws (218, 220).

As jaws (218, 220) approach full closure, jaws (218, 220) may begin to compress tissue for the purpose of cutting and/or sealing. At this stage, relatively high force may be desirable for the purpose of compression. Meanwhile, speed of closure may not be as desirable as added force. With respect to closure barrel (510), this condition may correspond to one or more of follow pins (384, 386) being position within third zone (564). The slope(s) of cam profile (530) associate with third zone (564) may therefore drive jaws (218, 220) at a relatively slow speed and with relatively high force customized for the conditions generally encountered when fully closing jaws (218, 220).

B. Closure Barrel with Multiple Operational Sections

Figure 19:
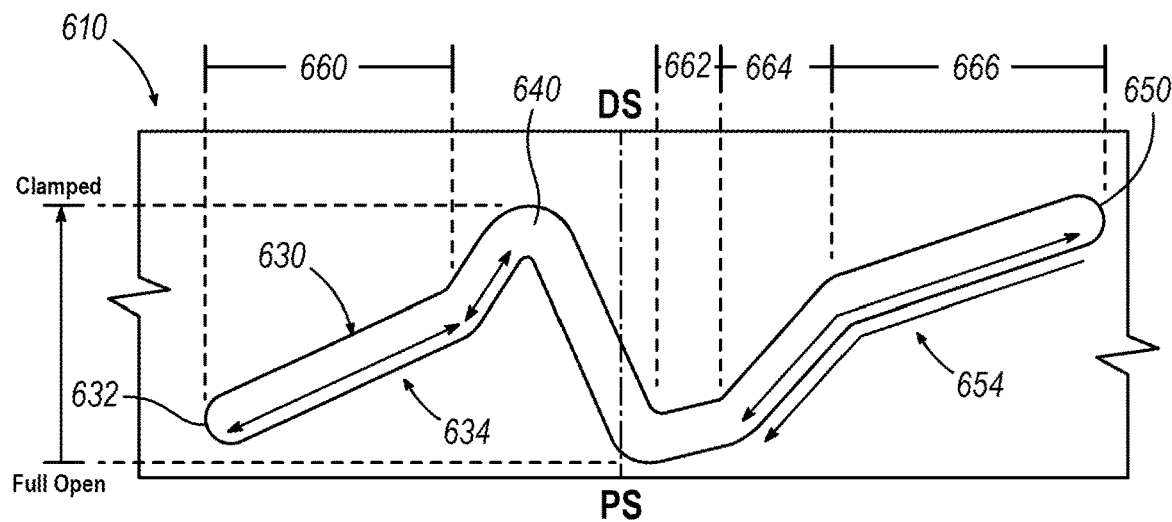
FIG. 19 depicts a schematic view of another exemplary alternative barrel cam for use with the jaw activating mechanism of FIG. 13.

FIG. 19 shows an exemplary alternative closure barrel (610) that may be readily incorporated into instrument (210) in addition to or in lieu of closure barrel (368). Closure barrel (610) of the present example is substantially similar to closure barrel (368) described above in that closure barrel (610) includes a driven gear (not shown) configured to mesh with drive gear (366) (see FIG. 14) or other similar structures to drive rotation of closure barrel (610). Similarly, closure barrel (610) includes a cam profile (630) configured to receive one or both of follower pins (384, 386) to drive actuation of jaws (218, 220) or other similar structures via rotation of closure barrel (610).

As with cam profile (530) discussed above, cam profile (630) of the present example is shown schematically in an "un-rolled" configuration. In this "un-rolled" configuration, cam profile (630) is shown as if closure barrel (610) was cut along a longitudinal rotation axis and laid out flat in a plane. In addition, the orientation of the schematic of FIG. 19 is the opposite as the perspective of closure barrel (510) shown in FIG. 16. Specifically, the distal side (DS) of cam profile (630) is oriented upwardly in the present figures, while the proximal side (PS) of cam profile (630) is oriented downwardly toward the bottom of the present figures.

Although the present example shows a single cam profile (630) schematically, it should be understood that in other examples closure barrel (610) may include multiple cam profiles (630) to provide a cam profile (630) for each follower pin (384, 386). In some such examples, closure barrel (610) may include two cam profiles (630) on opposite sides of closure barrel (610) similar to the configuration of closure barrel (368) and cam profiles (380, 382) discussed above. In other such examples, closure barrel (610) may include two cam profiles (630) staggered along the length of closure barrel (610). This particular configuration may be desirable where a single cam profile (630) extends along the full circumference of closure barrel (610). Of course, various other suitable configurations of multiple cam profiles (630) will be readily apparent to those of ordinary skill in the art in view of the teachings herein.

Cam profile (630) includes a first end (632) and a second end (650). Both ends (632, 650) define a physical stop for one or more of follower pins (384, 386) or other structures similar to follower pins (384, 386). As will be described in greater detail below, first end (632) is generally configured to engage one or more of follower pins (384, 386) such that jaws (218, 220) may be in a generally open position when one or more of follower pins (384, 386) are positioned at first end (632). Similarly, second end (650) is generally configured to engage one or more of follower pins (384, 386) such that jaws (218, 220) may be in a generally closed position when one or more of follower pins (384, 386) are positioned at second end (650).

Cam profile (630) extends between each end (632, 650) and defines two operational sections (634, 654) separated by a functional wall (640). As will be described in greater detail below, operational sections (634, 654) are generally configured to provide different operational profiles tailored for different operations of instrument (210). For instance, in some uses of instrument (210), functions of instrument (210) may be actuated manually by a clinician or other professional using a knob or other input feature configured to manually drive instrument (210). Meanwhile, in other uses of instrument, the same functions may also be driven by drive inputs (10) of robotic system (10). As such, different operational profiles may be desirable to promote ease of use and/or operational efficiency.

As noted above, each operational section (634, 654) is separated by functional wall (640). Functional wall (640) is generally configured to provide a relatively high torque input to move one or more of follower pins (384, 386) through the section of cam profile (630) defining functional wall (640). To facilitate this functionality, functional wall (640) may include a relatively high slope. In some examples, this slope may be greater than other slopes, such as all remaining slopes, associated with cam profile (630). In use, this relatively high torque input may be interpreted as a clinician or other professional as a hard stop during manual operation. However, power from rotary drive outputs (68) of robotic system (28) may be suitable to drive one or more of follower pins (384, 386) through functional wall (640) between each operational section (634, 654). Thus, it should be understood that functional wall (640) may function as a hard stop in some contexts, but function as a portion of cam profile (630) in other contexts depending on the particular drive being applied to instrument (210).

Figure 20:
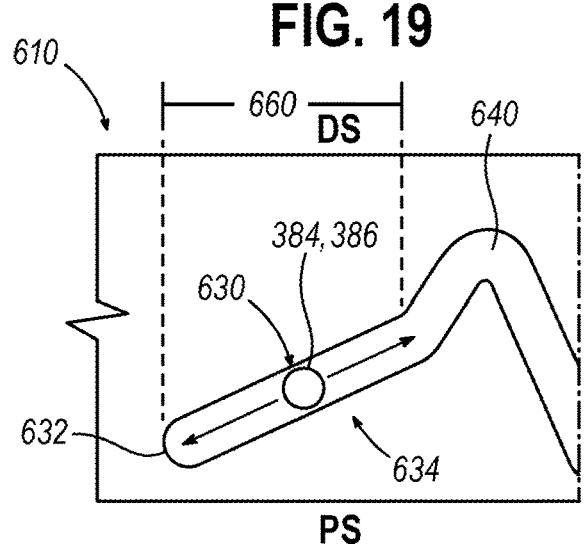
FIG. 20 depicts a detailed schematic view of a first operational section of the barrel cam of FIG. 19.

As can be seen in FIG. 20, cam profile (630) includes a first operational section (634) extending from first end (632). First operational section (634) is generally configured to drive one or more functions of instrument (210) with low power input. As will be described in greater detail below, in some uses such low power input may be desirable for manual operation of instrument (210) by a clinician or other professional.

First operational section (634) defines a first zone (660) having a relatively constant slope that extends from first end (632) to functional wall (640). The particular slope associated with first zone (660) may be relatively low. A relatively low slope may be desirable to permit actuation of one or more functions of instrument (210) with limited power input to closure barrel (610) via driven gear (not shown). Although only a single slope is shown with respect to first zone (660), it should be understood that in other examples varying slopes may be used as similarly described above with respect to cam profile (530). Such varying slopes many be desirable to provide variable speed and/or force profiles as cam profile (630) is used to actuate one or more functions of instrument (210).

Figure 21:
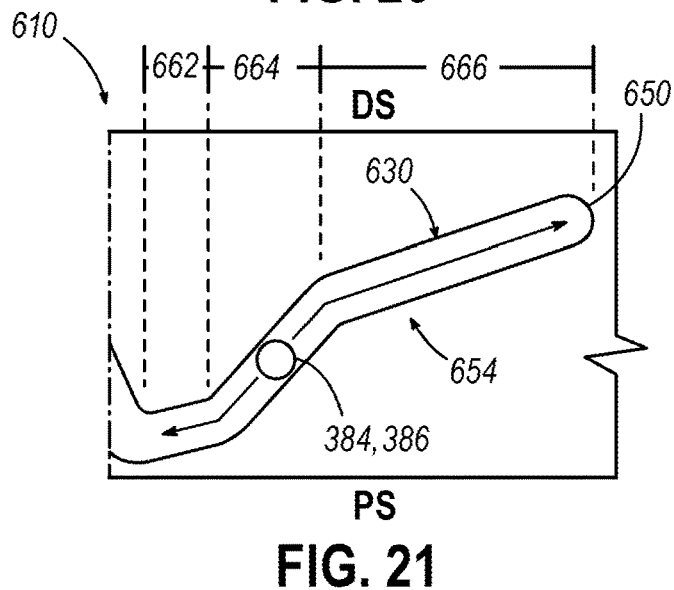
FIG. 21 depicts a detailed schematic view of a second operational section of the barrel cam of FIG. 20.

As can be seen in FIG. 21, cam profile (630) further includes a second operational section (654) extending from functional wall (640) to second end (650). Second operational section (654) is generally configured to drive one or more functions of instrument (210) with power input associated with rotary drive outputs (68) of robotic system (28). As will be described in greater detail below, in some uses such power input may be desirable for operation of instrument (210) by robotic system (28).

Second operational section (654) defines a second zone (662), a third zone (664), and a fourth zone (666). As will be described in greater detail below, zones (662, 664, 666) are generally configured to provide different operational characteristics as one or more functions of instrument (210) are driven by rotary drive outputs (68) of robotic system (28). For instance, second zone (662) defines a relatively low slope extending for a relatively short distance. As will be described in greater detail below, second zone (662) is generally configured to be easily identifiable by control circuitry of robotic system (28). In some instances, this easily identifiable characteristic of second zone (662) may be desirable to identify certain operational conditions such as a bailout condition.

Third zone (664) extends away from second zone (662) towards fourth zone (666) and second end (650). Third zone (664) defines a relatively high slope of cam profile (630). Similarly to the high slopes discussed above with respect to cam profile (530), the relatively high slope of cam profile (630) in third zone (664) is generally configured to provide relatively fast operation of one or more functions of instrument (210), but with relatively low power output. As will be discussed in greater detail below, third zone (664) may correspond to initial closure of jaws (218, 220) where speed of closure may be more desirable than power output.

Fourth zone (666) extends away from third zone (664) and second zone (662) towards second end (650). Fourth zone (666) defines a relatively low slope of cam profile (630). Similarly to the low slopes discussed above with respect to cam profile (530), the relatively low slope of cam profile (630) in fourth zone (666) is generally configured to provide relatively slow operation of one or more functions of instrument (210), but with relatively high power output. As will be discussed in greater detail below, fourth zone (666) may correspond to closure of jaws (218, 220) where engagement with tissue may occur. Thus, higher power output may be more desirable than higher speed of closure at this stage.

In an exemplary use of cam profile (630) with instrument (210), one or more of follower pins (384, 386) may be driven within first operational section (634) or second operational section (654) during different stages of operation. For instance, referring to FIG. 20, one or more of follower pins (384, 386) may be driven within first operational section (634) when instrument (210) is manually actuated by a clinician or other professional using a knob, wheel, crank, or other manual input feature. Manual actuation may be referred to as "off-robot" use in some circumstances. Such off-robot uses may be desirable for certain functions that are more typically performed by a clinician or other professional. By way of example only, one such off-robot uses may correspond to installation of certain disposable components to end effector (214). This may include, for example, installation of a staple cartridge in lower jaw (218), replacement of a used staple cartridge with a new staple cartridge, application of a buttress or other adjunct material to a staple cartridge, and/or other operational uses.

Regardless of the particular purpose of such manual or off-robot actuation, the particular configuration of first operational section (634) is configured to promote ease of use when closure barrel (610) is driven by manual input via driven gear (not shown). For instance, as noted above, first operational section (634) includes first zone (660) having a relatively low slope. This low slope within first zone (660) provides movement of jaws (218, 220) via one or more follower pins (384, 386) with relatively low input power. Consequently, a clinician or other professional may actuate jaws (218, 220) by actuating one or more of follower pins (384, 386) within first zone (660) between first end (632) and functional wall (640).

Both first end (632) and functional wall (640) may be perceived by a clinician or other professional as a hard stop. First end (632) is perceived in this way as first end (632) is configured as an actual hard stop. Meanwhile, as noted above, functional wall (640) defines a relatively high slope. This relatively high slope may rapidly increase the amount of force required to drive one or more of follower pins (384, 386) until a clinician or other professional may not be able to physically drive one or more of follower pins (384, 386). Thus, the clinician or other professional may perceive a hard stop once one or more of follower pins (384, 386) encounter functional wall (640).

In some uses during manual actuation, one or more of follower pins (384, 386) may initially be positioned adjacent to functional wall (640). At this position, jaws (218, 220) may be only partially open rather than being fully closed. This may be generally desirable during manual operation because full closure may not be necessary during operational uses associated with manual actuation. A clinician or other professional may then open jaws (218, 220) further by driving one or more of follower pins (384, 386) along cam profile (630) toward first end (632). Once one or more of follower pins (384, 386) reach first end (632), jaws (218, 220) may be in a fully open configuration.

To transition one or more of follower pins (384, 386) from first operational section (634) to second operational section (654) (or vice versa), one or more follower pins (384, 386) may be driven through functional wall (640). To drive one or more of follower pins (384, 386) through functional wall (640), additional power beyond what is supplied during manual actuation may be required. In the present example, sufficient power may be provided by rotary drive outputs (68) of robotic system (28). Thus, transition of one or more of follower pins (384, 386) between first operational section (634) and second operational section (654) may be facilitated in the present example by rotary drive outputs (68) of robotic system (28). In the present use, transition between first operational section (634) and second operational section (654) may occur during a homing procedure either after initial setup of robotic system (28) or after a clinician or other professional has completed various manual operational steps.

Once one or more of follower pins (384, 386) are driven to second operational section (654), jaws (218, 220) may be actuated robotically by rotary drive outputs (68) of robotic system (28). As such, second operational section (654) is configured to promote use during robotic actuation. Specifically, third zone (664) defines a relatively high slope to drive one or more of follower pins (384, 386) at a relatively fast speed with relatively low output power. This results in jaws (218, 220) being actuated at a relatively fast speed with relatively low output power. In the present example, this stage of actuation corresponds to initial closure of jaws (218, 220). At this stage, tissue is generally not encountered. Thus, speed of closure may be more desirable than power output.

As jaws (218, 220) are closed further, jaws (218, 220) may encounter tissue either for the purpose of dissection or for compressing, cutting, and/or sealing tissue. At this stage, at least some increased force may be desirable for the purpose of tissue grasping and/or manipulation. With respect to cam profile (630), this condition may correspond to one or more of follower pins (384, 386) being positioned within fourth zone (666). As noted above, the slope of cam profile (630) associated with fourth zone (666) may be relatively low to drive jaws (218, 220) at a relatively low speed and with a relatively high force customized for the conditions generally encountered when closing jaws (218, 220).

Jaws (218, 220) may continue to close by driving one or more of follower pins (384, 386) through fourth zone (666) until reaching second end (650). At this stage, jaws (218, 220) may be fully closed. Thus, second end (650) provides a hard stop to prevent undesirable application of stress to jaws (218, 220).

At any stage during operation with second operational section (654), it may be desirable to initiate a bailout procedure. A bailout procedure may be desirable in a variety of circumstances when unexpected operational conditions may be encountered. During such a procedure, one or more of follower pins (384, 386) may be driven manually by a clinician or other professional through second operational section (654) to open jaws (218, 220). For instance, if the bailout procedure is initiated with jaws (218, 220) fully closed and one or more of follower pins (384, 386) adjacent to second end (650), closure barrel (610) may be actuated to drive one or more of follower pins (384, 386) in a reverse direction away from second end (650) through fourth zone (666) and third zone (664) to second zone (662).

Once one or more of follower pins (384, 386) are positioned within second zone (662), initiation of the bailout procedure may be easily detectable. For instance, in some uses, second zone (662) may correspond to an install position where one or more of follower pins (384, 386) may be positioned prior to initiating a homing or initialization procedure. In some uses, detection of initiation of the bailout procedure may be desirable to provide a system lockout.

C. Closure Barrel with Continuous Path Having Multiple Operational Sections

Figure 22:
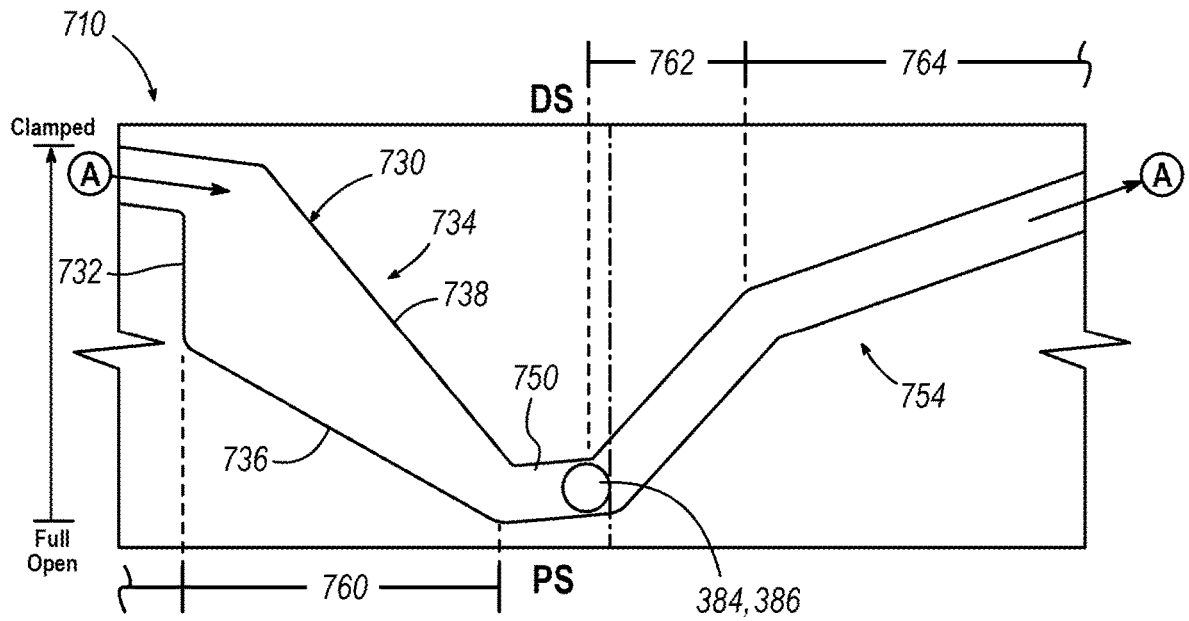
FIG. 22 depicts a schematic view of yet another exemplary alternative barrel cam for use with the jaw activating mechanism of FIG. 13.

FIG. 22 shows an exemplary alternative closure barrel (710) that may be readily incorporated into instrument (210) in addition to or in lieu of closure barrel (368). Closure barrel (710) of the present example is substantially similar to closure barrel (368) described above in that closure barrel (710) includes a driven gear (not shown) configured to mesh with drive gear (366) (see FIG. 14) or other similar structures to drive rotation of closure barrel (710). Similarly, closure barrel (710) includes a cam profile (730) configured to receive one or both of follower pins (384, 386) to drive actuation of jaws (218, 220) or other similar structures via rotation of closure barrel (710).

As with cam profile (530, 630) discussed above, cam profile (730) of the present example is shown schematically in an "un-rolled" configuration. In this "un-rolled" configuration, cam profile (730) is shown as if closure barrel (710) was cut along a longitudinal rotation axis and laid out flat in a plane. In addition, the orientation of the schematic of FIG. 22 is the opposite as the perspective of closure barrel (510) shown in FIG. 16. Specifically, the distal side (DS) of cam profile (730) is oriented upwardly toward the top of the present figures, while the proximal side (PS) of cam profile (730) is oriented downwardly toward the bottom of the present figures.

Although the present example shows a single cam profile (730) schematically, it should be understood that in other examples closure barrel (710) may include multiple cam profiles (730) to provide a cam profile (730) for each follower pin (384, 386). In some such examples, closure barrel (710) may include two cam profiles (730) on opposite sides of closure barrel (710) similar to the configuration of closure barrel (368) and cam profiles (380, 382) discussed above. In other such examples, closure barrel (710) may include two cam profiles (730) staggered along the length of closure barrel (710). This particular configuration may be desirable for a single cam profile (730) extending along the full circumference of closure barrel (710). Of course, various other suitable configurations of multiple cam profiles (730) will be readily apparent to those of ordinary skill in the art in view of the teachings herein.

Unlike cam profiles (530, 630) discussed above, cam profile (730) of the present example is configured to extend around the entire circumference of closure barrel (710). In other words, cam profile (730) of the present example wraps around itself to define a continuous path. As will be described in greater detail below, this continuous path of cam profile (730) may be desirable to provide different operational sections (734, 754) having different operational characteristics during use of cam profile (730) to drive one or more functions of instrument (210). By way of example only, operational sections (734, 754) may be configured to provide operational characteristics tailored for specific functions such as functions powered manually by a clinician or other professional, or functions powered by robotic system (28).

Because cam profile (730) extends entirely around the circumference of closure barrel (710), it should be understood that in some examples certain modifications to closure barrel (710) may be made to provide structural stability to closure barrel (710) while still permitting complete extension of cam profile (730). For instance, in some examples, closure barrel (710) may include structural bridges extending longitudinally (e.g., relative to the axis of rotation) from one side of cam profile (730) to another side of cam profile (730). Such structural bridges may be desirable to hold a distal portion of closure barrel (710) to a proximal portion of closure barrel (710). In addition, or in the alternative, in some examples, cam profile (730) may be configured as an elongate channel cut into the inner diameter of closure barrel (710). Of course, various alternative configurations of closure barrel (710) suitable to provide structural stability in the presence of cam profile (730) will be apparent to those of ordinary skill in the art in view of the teachings herein.

Unlike cam profiles (530, 630) described above, cam profile (730) omits structures similar to first ends (532, 632) and/or second ends (550, 650) given that cam profile (730) extends entirely around the circumference of closure barrel (710) to wrap around itself. Instead, cam profile (730) of the present example includes a hard stop wall (732) and a section transition (750). Hard stop wall (732) defines a physical stop for one or more of follower pins (384, 386) or other structures similar to follower pins (384, 386). As will be described in greater detail below, hard stop wall (732) is generally configured to provide such a physical stop unidirectionally. In other words, hard stop wall (732) functions to provide a physical stop for one or more of follower pins (384, 386) when closure barrel (710) is rotated in one direction, but not another direction. Meanwhile, section transition (750) provides free movement of one or more of follower pins (384, 386). As will be described in greater detail below, section transition (750) is generally configured to provide a transition between operational sections (734, 754) of cam profile (730).

Cam profile (730) extends from hard stop wall (732) through section transition (750) and back to hard stop wall (732) to define a 360° loop with two operational sections (734, 754). As will be described in greater detail below, operational sections (734, 754) are generally configured to provide different operational profiles tailored for different operations of instrument (210). For instance, in some uses of instrument (210), functions of instrument (210) may be actuated manually by a clinician or other professional using a knob or other input feature configured to manually drive instrument (210). Meanwhile, in other uses of instrument, the same functions may also be driven by drive inputs (10) of robotic system (10). As such, different operational profiles may be desirable to promote ease of use and/or operational efficiency.

Figure 23:
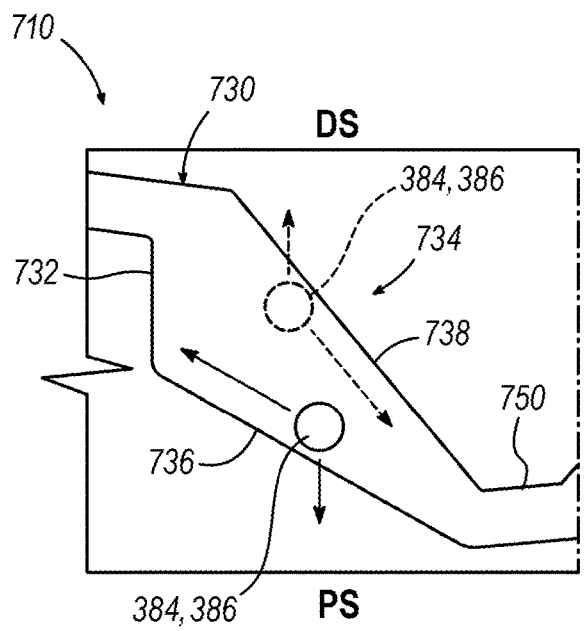
FIG. 23 depicts a detailed schematic view of a first operational section of the barrel cam of FIG. 22.

As can be seen in FIG. 23, cam profile (730) includes a first operational section (734) extending from hard stop wall (732). First operational section (734) is generally configured to drive one or more functions of instrument (210) with low power input. As will be described in greater detail below, in some uses such low power input may be desirable for manual operation of instrument (210) by a clinician or other professional.

First operational section (734) defines a first zone (760) that includes a relatively constant slope that extends from hard stop wall (732) to section transition (750). In addition, first operational section (734) defines a closure surface (736) and an opening surface (738) opposite of closure surface (736). Closure surface (736) and opening surface (738) each include slopes tailored for certain stages of operation. For instance, the particular slope associated with closure surface (736) may be relatively low. A relatively low slope may be desirable to permit actuation of one or more functions of instrument (210) with limited power input to closure barrel (710) via driven gear (not shown). Meanwhile, the particular slope associated with opening surface (738) may be relatively high. A relatively high slope may be desirable to permit relatively fast actuation of one or more functions of instrument (210) while requiring additional power input to closure barrel (710) via driven gear (not shown). Although closure surface (736) and opening surface (738) are both shown as including only a single slope, respectively, it should be understood that in other examples varying slopes may be used as similarly described above with respect to cam profile (530). Such varying slopes many be desirable to provide variable speed and/or force profiles as cam profile (730) is used to actuate one or more functions of instrument (210).

As noted above, hard stop wall (732) is positioned at one end of first zone (760). Specifically, hard stop wall (732) extends axially in a distal direction from closure surface (736). The particular position of hard stop wall (732) along the length of closure surface (736) corresponds to an intermediate position with respect to actuation of instrument (210). As will be described in greater detail below, this intermediate position in use may correspond to jaws (218, 220) being partially, but not fully closed. In this configuration, hard stop wall (732) is configured to act as a hard stop to physically stop movement of one or more of follower pins (384, 386) when driven using closure surface (736). Yet, hard stop wall (732) terminates before reaching opening surface (738). Thus, hard stop wall (732) may not act as a physical stop for one or more follower pins (384, 386) when driven using opening surface (738).

Figure 24:
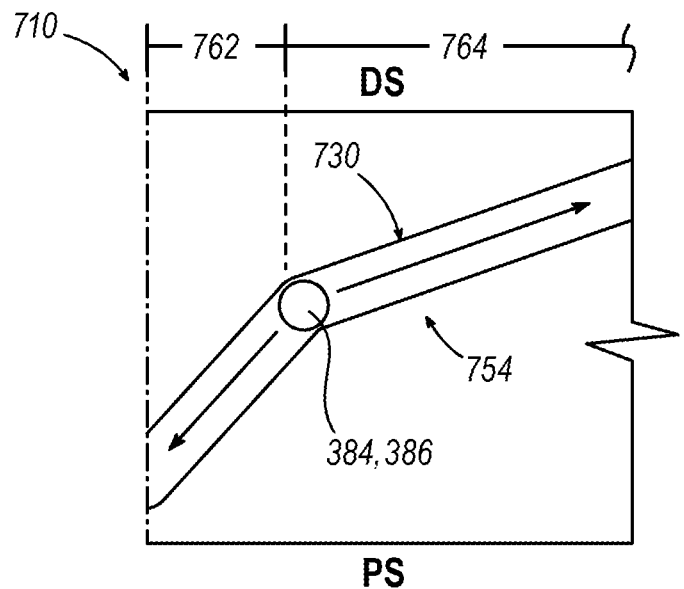
FIG. 24 depicts a detailed schematic view of a second operational section of the barrel cam of FIG. 22.

As can be seen in FIG. 24, cam profile (730) further includes a second operational section (754) extending from section transition (750) to hard stop wall (732). Second operational section (754) is generally configured to drive one or more functions of instrument (210) with power input associated with rotary drive outputs (68) of robotic system (28). As will be described in greater detail below, in some uses such power input may be desirable for operation of instrument (210) by robotic system (28).

Second operational section (754) defines a second zone (762) and a third zone (764). As will be described in greater detail below, zones (762, 764) are generally configured to provide different operational characteristics as one or more functions of instrument (210) are driven by rotary drive outputs (68) of robotic system (28). For instance, second zone (762) extends away from section transition (750) and defines a relatively high slope of cam profile (730). Similarly to the high slopes discussed above with respect to cam profile (530), the relatively high slope of cam profile (730) in second zone (762) is generally configured to provide relatively fast operation of one or more functions of instrument (210), but with relatively low power output. As will be discussed in greater detail below, second zone (762) may correspond to initial closure of jaws (218, 220) where speed of closure may be more desirable than power output.

Third zone (764) extends away from second zone (762) and towards hard stop wall (732) before intersecting with first zone (760). Third zone (764) defines a relatively low slope of cam profile (730). Similarly to the low slopes discussed above with respect to cam profile (530), the relatively low slope of cam profile (730) in third zone (764) is generally configured to provide relatively slow operation of one or more functions of instrument (210), but with relatively high power output. As will be discussed in greater detail below, third zone (764) may correspond to closure of jaws (218, 220) where engagement with tissue may occur. Thus, power output may be more desirable than speed of closure at this stage.

In an exemplary use of cam profile (730) with instrument (210), one or more of follower pins (384, 386) may be driven within first operational section (734) or second operational section (754) during different stages of operation. For instance, referring to FIG. 23, one or more of follower pins (384, 386) may be driven within first operational section (734) when instrument (210) is manually actuated by a clinician or other professional using a knob, wheel, crank, or other manual input feature. Manual actuation may be referred to as "off-robot" use in some circumstances. Such off-robot uses may be desirable for certain functions that are more typically performed by a clinician or other professional. By way of example only, one such off-robot uses may correspond to installation of certain disposable components on end effector (214). This may include, for example, installation of a staple cartridge in lower jaw (218), replacement of a used staple cartridge with a new staple cartridge, application of a buttress or other adjunct material to a staple cartridge, and/or other operational uses.

Regardless of the particular purpose of such manual or off-robot actuation, the particular configuration of first operational section (734) is configured to promote ease of use when closure barrel (710) is driven by manual input via driven gear (not shown). For instance, as noted above, first operational section (734) includes first zone (760) having closure surface (736), which includes a relatively low slope. This low slope of closure surface (736) provides movement of jaws (218, 220) via one or more follower pins (384, 386) with relatively low input power. Consequently, a clinician or other professional may actuate jaws (218, 220) by actuating one or more of follower pins (384, 386) within first zone (660) along closure surface (736).

During use in first zone (760) under manual or off-robot actuation, jaws (218, 220) may be driven from a fully open configuration to a partially closed configuration. This closure of jaws (218, 220) results in a distally oriented force being applied to one or more of follower pins (384, 386) by closure tube (304). This distally oriented force maintains contact between one or more of follower pins (384, 386) and closure surface (736) as closure barrel (710) is rotated to drive one or more of follower pins (384, 386) from section transition (750) to hard stop wall (732). This may continue until one or more of follower pins (384, 386) contact hard stop wall (732), preventing further closure of jaws (218, 220). Optimally, contact between one or more of follower pins (384, 386) and hard stop wall (732) may be used to provide a tactile signal to a clinician or other professional such as signaling proper installation of a buttress or other adjunct material. At this stage, jaws (218, 220) may be partially closed to promote various manual operations such replacement of a used staple cartridge with a new staple cartridge, application of a buttress or other adjunct material to a staple cartridge, installation of end effector (214) into components such as trocars, and/or other operational uses.

Once certain manual operations are complete, one or more of follower pins (384, 386) may be returned to section transition (750) by reversing the direction of rotation of closure barrel (710) to drive one or more of follower pins (384, 386) in an opposite direction towards section transition (750). Such rotation of closure barrel (710) may be controlled either manually or robotically using robotic system (28). Regardless, during such reverse rotation, one or more of follower pins (384, 386) may shift from closure surface (736) to opening surface (738) to drive jaws (218, 220) from the partially closed configuration to the fully open configuration. As noted above, opening surface (738) includes a relatively high slope, so jaws (218, 220) may open relatively quickly while requiring additional input in comparison to closure using closure surface (736).

Once one or more of follower pins (384, 386) are driven back to section transition (750), further rotation of closure barrel (710) may drive one or more of follower pins (384, 386) into second operational section (754). Once driven to second operational section (754), jaws (218, 220) may be actuated robotically by rotary drive outputs (68) of robotic system (28). As such, second operational section (754) is configured to promote use during robotic actuation. Specifically, second zone (762) defines a relatively high slope to drive one or more of follower pins (384, 386) at a relatively fast speed with relatively low output power. This results in jaws (218, 220) being actuated at a relatively fast speed with relatively low output power. In the present example, this stage of actuation corresponds to initial closure of jaws (218, 220). At this stage, tissue is generally not encountered. Thus, speed of closure may be more desirable than power output.

As jaws (218, 220) are closed further, jaws (218, 220) may encounter tissue either for the purpose of dissection or for compressing, cutting, and/or sealing tissue. At this stage, at least some increased force may be desirable for the purpose of tissue grasping and/or manipulation. With respect to cam profile (730), this condition may correspond to one or more of follower pins (384, 386) being positioned within third zone (764). As noted above, the slope of cam profile (730) associated with third zone (764) may be relatively low to drive jaws (218, 220) at a relatively low speed and with a relatively high force customized for the conditions generally encountered when closing jaws (218, 220).

Jaws (218, 220) may continue to close by driving one or more of follower pins (384, 386) through third zone (764). At this stage, a software stop may be used to prevent continued rotation of closure barrel (710) to drive one or more follower pins (384, 386) from third zone (764) into first zone (760). Specifically, control circuitry of robotic system (28) may be used to extrapolate the position of follower one or more of follower pins (384, 386) within cam profile (730) using the position of rotary drive inputs (68). Thus, control circuitry of robotic system (28) may be used to provide a functional hard stop once jaws (218, 220) may be fully closed.

Figure 25:
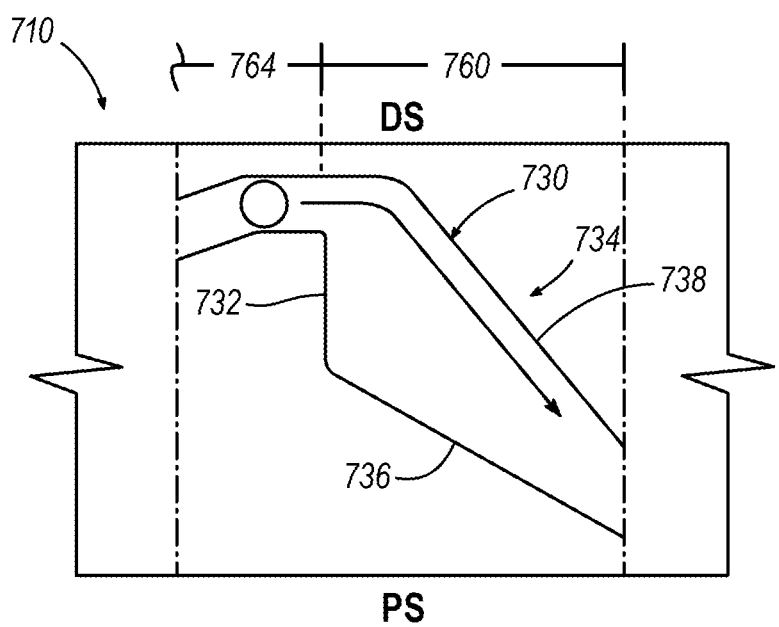
FIG. 25 depicts another detailed schematic view of the first operational section of the barrel cam of FIG. 22, with the first operational section being used in a bailout procedure.

At any stage during operation with second operational section (754), it may be desirable to initiate a bailout procedure. A bailout procedure may be desirable in a variety of circumstances when unexpected operational conditions may be encountered. During such a procedure, one or more of follower pins (384, 386) may be driven manually by a clinician or other professional through second operational section (754) to open jaws (218, 220). For instance, as best seen in FIG. 25, if the bailout procedure is initiated with jaws (218, 220) fully closed and one or more of follower pins (384, 386) within third zone (764), closure barrel (710) may be actuated to drive one or more of follower pins (384, 386) in the same direction immediately from third zone (764) back to first zone (760). This particular transition may be generally desirable because the manual actuation would be familiar to a clinician or other professional because the same direction of rotation used for opening of jaws (218, 220) would be used during the bailout procedure as used during manual operation described above.

Once one or more of follower pins (384, 386) are positioned within first zone (760) a clinician or other professional may then continue manual actuation of closure barrel (710) to drive one or more of follower pins (384, 386) along opening surface (738). Such actuation may be continued until jaws (218, 220) are returned to the fully open configuration.

Figure 26:
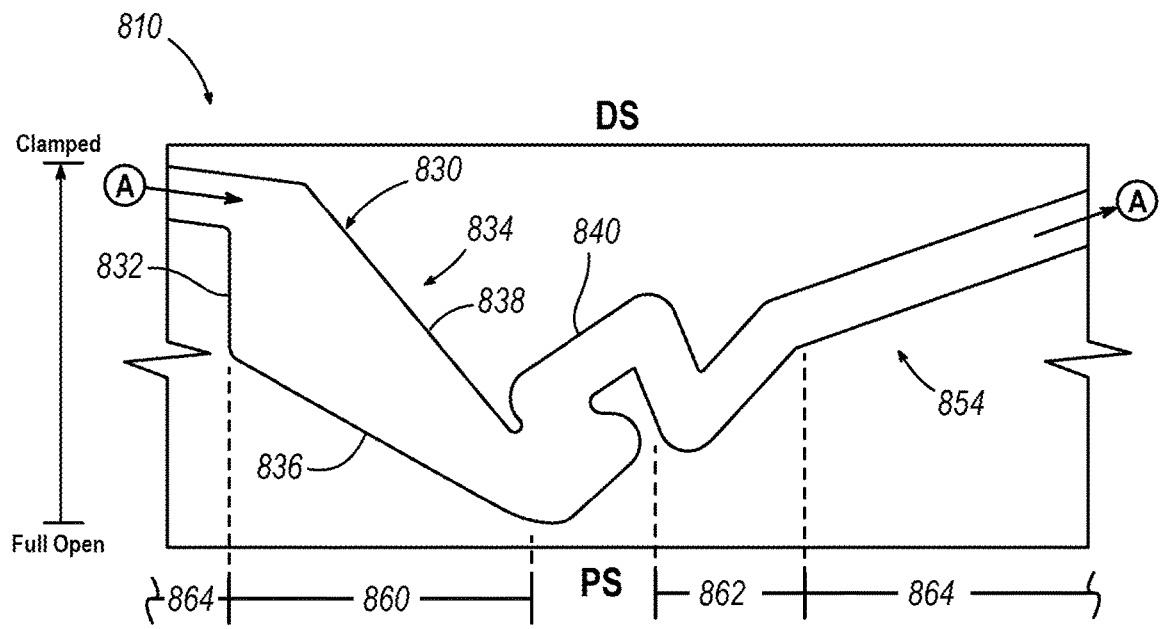
FIG. 26 depicts a schematic view of still another exemplary alternative barrel cam for use with the jaw activating mechanism of FIG. 13.

FIG. 26 shows an exemplary alternative closure barrel (810) that is substantially similar to closure barrel (710) described above. For instance, like with closure barrel (710), closure barrel (810) of the present example includes a cam path (830) with operational sections (834, 854) configured for both manual and robotic uses. As with cam profile (730) discussed above, cam profile (830) of the present example includes a first operational section (834) configured for manual use and a second operational section (854) configured for robotic use. As with first operational section (734) and second operation section (754) described above, first operational section (834) and second operational section (854) of the present example intersect with each other such that cam path (830) extends around the circumference of closure barrel (810) 360°.

First operational section (834) is substantially similar to first operational section (734) described above. For instance, as with first operational section (734), first operational section (834) of the present example includes a hard stop wall (832), a closure surface (836) extending from the hard stop wall (832), and an opening surface (838) opposite closure surface (836). Hard stop wall (832) is substantially similar to hard stop wall (732) such that hard stop wall (832) functions as a hard stop when one or more of follower pins (384, 386) are driven using closure surface (836). Similarly, closure surface (836) is generally configured to drive closure of jaws (218, 220) using one or more of follower pins (384, 386), while opening surface (838) is generally configured to drive opening of jaws (218, 220) using one or more of follower pins (384, 386). Thus, hard stop wall (832), closure surface (836), and opening surface (838) together define a first zone (860), similar to first zone (760) described above, tailored for manual operation of closure barrel (810).

Second operational section (854) is likewise substantially similar to second operational section (754) described above. For instance, as with second operational section (754), second operational section (854) of the present example defines a second zone (862) and a third zone (864) with slopes of cam profile (830) corresponding to a particular robotically controlled operational stage. For instance, second zone (862) is substantially similar to second zone (762) in that second zone (862) is configured with a relatively high slope to drive closure of jaws (218, 220) via one or more of follower pins (384, 386) at a relatively fast speed with relatively low power output. Similarly, third zone (864) is substantially similar to third zone (764) in that third zone (864) is configured with a relatively low slope to drive closure of jaws (218, 220) via one or more of follower pins (384, 386) at a relatively slow speed with relatively high power output. Third zone (864) is also substantially similar to third zone (764) in that third zone (864) intersects with first zone (860) to promote ease of use during a bailout procedure.

Unlike closure barrel (710) described above, closure barrel (810) of the present example includes a functional wall (840) between first operational section (834) and second operational section (854). Functional wall (840) is generally configured to provide a relatively high torque input to move one or more of follower pins (384, 386) through the section of cam profile (830) defining functional wall (840). For instance, in the present example, functional wall includes a relatively high slope or an undercut, indentation, pit or other structure configured to catch one or more of follower pins (384, 386). In use, this relatively high torque input may be interpreted by a clinician or other professional as a hard stop during manual operation. However, power from rotary drive outputs (68) of robotic system (28) may be suitable to drive one or more of follower pins (384, 386) through functional wall (840) between each operational section (834, 854). Alternatively, in some examples, closure barrel (810) and/or one or more follower pins (384, 386) may be associated with a cam shifter configured to shift one or more of follower pins (384, 386) past functional wall (840). Thus, it should be understood that functional wall (840) may function as a hard stop in some contexts, but function as a portion of cam profile (830) in other contexts depending on the particular drive being applied to instrument (210).

In use, closure barrel (810) functions substantially similarly to closure barrel (710) described above. For instance, closure barrel (810) may be initially used with manual input by a clinician or other professional. As noted above, manual input may be associated with first operational section (834). This may include driving one or more of follower pins (384, 386) through first zone (860) until reaching hard stop wall (832) to partially close jaws (218, 220). Closure barrel (810) may then be reversed to open jaws (218, 220) manually.

Use of closure barrel (810) with robotic operation may also be substantially similar to such use described above with respect to closure barrel (710). For instance, rotary drive outputs (68) of robotic system (28) may drive one or more of follower pins (384, 386) initially though second zone (862). As noted above, second zone (862) includes a relatively high slope to provide relatively fast actuation of jaws (218, 220) via one or more of follower pins (384, 386). After second zone (862), one or more of follower pins (384, 386) may be driven through third zone (864). As noted above, third zone (864) includes a relatively low slope to provide relatively high-powered actuation of jaws (218, 220) via one or more of follower pins (384, 386).

Unlike the use of closure barrel (710) described above, use of closure barrel (810) may include some differences at the transition between first operational section (834) and second operational section (854). For instance, as noted above, cam profile (830) of the present example includes functional wall (840). As such, functional wall (840) may be interpreted as a hard stop during manual actuation due to the torque required to drive one or more of follower pins (384, 386) through functional wall (840). Thus, in use, functional wall (840) may be desirable to prevent a clinician or other professional from inadvertently driving one or more of follower pins (384, 386) into second operational section (854). Yet, rotary drive outputs (68) of robotic system (28) may still be readily able to drive one or more of follower pins (384, 386) through functional wall (840) to facilitate the transition of one or more of follower pins (384, 386) from first operational section (834) to second operational section (854) (and vice versa). Alternatively, in some examples, closure barrel (810) and/or one or more of follower pins (384, 386) may be associated with a cam shifter to facilitate movement of one or more of follower pins (384, 386) through functional wall (840).

D. Closure Barrel with Continuous Path Having Forked Operational Section

Figure 27:
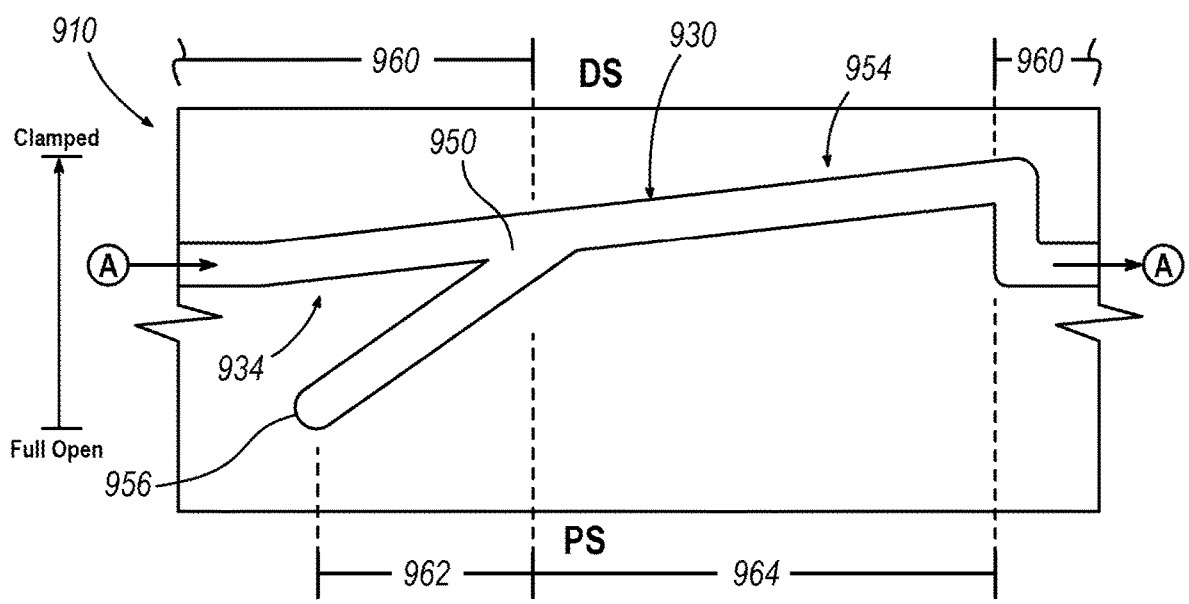
FIG. 27 depicts a schematic view of still another exemplary alternative barrel cam for use with the jaw activating mechanism of FIG. 13.

FIG. 27 shows an exemplary alternative closure barrel (910) that may be readily incorporated into instrument (210) in addition to or in lieu of closure barrel (368). Closure barrel (910) of the present example is substantially similar to closure barrel (368) described above in that closure barrel (910) includes a driven gear (not shown) configured to mesh with drive gear (366) (see FIG. 14) or other similar structures to drive rotation of closure barrel (910). Similarly, closure barrel (910) includes a cam profile (930) configured to receive one or both of follower pins (384, 386) or other cam follower mechanisms to drive actuation of jaws (218, 220) or other similar structures via rotation of closure barrel (910).

As with cam profile (530, 630, 730, 830) described above, cam profile (930) of the present example is shown schematically in an "un-rolled" configuration. In this "un-rolled" configuration, cam profile (930) is shown as if closure barrel (910) was cut along a longitudinal rotation axis and laid out flat in a plane. In addition, the orientation of the schematic of FIG. 27 is the opposite as the perspective of closure barrel (510) shown in FIG. 16. Specifically, the distal side (DS) of cam profile (930) is oriented upwardly toward the top of the present figures, while the proximal side (PS) of cam profile (930) is oriented downwardly toward the bottom of the present figures.

Although the present example shows a single cam profile (930) schematically, it should be understood that in other examples closure barrel (910) may include multiple cam profiles (930) to provide a cam profile (930) for each follower pin (384, 386) or other cam follower mechanisms. In some such examples, closure barrel (910) may include two cam profiles (930) on opposite sides of closure barrel (910) similar to the configuration of closure barrel (368) and cam profiles (380, 382) discussed above. In other such examples, closure barrel (910) may include two cam profiles (930) staggered along the length of closure barrel (910). This particular configuration may be desirable for a single cam profile (930) extending along the full circumference of closure barrel (910). Of course, various other suitable configurations of multiple cam profiles (930) will be readily apparent to those of ordinary skill in the art in view of the teachings herein.

Unlike cam profiles (530, 630) discussed above, cam profile (930) of the present example is configured to extend around the entire circumference of closure barrel (910). In other words, cam profile (930) of the present example wraps around itself to define a continuous path. As will be described in greater detail below, this continuous path of cam profile (930) may be desirable to provide different operational sections (934, 954) having different operational characteristics during use of cam profile (930) to drive one or more functions of instrument (210). By way of example only, operational sections (934, 954) may be configured to provide operational characteristics tailored for specific functions such as functions powered manually by a clinician or other professional, or functions powered by robotic system (28).

Because cam profile (930) extends entirely around the circumference of closure barrel (910), it should be understood that in some examples certain modifications to closure barrel (910) may be made to provide structural stability to closure barrel (910) while still permitting complete extension of cam profile (930). For instance, in some examples, closure barrel (910) may include structural bridges extending longitudinally (e.g., relative to the axis of rotation) from one side of cam profile (930) to another side of cam profile (930). Such structural bridges may be desirable to hold a distal portion of closure barrel (910) to a proximal portion of closure barrel (910). In addition, or in the alternative, in some examples, cam profile (930) may be configured as an elongate channel cut into the inner diameter of closure barrel (910). Of course, various alternative configurations of closure barrel (910) suitable to provide structural stability in the presence of cam profile (930) will be apparent to those of ordinary skill in the art in view of the teachings herein.

Unlike cam profiles (530, 630) described above, cam profile (930) omits structures similar to first ends (532, 632) and/or second ends (550, 650). As noted above, cam profile (930) extends entirely around the circumference of closure barrel (910) to wrap around itself. Thus, structures similar to first ends (532, 632) and/or second ends (550, 650) are unnecessary in the present example. Instead, cam profile (930) of the present example includes a hard stop wall (932) and a fork (950). Hard stop wall (932) defines a physical stop for one or more of follower pins (384, 386) or other structures similar to follower pins (384, 386). As will be described in greater detail below, hard stop wall (932) is generally configured to provide such a physical stop unidirectionally. In other words, hard stop wall (932) functions to provide a physical stop for one or more of follower pins (384, 386) when closure barrel (910) is rotated in one direction, but not another direction. To facilitate such functionality, hard stop wall (932) of the present example defines a generally Z or L-shaped pattern.

Fork (950) is positioned at the intersection of two portions of cam profile (930). As will be described in greater detail below, fork (950) is generally configured to provide one-way access to certain portions of cam profile (930). In some examples, this functionality may be desirable to promote sequential operation of cam profile (930) that prevents certain functions until other functions are completed. Fork (950) may also be desirable to permit portions of cam profile (930) to be positioned within the same radial section of closure barrel (910) to permit a longer cam profile (930) without having to increase the circumference of closure barrel (910). Fork (950) of the present example defines a generally Y-shaped pattern due to two portions of cam profile (930) intersecting at different angles. Although fork (950) is shown in the present example as having a specific shape, it should be understood that in other examples various alternative shapes may be used.

Cam profile (930) extends from hard stop wall (932) through fork (950) and back to hard stop wall (932) to define a 360° loop with two operational sections (934, 954). As will be described in greater detail below, operational sections (934, 954) are generally configured to provide different operational profiles tailored for different operations of instrument (210). For instance, in some uses of instrument (210), functions of instrument (210) may be actuated manually by a clinician or other professional using a knob or other input feature configured to manually drive instrument (210). Meanwhile, in other uses of instrument, the same functions may also be driven by drive inputs (10) of robotic system (10). As such, different operational profiles may be desirable to promote ease of use and/or operational efficiency.

Cam profile (930) includes a first operational section (934) extending from hard stop wall (932) and a second operational section (954) extending from a first end (956) through fork (950) to hard stop wall (932). First operational section (934) is generally configured to drive one or more functions of instrument (210) with low power input. As will be described in greater detail below, in some uses such low power input may be desirable for manual operation of instrument (210) by a clinician or other professional.

First operational section (934) defines a first zone (960) that includes a relatively constant slope that extends from hard stop wall (932) to fork (950). The particular slope associated with first zone (936) may be relatively low. As noted above, a relatively low slope may be desirable to permit actuation of one or more functions of instrument (210) with limited power input to closure barrel (910) via driven gear (not shown). Although first zone (960) is shown as including only a single slope, it should be understood that in other examples varying slopes may be used as similarly described above with respect to cam profile (530). Such varying slopes many be desirable to provide variable speed and/or force profiles as cam profile (930) is used to actuate one or more functions of instrument (210).

As noted above, hard stop wall (932) is positioned at one end of first zone (960). Specifically, hard stop wall (932) extends axially in a distal direction. The particular position of hard stop wall (932) along the length of first zone (960) corresponds to an intermediate position with respect to actuation of instrument (210). As will be described in greater detail below, this intermediate position in use may correspond to jaws (218, 220) being partially, but not fully closed. In this configuration, hard stop wall (932) is configured to act as a hard stop to physically stop movement of one or more of follower pins (384, 386) or other structures when driven using first zone (960). Yet, hard stop wall (932) extends distally away from first zone (960) and then bends about 90° to intersect with second operational section (954). Thus, hard stop wall (932) may not act as a physical stop for one or more follower pins (384, 386) when driven in an opposite direction from second operational section (954) toward first zone (960) of first operational section (934).

As noted above, cam profile (930) further includes a second operational section (954) extending from first end (956) through fork (950) to hard stop wall (932). Second operational section (954) is generally configured to drive one or more functions of instrument (210) with power input associated with rotary drive outputs (68) of robotic system (28). As will be described in greater detail below, in some uses such power input may be desirable for operation of instrument (210) by robotic system (28).

Second operational section (954) defines a second zone (962) and a third zone (964). As will be described in greater detail below, zones (962, 964) are generally configured to provide different operational characteristics as one or more functions of instrument (210) are driven by rotary drive outputs (68) of robotic system (28). For instance, second zone (962) extends away from first end (956) and defines a relatively high slope of cam profile (930). Similarly to the high slopes discussed above with respect to cam profile (530), the relatively high slope of cam profile (930) in second zone (962) is generally configured to provide relatively fast operation of one or more functions of instrument (210), but with relatively low power output. As will be discussed in greater detail below, second zone (962) may correspond to initial closure of jaws (218, 220) where speed of closure may be more desirable than power output.

Third zone (964) extends away from second zone (962) and fork (950) towards hard stop wall (932) before intersecting with first zone (960). Third zone (964) defines a relatively low slope of cam profile (930). Similarly to the low slopes discussed above with respect to cam profile (530), the relatively low slope of cam profile (930) in third zone (964) is generally configured to provide relatively slow operation of one or more functions of instrument (210), but with relatively high power output. As will be discussed in greater detail below, third zone (964) may correspond to closure of jaws (218, 220) where engagement with tissue may occur. Thus, power output may be more desirable than speed of closure at this stage.

Figure 28:
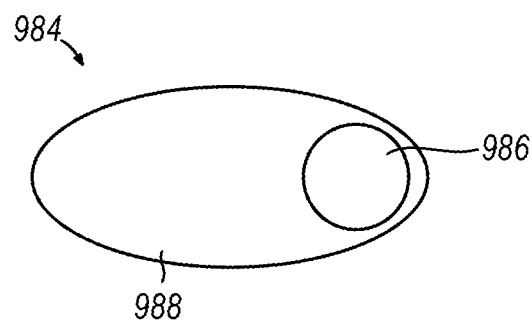
FIG. 28 depicts a side elevational view of an exemplary alternative follower pin for use with the jaw activating mechanism of FIG. 13.

FIG. 28 shows an exemplary alternative follower pin (984) that may be used with closure barrel (910) in instrument (210) to drive jaws (218, 220) in lieu of one or more of follower pins (384, 386). Follower pin (984) may be desirable for use with closure barrel (910) of the present example to provide more predictable operation in connection with fork (950). For instance, as noted above, it may be desirable to control access to portions of cam profile (930) to promote sequential operation.

Follower pin (984) of the present example includes a drive pin (986) and a traveler (988). Drive pin (986) is generally configured to be moved by movement of traveler (988) through cam profile (930). Similarly to follower pins (384, 386) described above, drive pin (986) may be in communication with one or more components of instrument (210) such as closure tube (304) to drive actuation of jaws (218, 220).

Traveler (988) defines an oval, elliptical and/or oblong shape that is generally configured to provide engagement with cam profile (930). Traveler (988) is connected with drive pin (986) at an off-center location. In other words, traveler (988) is connected with drive pin (986) proximate a vertex of traveler (988). As will be described in greater detail below, this configuration is generally desirable to permit movement of traveler (988) relative to drive pin (986).

Traveler (988) is configured to pivot relative to drive pin (986). This pivoting feature may be desirable to provide alignment between a longitudinal rotation axis of traveler (988) and the particular slope of cam profile (930). In some examples, pivoting of traveler (988) may be facilitated by a spring or other resilient feature. As will be described in greater detail, such a spring or other resilient feature may be biased in a single direction to permit certain unidirectional functionality in connection with fork (950).

In an exemplary use of cam profile (930) with instrument (210), follower pin (984) may be driven within first operational section (934) or second operational section (954) during different stages of operation. For instance, referring to FIG. 29, follower pin (984) may be driven within first operational section (934) when instrument (210) is manually actuated by a clinician or other professional using a knob, wheel, crank, or other manual input feature. Manual actuation may be referred to as "off-robot" use in some circumstances. Such off-robot uses may be desirable for certain functions that are more typically performed by a clinician or other professional. By way of example only, one such off-robot uses may correspond to installation of a staple cartridge in lower jaw (218), replacement of a used staple cartridge with a new staple cartridge, application of a buttress or other adjunct material to a staple cartridge, and/or other operational uses.

Regardless of the particular purpose of such manual or off-robot actuation, the particular configuration of first operational section (934) is configured to promote ease of use when closure barrel (910) is driven by manual input via driven gear (not shown). For instance, as noted above, first operational section (934) includes first zone (960) having a relatively low slope. This low slope of first zone (960) provides movement of jaws (218, 220) via follower pin (984) with relatively low input power. Consequently, a clinician or other professional may actuate jaws (218, 220) by actuating follower pin (984) within first zone (960).

Figure 29:
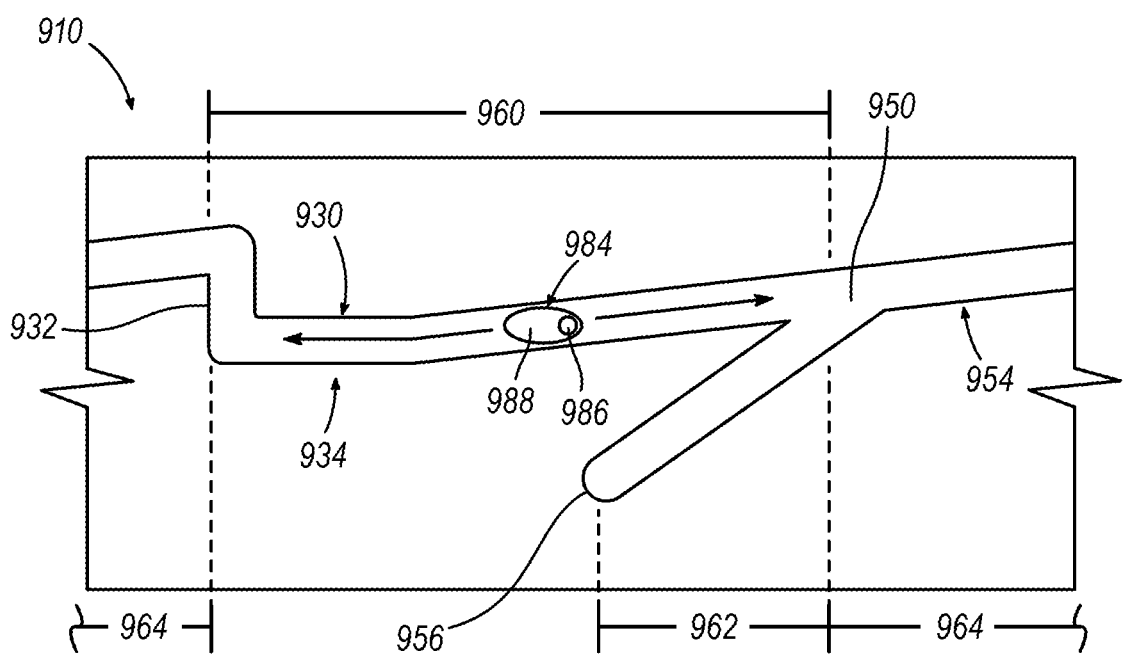
FIG. 29 depicts a schematic view of still another exemplary alternative barrel cam for use with the jaw activating mechanism of FIG. 13.
Figure 30:
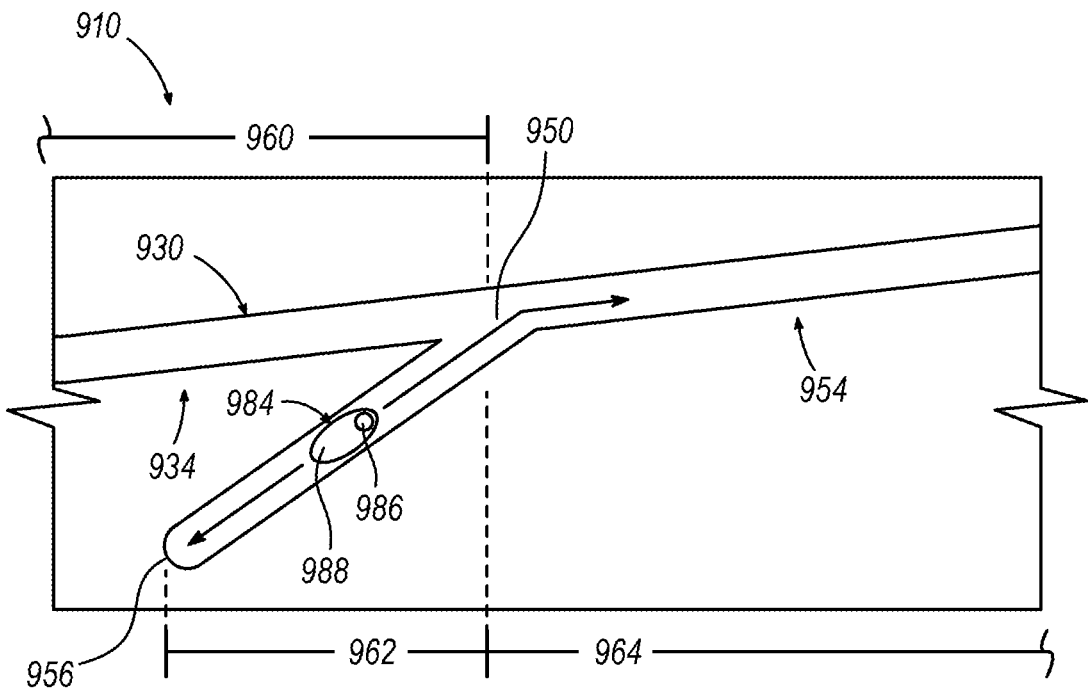
FIG. 30 depicts a detailed schematic view of the barrel cam of FIG. 29, with the follower pin of FIG. 28 engaged with a second operational section of the barrel cam.

With respect to FIGS. 29 and 30, during use in first zone (960) under manual or off-robot actuation, jaws (218, 220) may be driven from a partially open configuration to a partially closed configuration. A clinician or other professional may drive jaws (218, 220) between the partially open configuration and the partially closed configuration as desired to perform various manual operations such as replacement of a used staple cartridge with a new staple cartridge, application of a buttress or other adjunct material to a staple cartridge, installation of end effector (214) into components such as trocars, and/or other operational uses. Contact between follower pin (984) and hard stop wall (932) may be used to provide a tactile signal to a clinician or other professional such as signaling completion of one or more procedures or signaling jaws (218, 220) being in the partially opened configuration.

Once certain manual operations are complete, follower pin (984) may be driven past fork (950) into second operational section (954). Once follower pin (984) passes fork (950), traveler (988) may be biased proximally to pivot automatically from alignment with first zone (960) to alignment with second zone (962) and/or third zone (964). Such a bias of traveler (988) may also prevent reentry into first zone (960) via fork (950). Instead, reentry into first zone (960) would only be accessible by driving follower pin (984) through second zone (962) and third zone (964) and back to first zone (960) via hard stop wall (932).

Once follower pin (984) is driven into second operational section (954), the direction of rotation of closure barrel (910) may be reversed to drive follower pin (984) in an opposite direction towards first end (956) associated with second zone (962). Such rotation of closure barrel (810) may be controlled either manually or robotically using robotic system (28). Regardless, during such reverse rotation, follower pin (984) may be driven into contact with first end (956). At this stage, first end (956) may provide a hard stop with respect to follower pin (984). In the present use, the particular position of first end (956) corresponds to jaws (218, 220) being driven to a fully open configuration. As such, first end (956) provides a hard stop with jaws (218, 220) in the fully opened configuration.

Once first end (956) is encountered, rotation of closure barrel (910) may again be reversed to drive follower pin (984) through second zone (962). At this stage, rotation of closure barrel (910) may be provided robotically by rotary drive outputs (68) of robotic system (28). As such, second operational section (954) is configured to promote use during robotic actuation. Specifically, as noted above, second zone (962) includes a relatively high slope to drive closure of jaws (218, 220) at a relatively fast speed of closure with relatively low power output. Thus, the portion of closure corresponding to second zone (962) may correspond to initial closure of jaws (218, 220) where tissue may not typically be encountered.

As jaws (218, 220) are closed further, jaws (218, 220) may encounter tissue either for the purpose of dissection or for compressing, cutting, and/or sealing tissue. At this stage, at least some increased force may be desirable for the purpose of tissue grasping and/or manipulation. With respect to cam profile (930), this condition may correspond to follower pin (984) being positioned within third zone (964). As noted above, the slope of cam profile (930) associated with third zone (964) may be relatively low to drive jaws (218, 220) at a relatively low speed and with a relatively high output force customized for the conditions generally encountered when closing jaws (218, 220).

Jaws (218, 220) may continue to close by driving follower pin (984) through third zone (964). At this stage, a software stop may be used to prevent continued rotation of closure barrel (910) to drive follower pin (984) from third zone (964) into first zone (960). Specifically, control circuitry of robotic system (28) may be used to extrapolate the position of follower pin (984) within cam profile (930) using the position of rotary drive inputs (68). Thus, control circuitry of robotic system (28) may be used to provide a functional hard stop once jaws (218, 220) may be fully closed.

After the sequence described above is completed, rotation of closure barrel (910) may continue in the same direction to drive follower pin (984) through hard stop wall (932) from third zone (964) back to first zone (960). The sequence described above may then be repeated with manual operation being used with respect to first zone (960) and robotic operation being used with respect to second zone (962) and third zone (964). Alternatively, robotic operation may be continued by continued rotation of closure barrel (910) under robotic control through first zone (960) directly to second zone (962) and third zone (964).

E. Closure Barrel with Diverging Operational Sections

Figure 31:
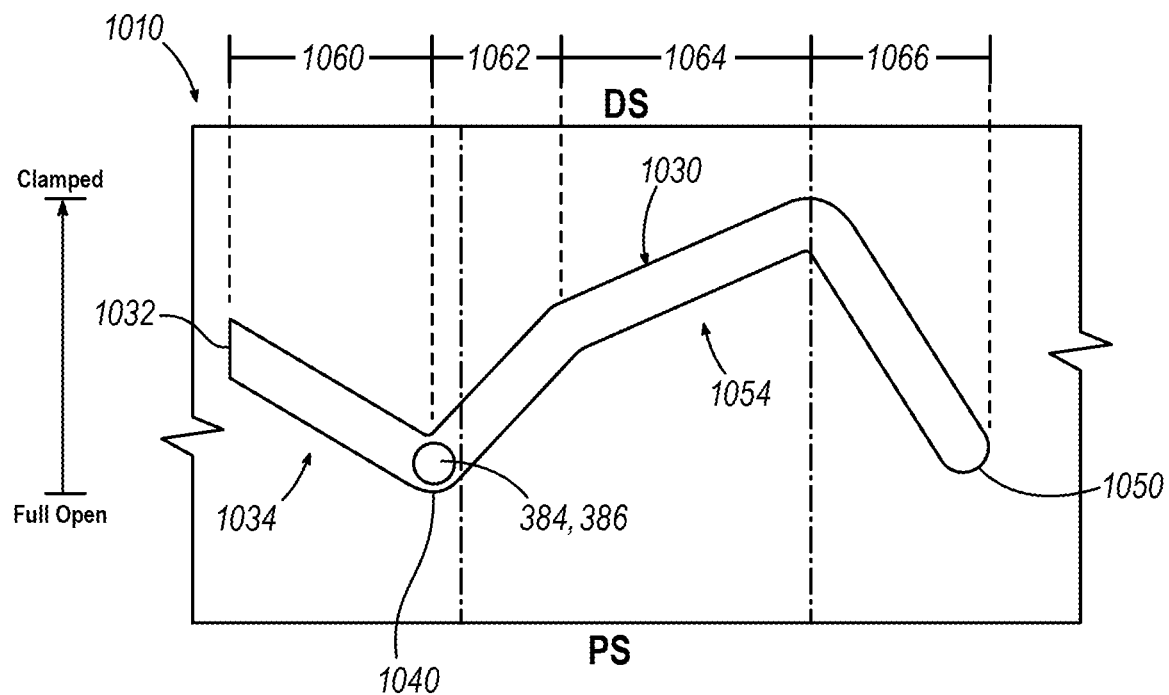
FIG. 31 depicts a schematic view of still another exemplary alternative barrel cam for use with the jaw activating mechanism of FIG. 13.

FIG. 31 shows an exemplary alternative closure barrel (1010) that may be readily incorporated into instrument (210) in addition to or in lieu of closure barrel (368). Closure barrel (1010) of the present example is substantially similar to closure barrel (368) described above in that closure barrel (1010) includes a driven gear (not shown) configured to mesh with drive gear (366) (see FIG. 14) or other similar structures to drive rotation of closure barrel (1010). Similarly, closure barrel (1010) includes a cam profile (1030) configured to receive one or both of follower pins (384, 386) to drive actuation of jaws (218, 220) or other similar structures via rotation of closure barrel (1010).

As with cam profile (530, 630, 730, 830, 930) discussed above, cam profile (1030) of the present example is shown schematically in an "un-rolled" configuration. In this "un-rolled" configuration, cam profile (1030) is shown as if closure barrel (1010) was cut along a longitudinal rotation axis and laid out flat in a plane. In addition, the orientation of the schematic of FIG. 31 is the opposite as the perspective of closure barrel (510) shown in FIG. 16. Specifically, the distal side (DS) of cam profile (1030) is oriented upwardly toward the top of the present figures, while the proximal side (PS) of cam profile (1030) is oriented downwardly toward the bottom of the present figures.

Although the present example shows a single cam profile (1030) schematically, it should be understood that in other examples closure barrel (1010) may include multiple cam profiles (1030) to provide a cam profile (1030) for each follower pin (384, 386). In some such examples, closure barrel (1010) may include two cam profiles (1030) on opposite sides of closure barrel (1010) similar to the configuration of closure barrel (368) and cam profiles (380, 382) discussed above. In other such examples, closure barrel (1010) may include two cam profiles (1030) staggered along the length of closure barrel (1010). This particular configuration may be desirable where a single cam profile (1030) extends along the full circumference of closure barrel (1010). Of course, various other suitable configurations of multiple cam profiles (1030) will be readily apparent to those of ordinary skill in the art in view of the teachings herein.

Cam profile (1030) includes a first end (1032) and a second end (1050). Both ends (1032, 1050) define a physical stop for one or more of follower pins (384, 386) or other structures similar to follower pins (384, 386). As will be described in greater detail below, first end (1032) is generally configured to engage one or more of follower pins (384, 386) such that jaws (218, 220) may be in a generally partially open position when one or more of follower pins (384, 386) are positioned at first end (1032). Similarly, second end (1050) is generally configured to engage one or more of follower pins (384, 386) such that jaws (218, 220) may be in a generally fully open position when one or more of follower pins (384, 386) are positioned at second end (1050).

Cam profile (1030) extends between each end (1032, 1050) and defines two operational sections (1034, 1054). As will be described in greater detail below, operational sections (1034, 1054) are generally configured to provide different operational profiles tailored for different operations of instrument (210). For instance, in some uses of instrument (210), functions of instrument (210) may be actuated manually by a clinician or other professional using a knob or other input feature configured to manually drive instrument (210). Meanwhile, in other uses of instrument, the same functions may also be driven by drive inputs (10) of robotic system (10). As such, different operational profiles may be desirable to promote ease of use and/or operational efficiency.

Figure 32:
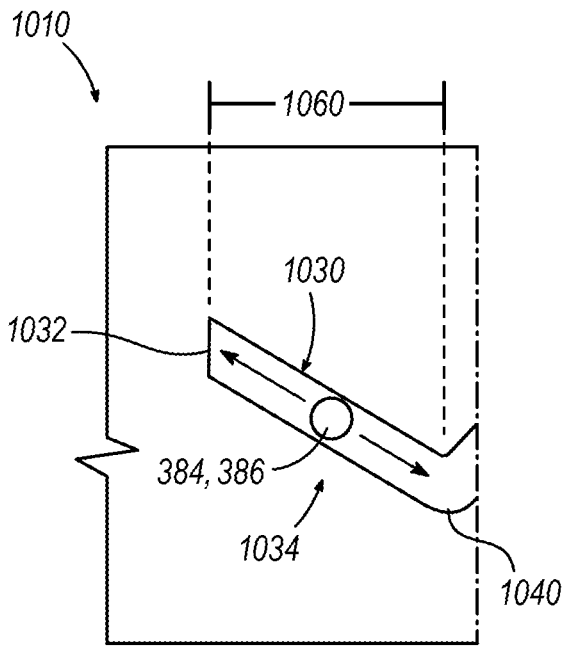
FIG. 32 depicts a detailed schematic view of a first operational section of the barrel cam of FIG. 31.

As can be seen in FIG. 32, cam profile (1030) includes a first operational section (1034) extending from first end (1032). First operational section (1034) is generally configured to drive one or more functions of instrument (210) with low power input. As will be described in greater detail below, in some uses such low power input may be desirable for manual operation of instrument (210) by a clinician or other professional.

First operational section (1034) defines a first zone (1060) having a relatively constant slope that extends from first end (1032) to an inflection point (1040) positioned between first operational section (1034) and a second operational section (1054) (described in greater detail below). The particular slope associated with first zone (1060) may be relatively low. A relatively low slope may be desirable to permit actuation of one or more functions of instrument (210) with limited power input to closure barrel (1010) via driven gear (not shown). Although only a single slope is shown with respect to first zone (1060), it should be understood that in other examples varying slopes may be used as similarly described above with respect to cam profile (530). Such varying slopes many be desirable to provide variable speed and/or force profiles as cam profile (1030) is used to actuate one or more functions of instrument (210).

Figure 33:
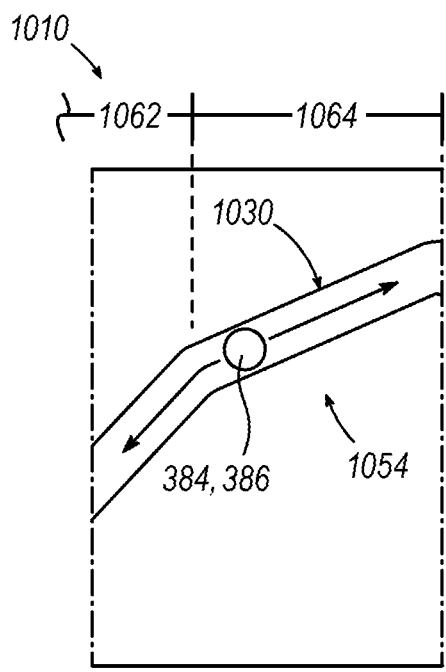
FIG. 33 depicts a detailed schematic view of a second operational section of the barrel cam of FIG. 31.
Figure 34:
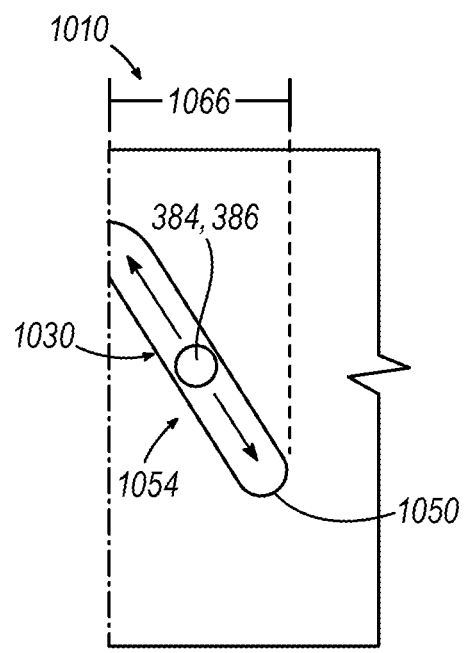
FIG. 34 depicts another detailed schematic view of the second operational section of FIG. 31.

As can be seen in FIGS. 33 and 34, cam profile (1030) further includes a second operational section (1054) extending from inflection point (1040) to second end (1050). Second operational section (1054) is generally configured to drive one or more functions of instrument (210) with power input associated with rotary drive outputs (68) of robotic system (28). As will be described in greater detail below, in some uses such power input may be desirable for operation of instrument (210) by robotic system (28).

As best seen in FIG. 33, second operational section (1034) defines a second zone (1062), a third zone (1064), and a fourth zone (1066). As will be described in greater detail below, zones (1062, 1064, 1066) are generally configured to provide different operational characteristics as one or more functions of instrument (210) are driven by rotary drive outputs (68) of robotic system (28). For instance, second zone (1062) defines a relatively high slope of cam profile (1030). Similarly to the high slopes discussed above with respect to cam profile (530), the relatively high slope of cam profile (1030) in second zone (1062) is generally configured to provide relatively fast operation of one or more functions of instrument (210), but with relatively low power output. As will be discussed in greater detail below, second zone (1062) may correspond to initial closure of jaws (218, 220) where speed of closure may be more desirable than power output.

Third zone (1064) extends away from second zone (1062) towards fourth zone (1066). Third zone (1064) defines a relatively low slope of cam profile (1030). Similarly to the low slopes discussed above with respect to cam profile (530), the relatively low slope of cam profile (1030) in third zone (1064) is generally configured to provide relatively slow operation of one or more functions of instrument (210), but with relatively high power output. As will be described in greater detail below, third zone (1064) may correspond to closure of jaws (218, 220) where engagement with tissue may occur. Thus, power output may be more desirable than speed of closure at this stage.

As best seen in FIG. 34, fourth zone (1066) extends away from second zone (1062) and third zone (1064) toward second end (1050). Four zone (1066) defines a relatively high slope that is also opposite the slopes associated with second zone (1062) and third zone (1064). As with the relatively high slopes discussed above, the relatively high slope of cam profile (1030) in fourth zone (1066) is generally configured to provide relatively fast operation of one or more functions of instrument (210) with relatively low power output. As will be described in greater detail below, fourth zone (1066) may correspond to opening of jaws (218, 220) during a bailout procedure. As will be understood, during such a bailout procedure relatively high actuation speeds may be desirable over relatively high power outputs.

In an exemplary use of cam profile (1030) with instrument (210), one or more of follower pins (384, 386) may be driven within first operational section (1034) or second operational section (1054) during different stages of operation. For instance, referring to FIG. 32, one or more of follower pins (384, 386) may be driven within first operational section (1034) when instrument (210) is manually actuated by a clinician or other professional using a knob, wheel, crank, or other manual input feature. Manual actuation may be referred to as "off-robot" use in some circumstances. Such off-robot uses may be desirable for certain functions that are more typically performed by a clinician or other professional. By way of example only, one such off-robot uses may correspond to installation of a staple cartridge in lower jaw (218), replacement of a used staple cartridge with a new staple cartridge, application of a buttress or other adjunct material to a staple cartridge, and/or other operational uses.

Regardless of the particular purpose of such manual or off-robot actuation, the particular configuration of first operational section (1034) is configured to promote ease of use when closure barrel (1010) is driven by manual input via driven gear (not shown). For instance, as noted above, first operational section (1034) includes first zone (1060) having a relatively low slope. This low slope within first zone (1060) provides movement of jaws (218, 220) via one or more of follower pins (384, 386) with relatively low input power. Consequently, a clinician or other professional may actuate jaws (218, 220) by actuating one or more of follower pins (384, 386) within first zone (1060) between first end (1032) and inflection point (1040).

In some uses during manual actuation, one or more of follower pins (384, 386) may initially be positioned adjacent to inflection point (1040). At this position, jaws (218, 220) may be in a fully open configuration. A clinician or other professional may then close jaws (218, 220) further by driving one or more of follower pins (384, 386) along cam profile (1030) toward first end (1032). Once one or more of follower pins (384, 386) reach first end (1032), jaws (218, 220) may be in a partially closed configuration rather than a fully closed configuration. This may be generally desirable during manual operation because full closure may not be necessary during operational uses associated with manual actuation.

To transition one or more of follower pins (384, 386) from first operational section (1034) to second operational section (1054) (or vice versa), one or more follower pins (384, 386) may be driven through inflection point (1040) from first end (1032) or any other position within first zone (1060). Although not shown, it should be understood that in some examples, cam profile (1030) may include a structure similar to functional wall (640) described above at inflection point (1040) to provide a detectable transition between first operational section (1034) and second operational section (1054). In the present use, transition between first operational section (1034) and second operational section (1054) may occur during a homing procedure either after initial setup of robotic system (28) or after a clinician or other professional has completed various manual operational steps.

Once one or more of follower pins (384, 386) are driven to second operational section (1054), jaws (218, 220) may be actuated robotically by rotary drive outputs (68) of robotic system (28). As such, second operational section (1054) is configured to promote use during robotic actuation. Specifically, second zone (1062) defines a relatively high slope to drive one or more of follower pins (384, 386) at a relatively fast speed with relatively low output power. This results in jaws (218, 220) being actuated at a relatively fast speed with relatively low output power. In the present example, this stage of actuation corresponds to initial closure of jaws (218, 220). At this stage, tissue is generally not encountered. Thus, speed of closure may be more desirable than power output.

As jaws (218, 220) are closed further, jaws (218, 220) may encounter tissue either for the purpose of dissection or for compressing, cutting, and/or sealing tissue. At this stage, at least some increased force may be desirable for the purpose of tissue grasping and/or manipulation. With respect to cam profile (1030), this condition may correspond to one or more of follower pins (384, 386) being positioned within third zone (1064). As noted above, the slope of cam profile (1030) associated with third zone (1064) may be relatively low to drive jaws (218, 220) at a relatively low speed and with a relatively high force customized for the conditions generally encountered when closing jaws (218, 220).

Jaws (218, 220) may continue to close by driving one or more of follower pins (384, 386) through third zone (1064). In some uses, a software stop may be used to prevent continued rotation of closure barrel (1010) to inadvertently or prematurely drive one or more of follower pins (384, 386) from third zone (1064) into fourth zone (1066). Specifically, control circuitry of robotic system (28) may be used to extrapolate the position of one or more of follower pins (384, 386) within cam profile (1030) using the position of rotary drive inputs (68). Thus, control circuitry of robotic system (28) may be used to provide a functional hard stop once jaws (218, 220) may be fully closed.

At any stage during operation with second operational section (1054), it may be desirable to initiate a bailout procedure. A bailout procedure may be desirable in a variety of circumstances when unexpected operational conditions may be encountered. During such a procedure, one or more of follower pins (384, 386) may be driven manually by a clinician or other professional through second zone (1062) and/or third zone (1064) and into fourth zone (1066) to open jaws (218, 220). For instance, if the bailout procedure is initiated with jaws (218, 220) fully closed and one or more of follower pins (384, 386) are within third zone (1064) adjacent to fourth zone (1066), closure barrel (1010) may be actuated to drive one or more of follower pins (384, 386) directly into fourth zone (1066) toward second end (1050). As best seen in FIG. 34, the relatively high slope associated with fourth zone (1066) may provide relatively quick opening of jaws (218, 220).

Once one or more of follower pins (384, 386) are positioned adjacent to second end (1050), a hard stop is reached with jaws (218, 220) positioned in the fully open configuration. At this stage, the bailout procedure may be easily detectable due to the hard stop associated with second end (1050). In some uses, detection of initiation of the bailout procedure may be desirable to provide a system lockout.

F. Closure Barrel with Divergent Operational Sections Having Different Slopes

Figure 35:
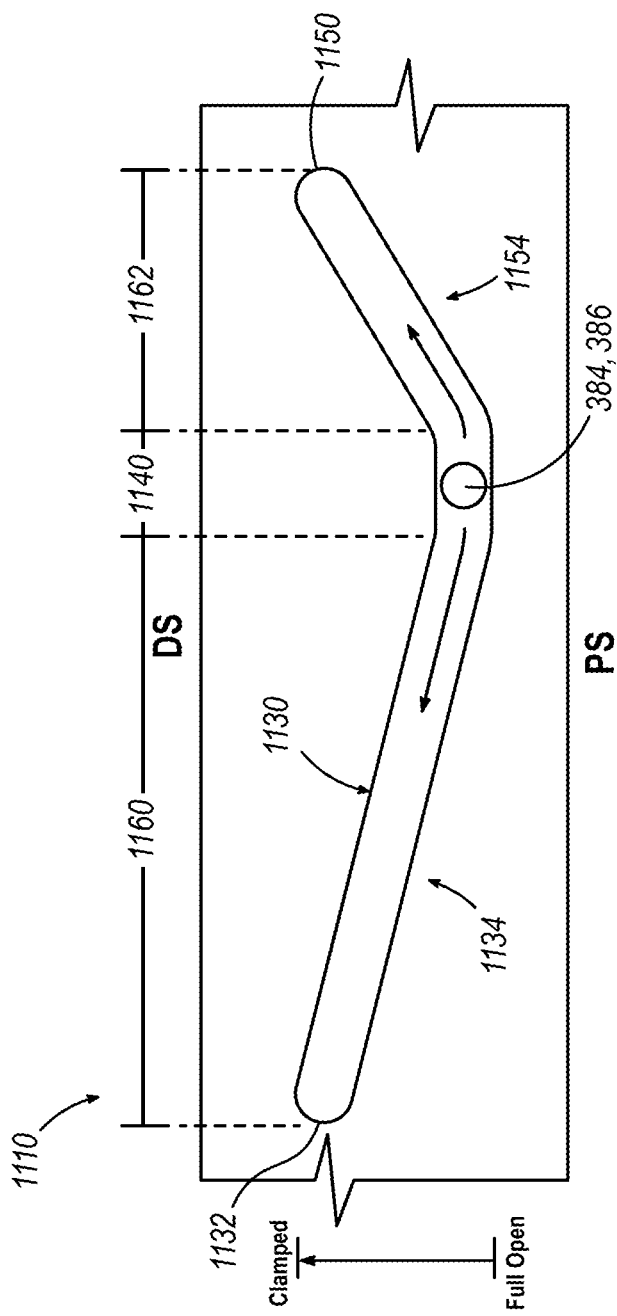
FIG. 35 depicts a schematic view of still another exemplary alternative barrel cam for use with the jaw activating mechanism of FIG. 13.

FIG. 35 shows an exemplary alternative closure barrel (1110) that may be readily incorporated into instrument (210) in addition to or in lieu of closure barrel (368). Closure barrel (1110) of the present example is substantially similar to closure barrel (368) described above in that closure barrel (1110) includes a driven gear (not shown) configured to mesh with drive gear (366) (see FIG. 14) or other similar structures to drive rotation of closure barrel (1110). Similarly, closure barrel (1110) includes a cam profile (1130) configured to receive one or both of follower pins (384, 386) to drive actuation of jaws (218, 220) or other similar structures via rotation of closure barrel (1110).

As with cam profile (530, 630, 730, 830, 930, 1030) discussed above, cam profile (1130) of the present example is shown schematically in an "un-rolled" configuration. In this "un-rolled" configuration, cam profile (1130) is shown as if closure barrel (1110) was cut along a longitudinal rotation axis and laid out flat in a plane. In addition, the orientation of the schematic of FIG. 35 is the opposite as the perspective of closure barrel (510) shown in FIG. 16. Specifically, the distal side (DS) of cam profile (1130) is oriented upwardly toward the top of the present figures, while the proximal side (PS) of cam profile (1130) is oriented downwardly toward the bottom of the present figures.

Although the present example shows a single cam profile (1130) schematically, it should be understood that in other examples closure barrel (1110) may include multiple cam profiles (1130) to provide a cam profile (1130) for each follower pin (384, 386). In some such examples, closure barrel (1110) may include two cam profiles (1130) on opposite sides of closure barrel (1110) similar to the configuration of closure barrel (368) and cam profiles (380, 382) discussed above. In other such examples, closure barrel (1110) may include two cam profiles (1130) staggered along the length of closure barrel (1110). This particular configuration may be desirable where a single cam profile (1130) extends along the full circumference of closure barrel (1110). Of course, various other suitable configurations of multiple cam profiles (1130) will be readily apparent to those of ordinary skill in the art in view of the teachings herein.

Cam profile (1130) includes a first end (1132) and a second end (1150). Both ends (1132, 1150) define a physical stop for one or more of follower pins (384, 386) or other structures similar to follower pins (384, 386). As will be described in greater detail below, first end (1132) is generally configured to engage one or more of follower pins (384, 386) such that jaws (218, 220) may be in a generally fully open position when one or more of follower pins (384, 386) are positioned at first end (1132). Similarly, second end (1150) is generally configured to engage one or more of follower pins (384, 386) such that jaws (218, 220) may be in the generally fully open position when one or more of follower pins (384, 386) are positioned at second end (1150).

Cam profile (1130) extends between each end (1132, 1150) and defines two operational sections (1134, 1154). As will be described in greater detail below, operational sections (1134, 1154) are generally configured to provide different operational profiles tailored for different operations of instrument (210). For instance, in some uses of instrument (210), speed of actuation may be less desirable than output power. In other uses of instrument (210), speed of actuation may be more desirable relative to output power. As such, different operational profiles may be desirable to promote ease of use and/or operational efficiency under different operational circumstances.

Cam profile (1130) includes a first operational section (1134) extending from first end (1132) to an inflection zone (1140). First operational section (1134) is generally configured to drive one or more functions of instrument (210) with high power output and relatively low speed. As will be described in greater detail below, in some uses such high power output with low speed may be desirable for robotic operation of instrument (210) in connection with dense tissue or other applications where high power output may be beneficial.

First operational section (1134) defines a first zone (1160) having a relatively constant slope that extends from first end (1132) to inflection zone (1140) positioned between first operational section (1134) and a second operational section (1154) (described in greater detail below). The particular slope associated with first zone (1160) may be relatively low. A relatively low slope may be desirable to permit actuation of one or more functions of instrument (210) with high power output and low speeds. In addition, or in the alternative, low slope may be desirable for limited power input to closure barrel (1110) via driven gear (not shown). Although only a single slope is shown with respect to first zone (1160), it should be understood that in other examples varying slopes may be used as similarly described above with respect to cam profile (530). Such varying slopes many be desirable to provide variable speed and/or force profiles as cam profile (1130) is used to actuate one or more functions of instrument (210).

Cam profile (1130) further includes a second operational section (1154) extending from inflection zone (1140) to second end (1150). Second operational section (1154) is generally configured to drive one or more functions of instrument (210) robotically with relatively low power output, but at relatively high speeds. As will be described in greater detail below, in some uses such low power output may be desirable for operation of instrument (210) with delectate tissue or other applications where low power output or high speeds may be beneficial.

Second operational section (1134) defines a second zone (1162). As will be described in greater detail below, second zone (1162) is generally configured to provide different operational characteristics as one or more functions of instrument (210) are driven by rotary drive outputs (68) of robotic system (28). For instance, second zone (1162) defines a relatively high slope of cam profile (1130). Similarly to the high slopes discussed above with respect to cam profile (530), the relatively high slope of cam profile (1130) in second zone (1162) is generally configured to provide relatively high speed operation of one or more functions of instrument (210) with relatively low power output. As will be discussed in greater detail below, second zone (1162) may correspond to closure of jaws (218, 220) where speed of closure may be desirable for efficiency or where low power output may be desirable for manipulating delicate tissue.

In an exemplary use of cam profile (1130) with instrument (210), one or more of follower pins (384, 386) may be driven within first operational section (1134) or second operational section (1154) to provide selectable modes of operation with either low speed and high power output or high speed and low power output. In the present use, closure barrel (1110) is generally driven robotically by rotary drive outputs (68) of robotic system (28). Thus, both first operational section (1134) and second operational section (1154) are generally configured for robotic use. However, it should be understood that in other examples, either first operational section (1134) or second operational section (1154) may be configured for manual actuation by a clinician or other professional using a knob, wheel, crank, or other manual input feature.

Initially, one or more of follower pins (384, 386) may be positioned within inflection zone (1140). At this stage, an operator may determine whether high low speed and high power output or high speed and low power output is more desirable for a given procedure. A particular mode of operation may then be initiated by rotating closure barrel (1110) in one direction to engage first operational section (1134) or another direction to engage second operational section (1154). For instance, for low speed and high power output, closure barrel (1110) may be rotated to engaged one or more of follower pins (384, 386) with first operational section (1134). As noted above, first operational section (1134) includes first zone (1160) having a relatively low slope. This low slope within first zone (1160) provides movement of jaws (218, 220) via one or more of follower pins (384, 386) with relatively low speed and relatively high power output.

To transition one or more of follower pins (384, 386) from first operational section (1134) to second operational section (1154) (or vice versa), one or more follower pins (384, 386) may be driven through inflection zone (1140) from first end (1132) or any other position within first zone (1160). Although not shown, it should be understood that in some examples, cam profile (1130) may include a structure similar to functional wall (640) described above at inflection zone (1140) to provide a detectable transition between first operational section (1134) and second operational section (1154). In some uses, transition from first operational section (1134) to second operational section (1154) may occur in a single procedure. In other uses, only first operational section (1134) or second operational section (1154) may be used in a single procedure. Thus, where use of the high speed and low power output associated with second operational section (1154) is desired for a single procedure, closure barrel (1110) may be rotated to directly engage one or more of follower pins (384, 386) with second operational section (1154).

Regardless, once one or more of follower pins (384, 386) are driven to second operational section (1154), jaws (218, 220) may be actuated robotically by rotary drive outputs (68) of robotic system (28) at a relatively high speed and relatively low power output. Specifically, second zone (1162) defines a relatively high slope to drive one or more of follower pins (384, 386) at a relatively fast speed with relatively low output power. This results in jaws (218, 220) being actuated at a relatively fast speed with relatively low output power.

Figure 36A:
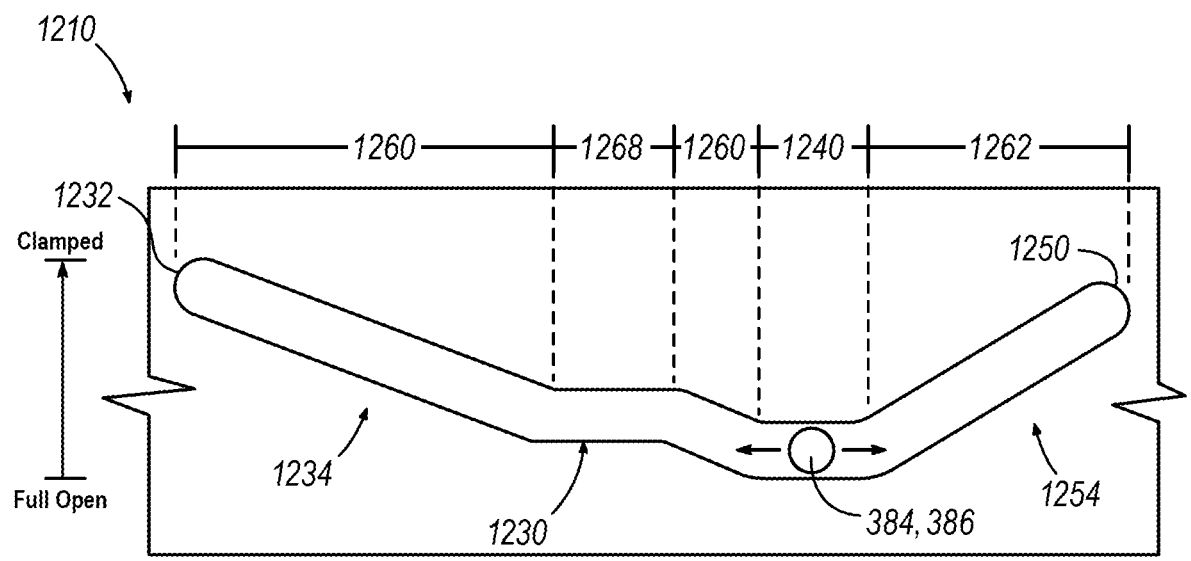
FIG. 36A depicts a schematic view of still another exemplary alternative barrel cam for use with the jaw activating mechanism of FIG. 13.

FIG. 36A shows an exemplary alternative closure barrel (1210) that is substantially similar to closure barrel (1110) described above. For instance, like with closure barrel (1110) described above, closure barrel (1210) of the present example includes cam profile (1230) having a first end (1232), a second end (1250). Similarly, between first end (1232) and second end (1250), cam profile (1230) defines a first operational section (1234) and a second operational section (1254), separated by an inflection zone (1240). As with first operational section (1134) and second operational section (1154) described above, first operational section (1234) and second operational section (1254) are both generally configured to selectively provide different operational characteristics when actuating instrument (210) under robotic operation.

Second operational section (1254) is generally substantially similar to second operational section (1154) described above. For instance, like with second operational section (1154) described above, second operational section (1254) of the present example includes a second zone (1262) that defines a relatively high slope configured to provide a relatively high speed drive with relatively low output power.

Unlike closure barrel (1110) described above, closure barrel (1210) of the present example includes a modified first operational section (1234) relative to first operational section (1134) described above. For instance, although first operational section (1234) of the present example includes a first zone (1260) having a relatively low pitch similar to first zone (1160) described above, first zone (1260) of the present example is interrupted by a partial aperture zone (1268). Partial aperture zone (1268) defines a zero slope region where closure barrel (1210) may rotate without actuating one or more functions of instrument (210). As will be described in greater detail below, this functionality may be desirable to hold jaws (218, 220) in a partially open configuration for a predetermined period during closure of jaws (218, 220) before resuming closure.

Figure 36B:
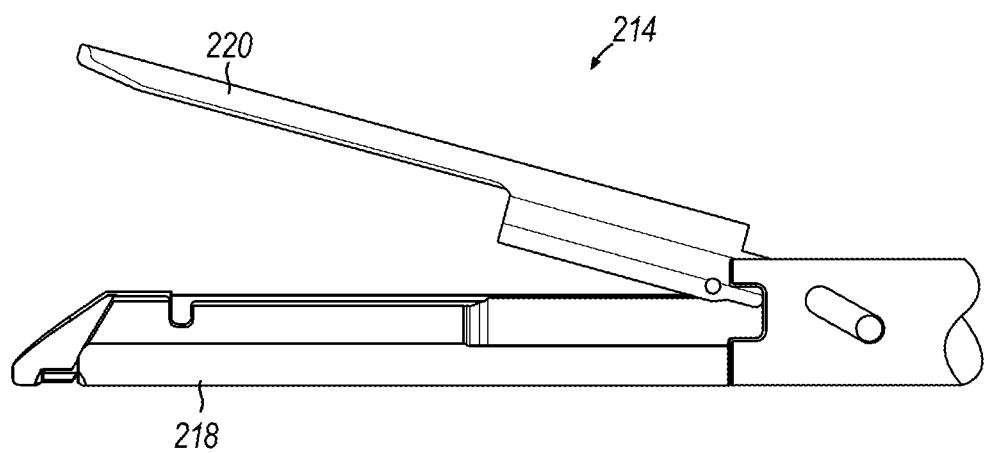
FIG. 36B depicts a side elevational view of the end effector of FIG. 7, with the end effector in a fully open configuration.
Figure 37A:
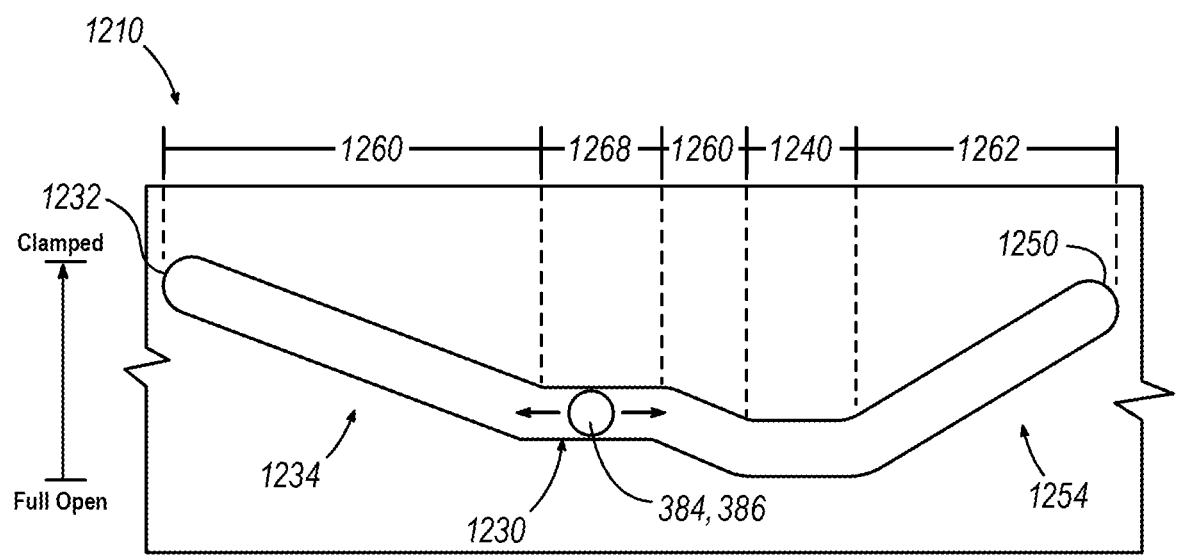
FIG. 37A depicts another schematic view of the barrel cam of FIG. 36A, with the barrel cam configured to hold the end effector of FIG. 7 in a partially open configuration.
Figure 37B:
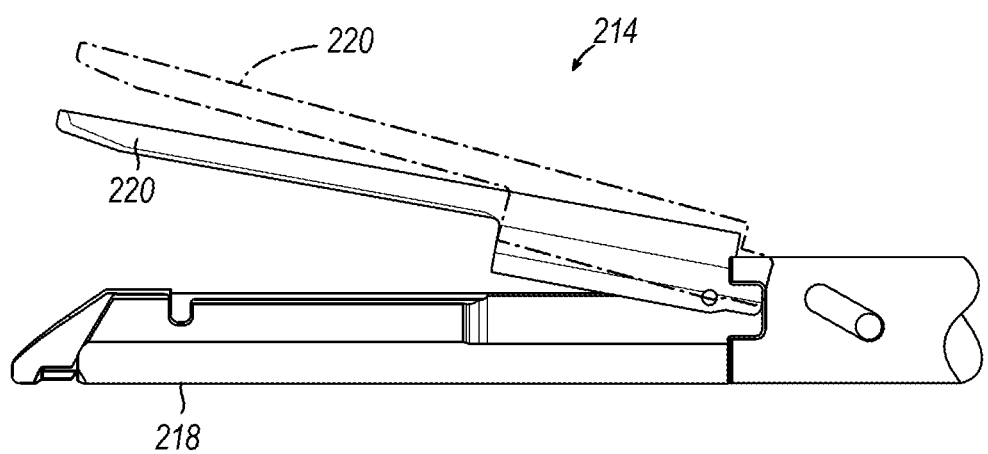
FIG. 37B depicts another side elevational view of the end effector if FIG. 7, with the end effector in the partially open configuration.

In use, closure barrel (1210) of the present example operates substantially similarly to closure barrel (1110) described above except with respect to operation associated with first operational section (1234). For instance, when first operational section (1234) is engaged for use, first zone (1260) is generally configured to provide low speed and high power closure of jaws (218, 220) from a fully open configuration shown in FIG. 36B. However, when one or more of follower pins (384, 386) reach partial aperture zone (1268) as shown in FIG. 37A, such closure of jaws (218, 220) may stop temporarily in a partially open configuration shown in FIG. 37B.

The partially open configuration associated with partial aperture zone (1268) may be desirable in some uses where delicate tissue may prevent use of the full range of motion of jaws (218, 220). In addition, or in the alternative, rotation of closure barrel (1210) may be stopped entirely at this stage to hold jaws (218, 220) in the partially open configuration shown in FIG. 37B. Holding jaws (218, 220) in the partially open configuration using partial aperture zone (1268) may be preferable to other methods because the zero slope of partial aperture zone (1268) may result in limited torque input to maintain jaws (218, 220) in the partially open configuration. In practice, this may be beneficial to reduce heat generated by rotary drive outputs (68) of robotic system. In some uses, this may also be beneficial by giving an operator an opportunity to release operator controls associated with instrument (210).

Figure 38A:
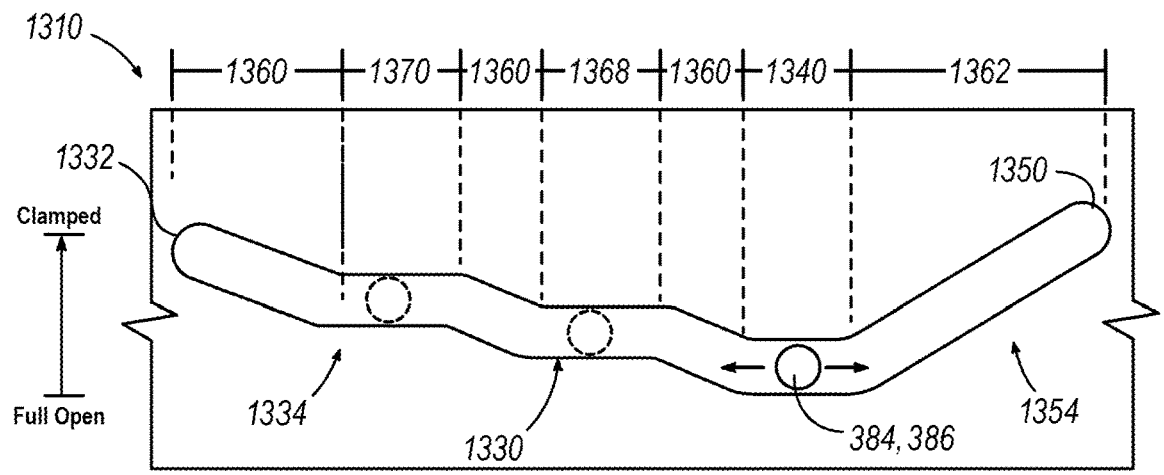
FIG. 38A depicts a schematic view of still another exemplary alternative barrel cam for use with the jaw activating mechanism of FIG. 13.

FIG. 38A shows an exemplary alternative closure barrel (1310) that is substantially similar to closure barrel (1110) described above. For instance, like with closure barrel (1110) described above, closure barrel (1310) of the present example includes cam profile (1330) having a first end (1332) and a second end (1350). Similarly, between first end (1332) and second end (1350), cam profile (1330) defines a first operational section (1334) and a second operational section (1354), separated by an inflection zone (1340). As with first operational section (1134) and second operational section (1154) described above, first operational section (1334) and second operational section (1354) are both generally configured to selectively provide different operational characteristics when actuating instrument (210) under robotic operation.

Second operational section (1354) is generally substantially similar to second operational section (1154) described above. For instance, like with second operational section (1154) described above, second operational section (1354) of the present example includes a second zone (1362) that defines a relatively high slope configured to provide a relatively high speed drive with relatively low output power.

Unlike closure barrel (1110) described above, closure barrel (1310) of the present example includes a modified first operational section (1334) relative to first operational section (1134) described above. For instance, although first operational section (1334) of the present example includes a first zone (1360) having a relatively low pitch similar to first zone (1160) described above, first zone (1360) of the present example is interrupted by two partial aperture zones (1368, 1370). Partial aperture zones (1368, 1370) both define a zero slope region where closure barrel (1310) may rotate without actuating one or more functions of instrument (210). As will be described in greater detail below, this functionality may be desirable to hold jaws (218, 220) in one of two partially open configurations for a predetermined period during closure of jaws (218, 220) before resuming closure.

Figure 38B:
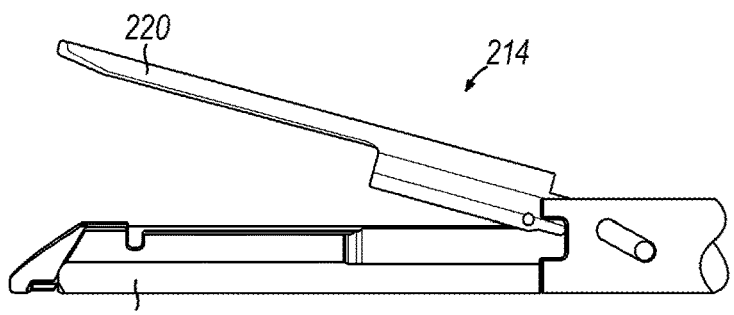
FIG. 38B depicts a side elevational view of the end effector of FIG. 7, with the end effector in the fully open configuration.
Figure 38C:
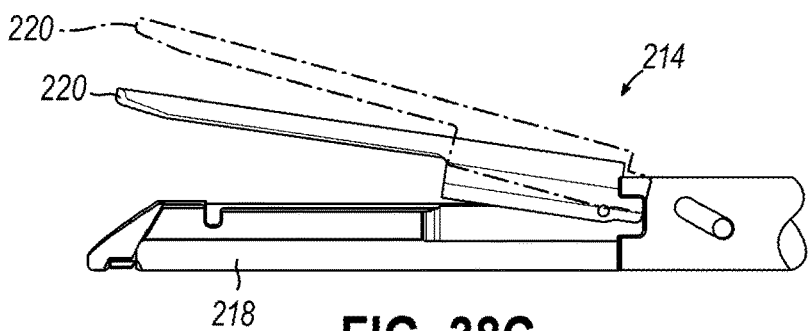
FIG. 38C depicts another side elevational view of the end effector of FIG. 7, with the end effector in a first partially open configuration.

In use, closure barrel (1310) of the present example operates substantially similarly to closure barrel (1110) described above except with respect to operation associated with first operational section (1334). For instance, when first operational section (1334) is engaged for use, first zone (1360) is generally configured to provide low speed and high power closure of jaws (218, 220) from a fully open configuration shown in FIG. 38B. However, when one or more of follower pins (384, 386) reach a first partial aperture zone (1368), such closure of jaws (218, 220) may stop temporarily in a first partially open configuration shown in FIG. 38C.

Figure 38D:
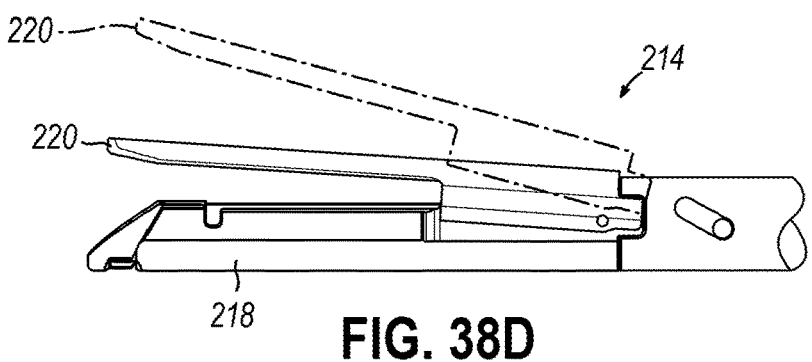
FIG. 38D depicts yet another side elevational view of the end effector of FIG. 7, with the end effector in a second partially open configuration.

After first partial aperture zone (1368), closure of jaws (218, 220) at low speed and high power may continue until one or more of follower pins (384, 386) reach a second partial aperture zone (1370). Closure of jaws (218, 220) may again stop temporarily in a second partially open configuration shown in FIG. 38D. In this configuration, jaws (218, 220) may be closed further relative to first partially open configuration, but still not fully closed. Continued rotation of closure barrel (1310) may next result in full closure of jaws (218, 220).

The first partially open configuration and second partially open configuration associated with first partial aperture zone (1368) and second partial aperture zone (1370) may be desirable in some uses where delicate tissue may prevent use of the full range of motion of jaws (218, 220). In addition, or in the alternative, rotation of closure barrel (1310) may be stopped entirely at this stage to hold jaws (218, 220) in the first partially open configuration shown in FIG. 38C or the second partially open configuration shown in FIG. 38D. Holding jaws (218, 220) in the either partially open configuration using partial first aperture zone (1368) or second partial aperture zone (1370) may be preferable to other methods because the zero slope of first partial aperture zone (1368) and second partial aperture zone (1370) may result in limited torque input to maintain jaws (218, 220) in the respective partially open configuration. In practice, this may be beneficial to reduce heat generated by rotary drive outputs (68) of robotic system. In some uses, this may also be beneficial by giving an operator an opportunity to release operator controls associated with instrument (210).

G. Closure Barrel Assembly with Dual Cams

Figure 39:
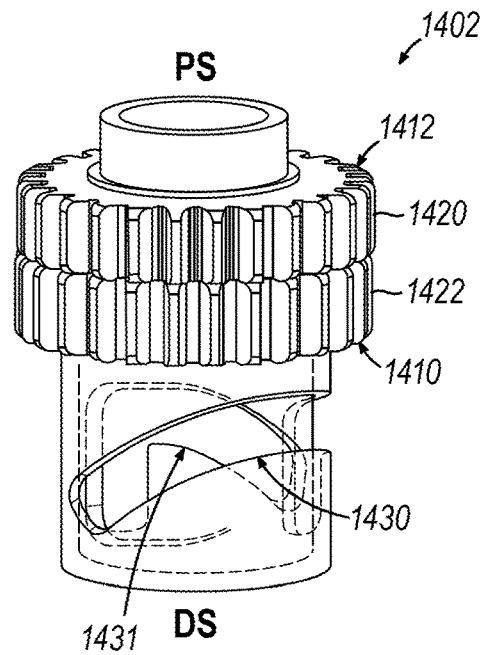
FIG. 39 depicts a perspective view of an exemplary alternative barrel cam assembly for use with the jaw activating mechanism of FIG. 13.
Figure 40:
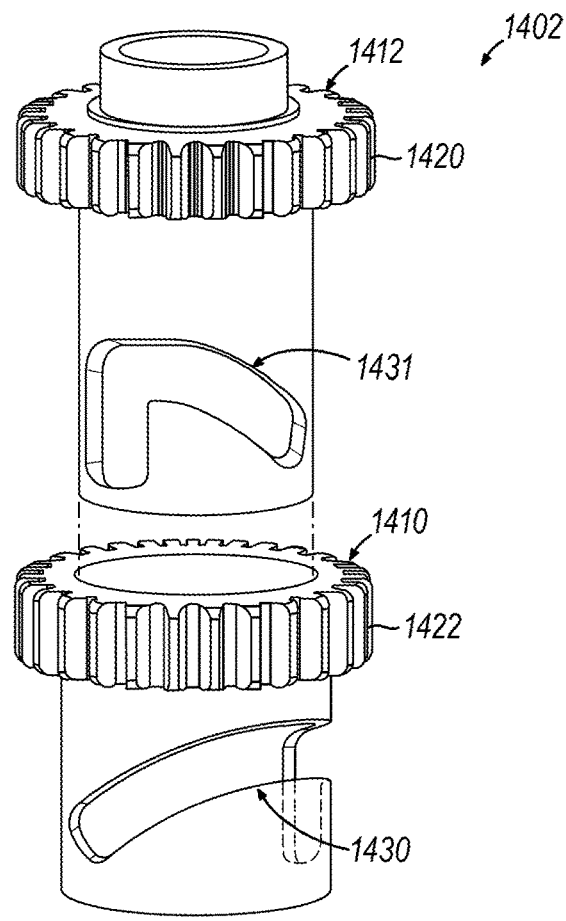
FIG. 40 depicts an exploded perspective view of the barrel cam assembly of FIG. 39.

FIGS. 39 and 40 show a dual closure barrel assembly (1402) that may be readily incorporated into instrument (210) in addition to or in lieu of closure barrel (368). Closure barrel assembly (1402) of the present example includes an inner closure barrel (1410) and an outer closure barrel (1412), with inner closure barrel (1410) nested coaxially within outer closure barrel (1412). Closure barrels (1410, 1412) of the present example are generally substantially similar to closure barrel (368) described above in that closure barrels (1410, 1412) include a driven gear (1420, 1422) configured to mesh with drive gear (366) (see FIG. 14) or other similar structures to drive rotation of each closure barrel (1410, 1412). However, due to the presence of two driven gears (1420, 1422), it should be understood that in some examples of instrument (210), multiple drive gears (366) may be incorporated into instrument (210).

Also as with closure barrel (368) described above, closure barrels (1410, 1412) of the present example each include a cam profile (1430, 1431) configured to receive one or both of follower pins (384, 386) to drive actuation of jaws (218, 220) or other similar structures via rotation of closure barrels (1410, 1412). Use of two closure barrels (1410, 1412) in the present example may be desirable in some circumstances to permit lower drive inputs as each cam profile (1430, 1431) may occupy a larger area of a respective closure barrel (1410, 1412). Alternatively, a cam profile similar to first cam profile (380) or second cam profile (382) may be spread across both cam profiles (1430, 1431) of the present example to permit a reduction in the diameter of each closure barrel (1410, 1412), thereby permitting use in smaller versions of instrument (210).

Although closure barrels (1410, 1412) and various components thereof are characterized herein using the terms "inner" and "outer," it should be understood that such terms are used only to describe the present configuration. As such, in other examples, closure barrels (1410, 1412) or various features of each closure barrel (1410, 1412) may be reversed with outer features being moved to an inner position and inner features being moved to an outer position. In other examples, the inner and outer characterization may be omitted entirely, with each closure barrel (1410, 1412) being positioned on a separate axis.

Figure 41:
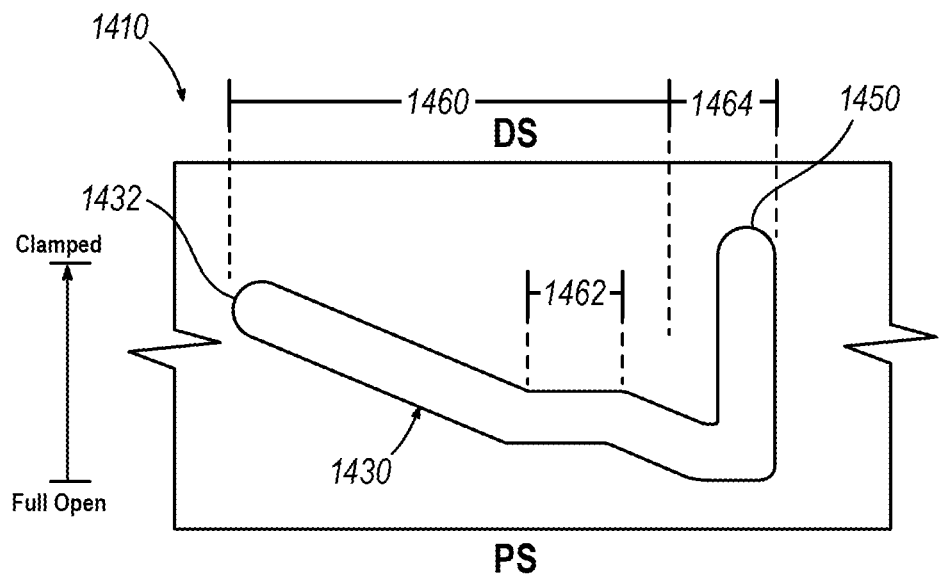
FIG. 41 depicts a schematic view of an inner closure barrel of the barrel cam assembly of FIG. 39.

As noted above, each closure barrel (1410, 1412) includes a respective cam profile (1430, 1431). As will be described in greater detail below, cam profiles (1430, 1431) are generally configured to operate cooperatively to drive movement of one or more of follower pins (384, 386) through two separate actuation sequences. In the present example, inner closure barrel (1410) includes an inner cam profile (1430). Inner cam profile (1430) is shown in greater detail in FIG. 41. As can be seen, inner cam profile (1430) extends between a first end (1432) and a second end (1450). Ends (1432, 1450) are generally configured to provide a hard stop for one or more of follower pins (384, 386) when engaged with each end (1432, 1450).

Between each end (1432, 1450), inner cam profile (1430) defines a drive zone (1460) and a free travel zone (1464). Drive zone (1460) extends away from first end (1432) toward free travel zone (1474). Drive zone (1460) is generally configured to drive follower pins (384, 386) to actuate jaws (218, 220) from an open configuration adjacent to free travel zone (1464) to a fully closed configuration adjacent to first end (1432).

The slope of cam profile (1430) within drive zone (1460) is generally constant. Although a particular slope is shown as being associated with drive zone (1460), it should be understood that a variety of slopes may be used. In addition, in some examples, the slope associated with drive zone (1460) may increase or decrease as cam profile (1430) extends away from free travel zone (1464) towards first end (1432). By way of example only, in one suitable example, the slope of drive zone (1460) may be relatively high to provide relatively fast actuation with relatively low power output. Alternatively, the slope of drive zone (1460) may be relatively low to provide relatively slow actuation with relatively high power output. Of course, in other examples various alternative slopes or combinations thereof may be used as desired for a particular application.

A portion of the constant slope associated with drive zone (1460) is interrupted by partial aperture zone (1462). Partial aperture zone (1462) is similar to partial aperture zones (1268, 1368, 1370) described above in that partial aperture zone (1462) has no slope to permit holding of jaws (218, 220) at a predetermined partially open configuration with minimal torque input. Although partial aperture zone (1462) is shown as being positioned to correspond to a partially open configuration slightly lower than the open configuration of jaws (218, 220), it should be understood that partial aperture zone (1462) may be positioned to correspond to other partially open configurations being closer to jaws (218, 220) being fully closed. In addition, or in the alternative, although the present example includes only a single partial aperture zone (1462), multiple partial aperture zones (1462) may be used in other examples.

Free travel zone (1464) extends from drive zone (1460) to second end (1450). The extension of free travel zone (1464) corresponds to the rotation axis of inner closure barrel (1410) such that free travel zone (1464) defines an undefined slope. In other words, free travel zone (1464) extends proximally along inner closure barrel (1410). As will be described in greater detail below, free travel zone (1464) is generally configured to permit free proximal-distal movement of one or more of follower pins (384, 386) when one or more of follower pins (384, 386) are driven by outer closure barrel (1412) instead of inner closure barrel (1410).

Figure 42:
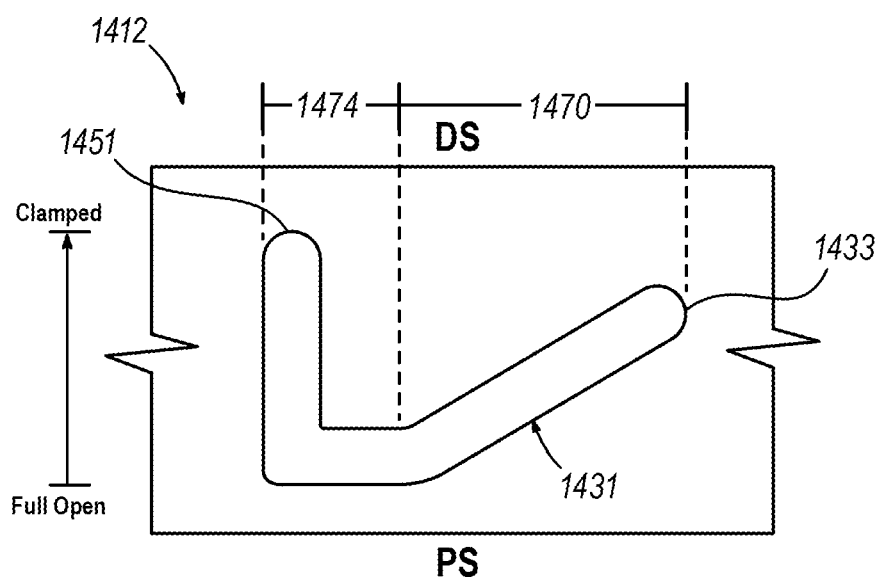
FIG. 42 depicts a schematic view of an outer closure barrel of the barrel cam assembly of FIG. 39.

Outer closure barrel (1412) includes an outer cam profile (1431). Outer cam profile (1431) is shown in greater detail in FIG. 42. Outer cam profile (1431) extends between a first end (1433) and a second end (1451). Ends (1433, 1451) are generally configured to provide a hard stop for one or more of follower pins (384, 386) when engaged with each end (1433, 1451).

Between each end (1433, 1451), outer cam profile (1431) defines a drive zone (1470) and a free travel zone (1464). Drive zone (1470) extends away from first end (1433) toward free travel zone (1474). The extension of drive zone (1470) is also in a direction opposite of the extension of drive zone (1460) described above with respect to inner closure barrel (1410). Drive zone (1470) is generally configured to drive follower pins (384, 386) to actuate jaws (218, 220) from an open configuration adjacent to free travel zone (1474) to a fully closed configuration adjacent to first end (1433).

The slope of outer cam profile (1431) within drive zone (1470) is generally constant. Although a particular slope is shown as being associated with drive zone (1470), it should be understood that a variety of slopes may be used. In addition, in some examples, the slope associated with drive zone (1470) may increase or decrease as outer cam profile (1431) extends away from free travel zone (1474) towards first end (1433). By way of example only, in one suitable example, the slope of drive zone (1470) may be relatively high to provide relatively fast actuation with relatively low power output. Alternatively, the slope of drive zone (1470) may be relatively low to provide relatively slow actuation with relatively high power output. Of course, in other examples various alternative slopes or combinations thereof may be used as desired for a particular application.

Free travel zone (1474) extends from drive zone (1470) to second end (1451). The extension of free travel zone (1474) corresponds to the rotation axis of outer closure barrel (1412) such that free travel zone (1474) defines an undefined slope. In other words, free travel zone (1474) extends proximally along outer closure barrel (1412). As will be described in greater detail below, free travel zone (1474) is generally configured to permit free proximal-distal movement of one or more of follower pins (384, 386) when one or more of follower pins (384, 386) are driven by inner closure barrel (1410) instead of outer closure barrel (1412).

In an exemplary use of closure barrel assembly (1402), closure barrels (1410, 1412) may be driven at different times to drive one or more of follower pins (384, 386) within a selected drive zone (1460, 1470). For instance, in an initial state, closure barrels (1410, 1412) may be oriented with each free travel zone (1464, 1474) aligned with the other and one or more of follower pins (384, 386) positioned at the intersection between each drive zone (1460, 1470) and each free travel zone (1464, 1474).

Once free travel zones (1464, 1474) are aligned as described above, a selected drive zone (1460, 1470) may be used to manipulate one or more of follower pins (384, 386)

by rotating a selected closure barrel (1410, 1412) associated with a given drive zone (1460, 1470), while holding the other closure barrel (1412, 1410) stationary. For instance, if it is desirable to drive one or more of follower pins (384, 386) with drive zone (1460), inner closure barrel (1410) may be rotated in a first direction to drive one or more of follower pins (384, 386) away from free travel zone (1464) towards first end (1432). Meanwhile, outer closure barrel (1412) may be held stationary relative to inner closure barrel (1410). This stationary position of outer closure barrel (1412) may then permit proximal-distal movement of one or more follower pins (384, 386) within free travel zone (1474) as one or more of follower pins (384, 386) are manipulated by drive zone (1460) of inner closure barrel (1410).

Alternatively, if it is desirable to drive one or more of follower pins (384, 386) with drive zone (1470), outer closure barrel (1412) may be rotated in a second direction, opposite the first direction, to drive one or more of follower pins (384, 386) away from free travel zone (1474) towards first end (1433). Meanwhile, inner closure barrel (1410) may be held stationary relative to outer closure barrel (1412). This stationary position of inner closure barrel (1410) may then permit proximal-distal movement of one or more follower pins (384, 386) within free travel zone (1464) as one or more of follower pins (384, 386) are manipulated by drive zone (1470) of outer closure barrel (1412).

H. Closure Barrel with Multi-Radius Cam Profile

As noted above, in some examples it is desirable to drive structures similar to follower pins (384, 386) at high speeds with low force or at low speeds with high force. However, in some circumstances efficiency of the drive may lead to reduced speed. For instance, in some circumstances, structures similar to follower pins (384, 386) may slip as they are being driven using structures similar to cam profiles (380, 382). Thus, in some examples it may be desirable to modify structures associated with follower pins (384, 386) to reduce slipping and therefore increase drive efficiency.

Figure 43:
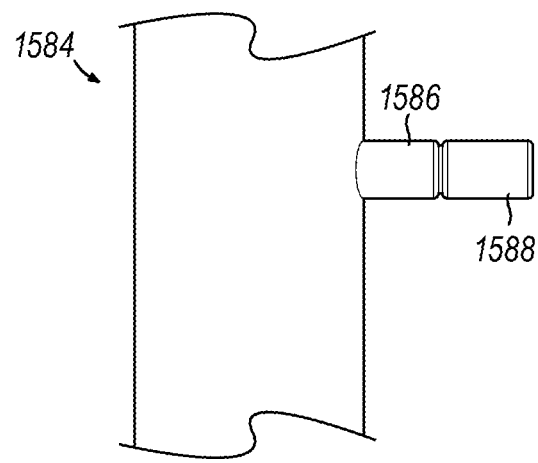
FIG. 43 depicts a side elevational view of another exemplary alternative follower pin for use with the jaw activating mechanism of FIG. 13.

FIG. 43 shows an exemplary alternative follower pin (1584) that may be used in instrument (210) in lieu of, or in addition to, follower pins (384, 386). Follower pin (1584) is generally configured to provide different engagement surfaces configured for specific applications. For instance, follower pin (1584) includes an inner follower (1586) and an outer follower (1588). Inner follower (1586) includes a solid material having a low coefficient of friction. By way of example only, suitable materials may include Teflon, high density polyethylene (HDPE), and/or etc. As will be described in greater detail below, inner follower (1586) is generally configured to provide high efficiency energy transfer from a structure similar to cam profiles (380, 382) in a context where high power outputs are used. In some examples, the particular inside position of inner follower (1586) may be desirable to reduce the bending stress on inner follower (1586) during high force applications.

Outer follower (1588) of the present example is configured as a bearing and/or roller element. The bearing associated with outer follower (1588) is generally configured to provide high efficiency by reducing friction during use. However, in contexts with high power outputs, the efficiency of bearings and/or roller elements may be reduced. Thus, outer follower (1588) of the present example is generally configured to provide high efficiency energy transfer from a structure similar to cam profiles (380, 382) in a context here low power outputs are used.

Although outer follower (1588) of the present example includes a bearing and/or roller element, it should be understood that in other examples other low friction elements may be used. For instance, in some examples, outer follower (1588) may include a low friction material such as Teflon, HDPE, and/or etc.

Although the present example includes inner follower (1586) and outer follower (1588), in other examples additional followers may be used having bearings, rollers, and/or low friction materials. For instance, in some examples, follower pin (1584) may include multiple layers of different types of followers. The particular configuration of each layer may be determined based on specific expected operational conditions and/or applications associated with each layer. In addition, or in the alternative, the particular position of inner follower (1586) and outer follower (1588) may be reversed in some examples with inner follower (1586) on the outside and outer follower (1588) on the inside.

Figure 44A:
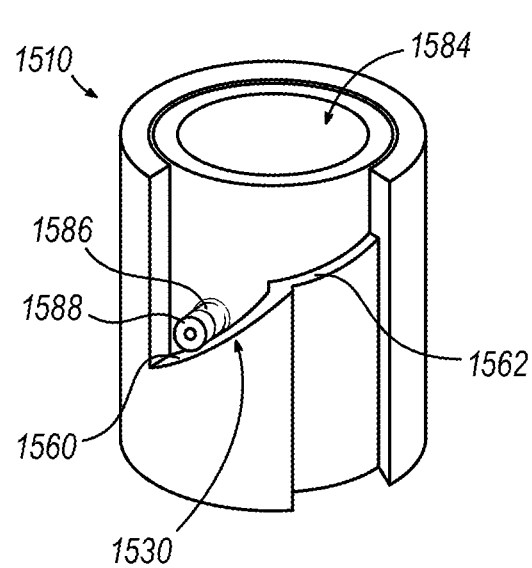
FIG. 44A depicts a perspective view of still another exemplary alternative barrel cam for use with the jaw activating mechanism of FIG. 13 and the follower pin of FIG. 43.
Figure 44B:
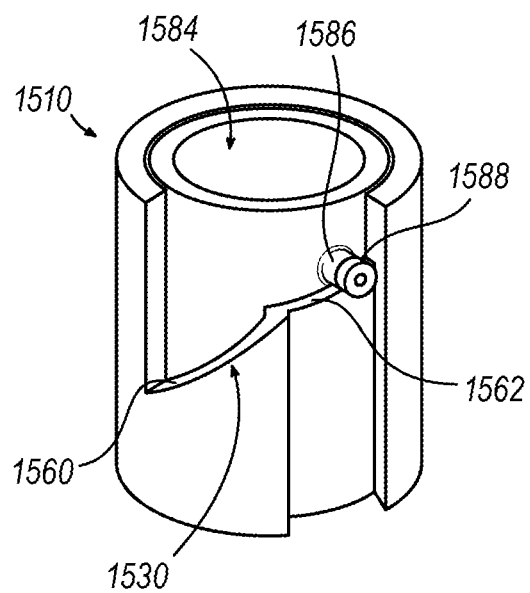
FIG. 44B depicts another perspective view of the barrel cam of FIG. 44A, with the follower pin of FIG. 43 engaged with a second zone of the barrel cam.

FIGS. 44A and 44B show an exemplary alternative closure barrel (1510) for use in instrument (210) with follower pin (1584). Closure barrel (1510) of the present example is substantially similar to closure barrel (368) described above in that closure barrel (1510) includes a driven gear (not shown) configured to mesh with drive gear (366) (see FIG. 14) or other similar structures to drive rotation of closure barrel (1510). Similarly, closure barrel (1510) includes a cam profile (1530) configured to receive follower pin (1584) to drive actuation of jaws (218, 220) or other similar structures via rotation of closure barrel (1510).

Cam profile (1530) defines two drive zones (1560, 1562) for manipulation of follower pin (1584). For instance, cam profile (1530) includes a low power output zone (1560) configured to actuate follower pin (1584) at relatively high speeds with relatively low power output. In other words, low power output zone (1560) corresponds to a section of cam profile (1530) having a relatively high slope. As will be described in greater detail below, the drive associated with low power output zone (1560) may be associated with initial closure of jaws (218, 220).

Low power output zone (1560) is positioned within closure barrel (1510) at an outer radius relative to closure barrel (1510). This outer radius is configured to correspond to the position of outer follower (1588) of follower pin (1584). In other words, low power output zone (1560) is configured to engage with outer follower (1588) of follower pin (1584) to manipulate follower pin (1584) through low power output zone (1560).

Cam profile (1530) further includes a high power output zone (1562) configured to actuate follower pin (1584) at relatively low speeds with relatively high power output. In other words, high power output zone (1562) corresponds to a section of cam profile (1540) having a relatively low slope. As will be described in greater detail below, the drive associated with high power output zone (1562) may be associated with final closure of jaws (218, 220) where tissue is encountered for stapling, cutting, compressing, and/or dissecting.

High power output zone (1562) is positioned within closure barrel (1510) at an inner radius relative to closure barrel (1520). This inner radius is configured to correspond to the position of inner follower (1586) of follower pin (1584). In other words, high power output zone (1562) is configured to engage with inner follower (1586) of follower pin (1584) to manipulate follower pin (1584) through high power output zone (1562).

In use, follower pin (1584) may initially begin with outer follower (1588) engaged with low power output zone (1560) of cam profile (1530). At this point, follower pin (1588) may be driven using low power output zone (1560) via rotation of closure barrel (1510). As noted above, outer follower (1588) is generally configured for use in applications where low power output is desired, but efficiency is also still desired. This configuration generally corresponds to the use of low power output zone (1560) because low power output zone (1560) is configured to correspond to initial closure of jaws (218, 220). As noted above, tissue or other objects may not be typically encountered during initial closure of jaws (218, 220). Additionally, in circumstances where tissue may be encountered, such encounters may include operations requiring limited force such as grasping tissue for dissection rather than clamping or cutting tissue. Thus, high speeds with lower power outputs are generally desirable at this stage.

At the transition between low power output zone (1560) and high power output zone (1562), the surface of cam profile (1560) bends inwardly towards the center of closure barrel (1510). This bend shifts engagement of follower pin (1584) from outer follower (1588) to inner follower (1586). High power output zone (1562) may then be used to drive follower pin (1584) via inner follower (1586). As noted above, inner follower (1586) is generally configured for use in applications where high power output is desired with high efficiency. This configuration generally corresponds to the use of high power output zone (1562) because high power output zone is configured to correspond to final closure of jaws (218, 220). As noted above, tissue or other objects may typically be encountered during this stage for dissection, stapling, clamping, and/or other operations associated with tissue. Thus, low speeds with high power outputs are generally desirable at this stage.

IV. Exemplary Alternative Articulation Barrels

In some examples it may be desirable to incorporate certain alternative articulation barrels into instrument (210) or other suitable instruments similar to articulation barrel (326) described above. For instance, in some examples it may be desirable to include certain features to lockout certain movements associated with the articulation barrel. Such lockout features may be desirable to promote ease of use, and/or to reduce heat or wear on mechanical equipment.

In addition, or in the alternative, in some examples it may be desirable to include certain features to modify the mechanical advantage associated with the articulation barrel. For instance, mechanical advantage may be modified to support certain instrument (210) outputs such as the speed and/or power associated with articulation of end effector (214). In addition, or in the alternative, mechanical advantage may be modified to support certain instrument (210) inputs to support manual and/or motor-based drive inputs.

A. Articulation Barrel with Articulation Lock and Multiple Drive Zones

Figure 45:
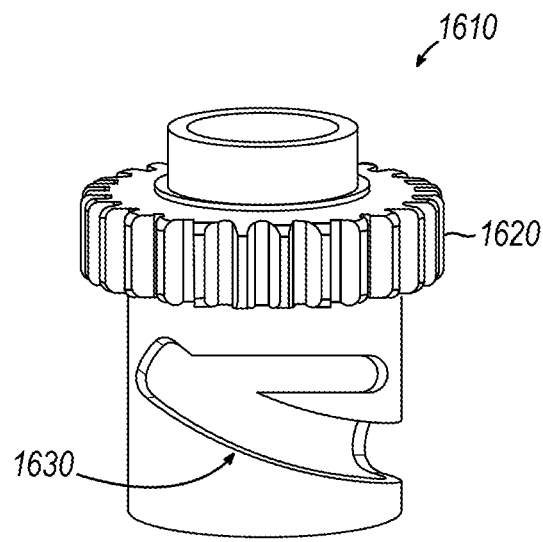
FIG. 45 depicts a perspective view of an exemplary alternative barrel cam for use with the articulation activating mechanism of FIG. 9.

FIG. 45 shows an exemplary alternative articulation barrel (1610) that may be readily incorporated into instrument (210) in addition to or in lieu of articulation barrel (326). Articulation barrel (1610) of the present example is substantially similar to articulation barrel (326) described above in that articulation barrel (1610) includes a driven gear (1620) configured to mesh with drive gear (322) (see FIG. 11) or other similar structures to drive rotation of articulation barrel (1610). Similarly, closure barrel (1610) includes a cam profile (1630) configured to receive one or both of follower pins (332, 334) to drive articulation of closure barrel (1610) or other similar structures via rotation of closure barrel (1610).

As noted above, articulation barrel (1610) includes cam profile (1630). Cam profile (1630) is similar in function to cam profiles (328, 330) described above. However, unlike cam profiles (328, 330) described above, cam profile (1630) of the present example defines two discrete zones (1660, 1662). As will be described in greater detail below, the use of two zones (1660, 1662) permits greater functionality by including an articulation zone (1660) configured for articulation and a lock zone (1662) configured for selectively locking articulation.

Figure 46:
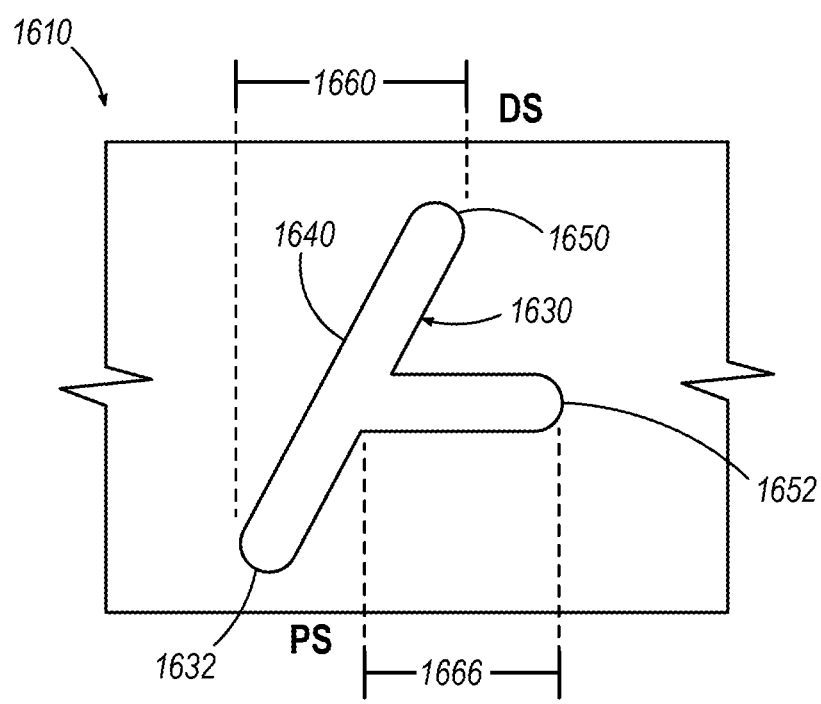
FIG. 46 depicts a schematic view of the barrel cam of FIG. 45.

Cam profile (1630) of the present example is shown in greater detail in FIG. 46. In the view shown in FIG. 46, cam profile (1630) is shown schematically in an "un-rolled" configuration. In this "un-rolled" configuration, cam profile (1630) is shown as if articulation barrel (1610) shown in FIG. 45 was cut along a longitudinal rotation axis and laid out flat in a plane. In addition, the orientation of the schematic of FIG. 46 is opposite as the perspective in FIG. 45. Specifically, the distal side (DS) of cam profile (1630) is oriented upwardly toward the top of the present figures, while the proximal side (PS) of cam profile (1630) is oriented downwardly toward the bottom of the present figures.

Although articulation barrel (1610) of the present example is shown as including a single cam profile (1630), it should be understood that in some examples articulation barrel (1610) may include multiple cam profiles (1630) to provide a cam profile (1630) for each follower pin (332, 334). In some such examples, articulation barrel (1610) may include two cam profiles (1630) on opposite sides of articulation barrel (1610) similar to the configuration of articulation barrel (326) and cam profiles (328, 330) discussed above. In other such examples, articulation barrel (1610) may include two cam profiles (1630) staggered along the length of articulation barrel (1610). Of course, various other suitable configurations of multiple cam profiles (1630) will be readily apparent to those of ordinary skill in the art in view of the teachings herein.

Articulation zone (1660) of cam profile (1630) extends from a first end (1632) to a second end (1650). The profile of cam profile (1630) with respect to articulation zone (1660) is similar to that of the profile with respect to cam profiles (328, 330) described above. For instance, articulation zone (1660) may include a generally helical profile suitable for driving one or more of follower pins (332, 334) for articulation of end effector (214).

As noted above, although not shown, articulation barrel (1610) may include another cam profile identical to cam profile (1630) of the present example, but oriented at an opposite angle relative to cam profile (1630). This configuration may be desirable for pull-pull operation of articulation barrel (1610) where one cam profile (1630) may be used for articulation to one side, while the other cam profile (1630) may be used for articulation to another side. As a result of this pull-pull operation, the particular follower pin (332, 334) associated with a given cam profile (1630) will only engage an articulation surface (1640) associated with first zone (1660). As will be described in greater detail below, this feature may be beneficial to prevent inadvertent engagement of one or more of follower pins (332, 334) with lock zone (1662).

The particular shape of cam profile (1630) within articulation zone (1660) is of a relatively continuous slope. Although a specific slope is shown, it should be understood that various slopes may be used. Alternatively, in other examples, cam profile (1630) within articulation zone (1660) may have a variable slope similar to cam profile (530) of closure barrel (510) described above. For instance, cam profile (1630) within articulation zone (1660) may have an exponential shape, sinusoidal shape or an otherwise linearly increasing slope. Such a shape of cam profile (1630)

may be desirable in some examples to linearize the mechanical advantage of articulation of end effector (214) from one point of articulation (e.g., centered) to another (e.g., fully articulated).

Lock zone (1662) extends from articulation zone (1660) toward a third end (1652) of cam profile (1630). The extension of lock zone (1662) is generally at a zero slope. In other words, lock zone (1662) extends along a path perpendicular to the axis of rotation of articulation barrel (1610). This zero slope is generally configured to hold one or more of follower pins (332, 334) in a specific articulation position while having to apply limited torque to articulation barrel (1610).

The particular articulation position associated with lock zone (1662) is a function of the position of lock zone (1662) along articulation zone (1660). For instance, in the present example lock zone (1662) extends generally from the center of articulation zone (1660) this central extension corresponds to an articulation center of end effector (214). In other words, lock zone (1662) of the present example is configured to lock articulation of end effector (214) in a centered position aligned with longitudinal axis (222) (see FIG. 7). However, it should be understood that in other examples various alternative articulation positions may be associated with lock zone (1662) by adjusting the extension of lock zone (1662) relative to articulation zone (1660).

In an exemplary use, one or more of follower pins (332, 334) may initially engage articulation zone (1660) of cam profile (1630). In this configuration, end effector (214) may be articulated as similarly described above with respect to cam profiles (328, 330). For instance, articulation barrel (1610) may be rotated in one direction to pull a corresponding follower pin (332, 334) along articulation surface (1640) of articulation zone (1660) to articulate end effector (214) in a first direction. Articulation barrel (1610) may then be rotated in an opposite direction to drive another corresponding follower pin (334, 332) along an articulation surface (1640) of another oppositely oriented articulation zone (1660) to actuate end effector (214) in a second direction opposite the first direction.

To lock articulation, articulation barrel (1610) may be rotated to drive one or more of follower pins (332, 334) into lock zone (1662). In practice, this movement may occur during removal or auto-centering of instrument. Regardless, once one or more of follower pins (332, 334) are disposed within lock zone (1662), the zero slope of lock zone (1662) may resist or lock end effector (214) from articulation. As noted above, this may be desirable to provide a lock for articulation of end effector (214) without having to continuously apply torque to articulation barrel (1610). In practice, the articulation lock associated with lock zone (1662) may be used during certain manual or off-robot uses performed by a clinician or other professional to prevent inadvertent articulation of end effector (214).

Once any manual or off-robot uses are performed it may be desirable to unlock articulation of end effector (214). Articulation may subsequently be unlocked by rotating articulation barrel (1610) to move one or more of follower pins (332, 334) from lock zone (1662) back to articulation zone (1660). In practice, this movement may occur during homing or initialization of instrument (210) via robotic system (28).

Figure 47:
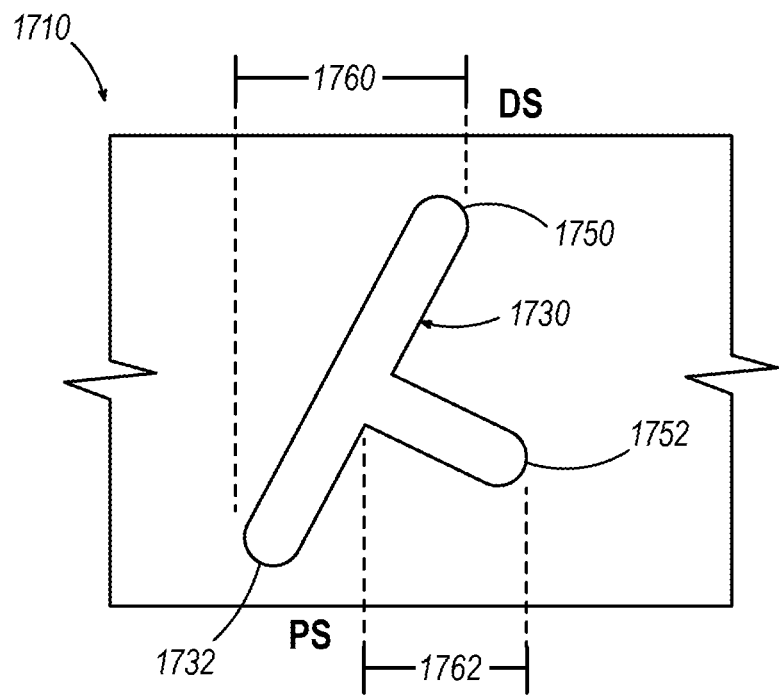
FIG. 47 depicts a schematic view of another exemplary alternative barrel cam for use with the articulation activating mechanism of FIG. 9.

FIG. 47 shows an exemplary alternative articulation barrel (1710) that is substantially similar to articulation barrel (1610) described above. For instance, like with articulation barrel (1610) described above, articulation barrel (1710) of the present example includes a cam profile (1730) having an articulation zone (1760) and a lock zone (1762). Articulation zone (1760) is substantially similar to articulation zone (1660) described above. For instance, as with articulation zone (1660), articulation zone (1760) of the present example extends from a first end (1732) to a second end (1750) and is configured for use cooperatively with another opposite articulation zone (1760) to drive articulation of instrument (210).

Lock zone (1762) is likewise substantially similar to lock zone (1662) described above. For instance, like with lock zone (1662), lock zone (1762) of the present example extends from articulation zone (1760) to a third end (1752) and is generally configured to lock articulation of end effector (214) without continuous torque being applied to articulation barrel (1710). However, unlike lock zone (1662) described above, lock zone (1762) of the present example defines a sloped profile. The sloped profile of lock zone (1762) generally slopes proximally to provide a tensioning feature. In use, lock zone (1762) may be used to both lock articulation and to increase tension in instrument (210). In practice, such a tensioning feature may be desirable to reduce or eliminate backlash in wrist (216).

Figure 48:
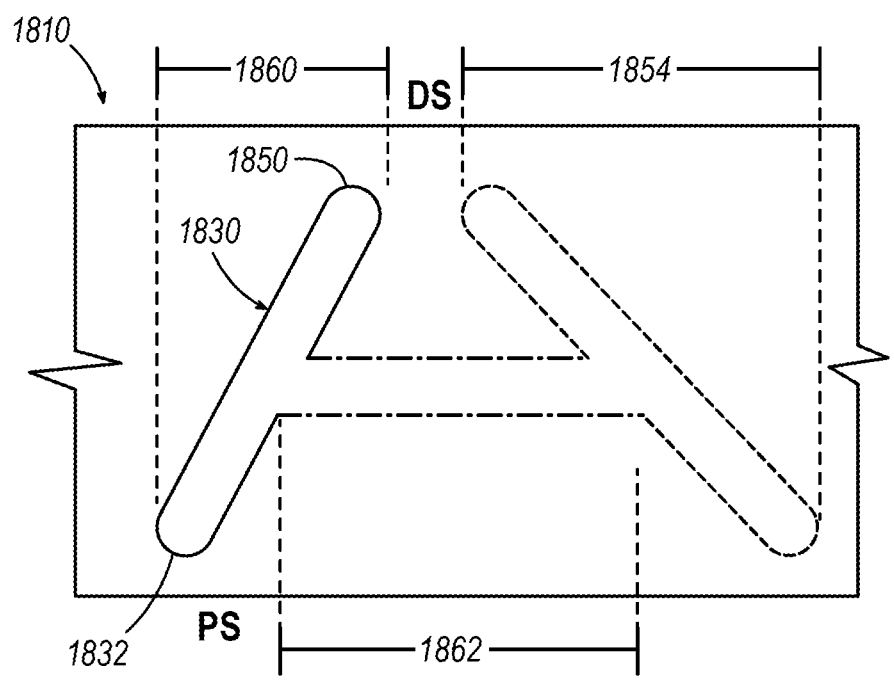
FIG. 48 depicts a schematic view of yet another exemplary alternative barrel cam for use with the articulation activating mechanism of FIG. 9.

FIG. 48 shows another exemplary alternative articulation barrel (1810) that is substantially similar to articulation barrel (1610) described above. For instance, like with articulation barrel (1610) described above, articulation barrel (1810) of the present example includes a cam profile (1830) having an articulation zone (1860) and a lock zone (1862). Articulation zone (1860) is substantially similar to articulation zone (1660) described above. For instance, as with articulation zone (1660), articulation zone (1860) of the present example extends between a first end (1832) and a second end (1850) and is configured for use cooperatively with another opposite articulation zone (1860) to drive articulation of instrument (214). Lock zone (1862) is likewise substantially similar to lock zone (1662) described above. For instance, like with lock zone (1662), lock zone (1862) of the present example extends from articulation zone (1860) and is generally configured to lock articulation of end effector (214) without continuous torque being applied to articulation barrel (1710).

Unlike articulation barrel (1610) described above, articulation barrel (1810) of the present example includes two articulation zones (1860, 1864) on opposite sides of lock zone (1862). Specifically, cam profile (1830) of the present example defines a high speed articulation zone (1860) and a low speed articulation zone (1864). High speed articulation zone (1860) is configured with a relatively high slope. This relatively high slope is configured to provide relatively fast articulation speeds with relatively low mechanical advantage or articulation power. Meanwhile, low speed articulation zone (1864) defines a relatively low slope. This relatively low slope is configured to provide relatively slow articulation speeds with relatively high mechanical advantage or articulation power. This particular configuration of articulation zones (1860, 1864) may be desirable to provide selective control over articulation speed and/or mechanical advantage for particular applications of instrument (210).

The slope for each articulation zone (1860, 1864) is also oriented in a opposite direction relative to the other articulation zone (1864, 1860). This configuration may be beneficial during the pull-pull operation described above. As noted above, pull-pull operation may be used where one articulation zone (1860, 1864) is used in cooperation with another opposite articulation zone (1860, 1864) to pull each follower pin (332, 334) with a separate articulation zone (1860, 1864). Due to the presence of two articulation zones (1860, 1864) in a single cam profile (1830), one or more of follower pins (332, 334) might inadvertently engage lock zone (1862) when, for example, pulling one or more follower pins (332, 334) with low speed articulation zone (1864) (if oriented in the same direction as high speed articulation zone (1860)). To avoid this possibility, the slope for each articulation zone (1860, 1864) is oriented in an opposite direction, so that the pulling force is maintained out the outer edge of each articulation zone (1860, 1864).

Figure 49:
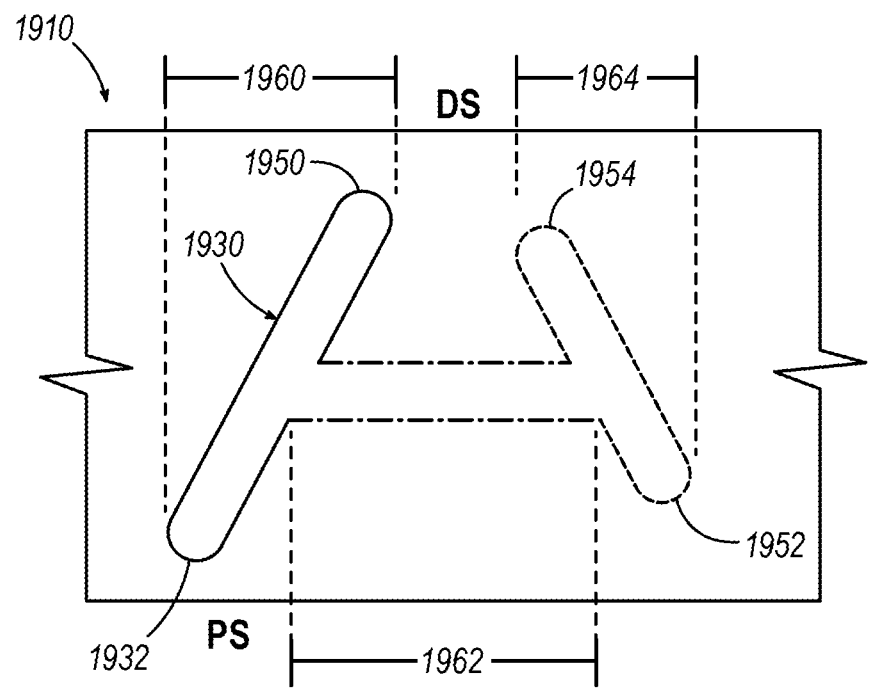
FIG. 49 depicts a schematic view of still another exemplary alternative barrel cam for use with the articulation activating mechanism of FIG. 9.

FIG. 49 shows another exemplary alternative articulation barrel (1910) that is substantially similar to articulation barrel (1610) described above. For instance, like with articulation barrel (1610) described above, articulation barrel (1910) of the present example includes a cam profile (1930) having an articulation zone (1960) and a lock zone (1962). Articulation zone (1960) is substantially similar to articulation zone (1660) described above. For instance, as with articulation zone (1660), articulation zone (1960) of the present example extends between a first end (1932) and a second end (1950) and is configured for use cooperatively with another opposite articulation zone (1960) to drive articulation of instrument (214). Lock zone (1962) is likewise substantially similar to lock zone (1662) described above. For instance, like with lock zone (1662), lock zone (1962) of the present example extends from articulation zone (1960) and is generally configured to lock articulation of end effector (214) without continuous torque being applied to articulation barrel (1910).

Unlike articulation barrel (1610) described above, articulation barrel (1910) of the present example includes two articulation zones (1960, 1964) on opposite sides of lock zone (1962). Specifically, cam profile (1930) of the present example defines a full articulation zone (1960) and a partial articulation zone (1964). Full articulation zone (1960) is configured to operate substantially similarly to articulation zone (1660) described above with articulation of end effector (214) through a full range of motion. However, partial articulation zone (1964) between a third end (1952) and a fourth end (1954). Ends (1952, 1954) are separated by a shorter distance relative to ends (1932, 1950) associated with fill articulation zone (1960). Thus, ends (1952, 1954) provide a hard stop for one or more of follower pins (332, 334) that prevents articulation of end effector (214) through a full range of motion. This particular configuration of articulation zones (1960, 1964) may be desirable to provide selective control over articulation range of motion for particular applications of instrument (210).

The slope for each articulation zone (1960, 1964) is also oriented in a opposite direction relative to the other articulation zone (1964, 1960). This configuration may be beneficial during the pull-pull operation described above. As noted above, pull-pull operation may be used where one articulation zone (1960, 1964) is used in cooperation with another opposite articulation zone (1960, 19864) to pull each follower pin (332, 334) with a separate articulation zone (1960, 1964). Due to the presence of two articulation zones (1960, 1964) in a single cam profile (1930), one or more of follower pins (332, 334) might inadvertently engage lock zone (1962) when, for example, pulling one or more follower pins (332, 334) with partial articulation zone (1964) (if oriented in the same direction as full articulation zone (1960)). To avoid this possibility, the slope for each articulation zone (1960, 1964) is oriented in an opposite direction, so that the pulling force is maintained out the outer edge of each articulation zone (1960, 1964).

B. Articulation Barrel Assembly with Lockout Barrel

Figure 50:
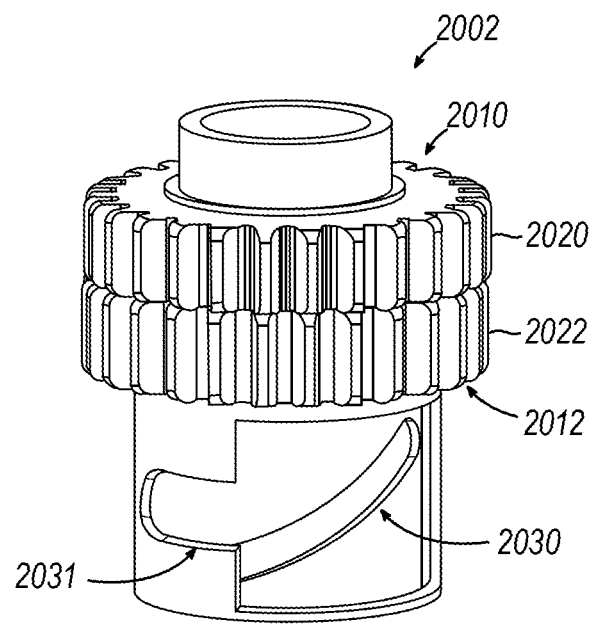
FIG. 50 depicts a perspective view of an exemplary alternative barrel cam assembly for use with the articulation activating mechanism of FIG. 9.

FIG. 50 shows a dual articulation barrel assembly (2002) that may be readily incorporated into instrument (210) in addition to or in lieu of articulation barrel (326). Articulation barrel assembly (2002) of the present example includes an inner articulation barrel (2010) and an outer articulation barrel (2012), with inner articulation barrel (2010) nested coaxially within outer articulation barrel (2012). Articulation barrels (2010, 2012) of the present example are generally substantially similar to articulation barrel (326) described above in that articulation barrels (2010, 2012) include a driven gear (2020, 2022) configured to mesh with drive gear (322) (see FIG. 11) or other similar structures to drive rotation of each articulation barrel (2010, 2012). However, due to the presence of two driven gears (2020, 2022), it should be understood that in some examples of instrument (210), multiple drive gears (322) may be incorporated into instrument (210) to correspond to each driven gear (2020, 2022).

Also as with articulation barrel (326) described above, articulation barrels (2010, 2012) of the present example each include a cam profile (2030, 2031) configured to receive one or both of follower pins (332, 334) to drive articulation of end effector (214) or other similar structures of instrument (210) via rotation of articulation barrels (2010, 2012). Use of two articulation barrels (2010, 2012) in the present example may be desirable in some circumstances to provide a lockout feature for articulation of end effector (214).

Although articulation barrels (2010, 2012) and various components thereof are characterized herein using the terms "inner" and "outer," it should be understood that such terms are used only by way of example to describe the present configuration. As such, in other examples, articulation barrels (2010, 2012) or various features of each articulation barrel (2010, 2012) may be reversed with outer features being moved to an inner position and inner features being moved to an outer position. In other examples, the inner and outer characterization may be omitted entirely, with each articulation barrel (2010, 2012) being positioned on a separate axis.

Figure 51:
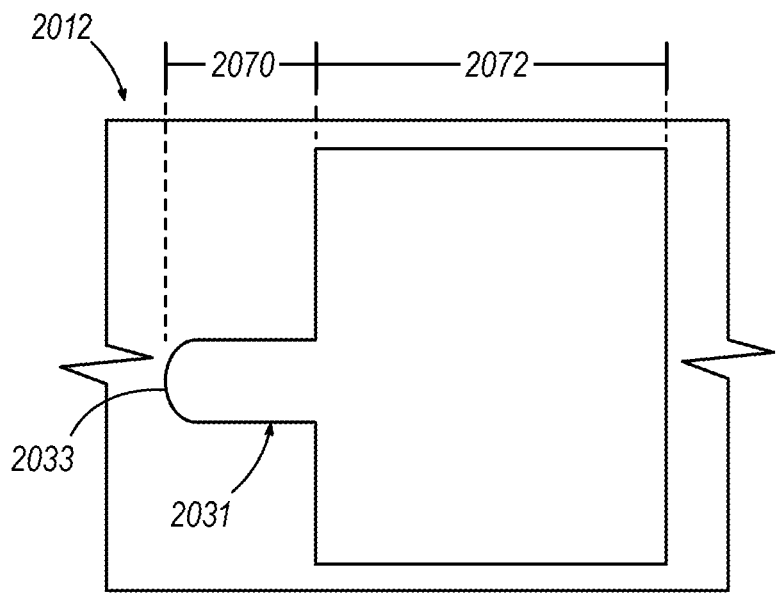
FIG. 51 depicts a schematic view of an outer articulation barrel of the barrel cam assembly of FIG. 50.

As noted above, each articulation barrel (2010, 2012) includes a respective cam profile (2030, 2031). As will be described in greater detail below, cam profiles (2030, 2031) are generally configured to operate cooperatively to drive movement of one or more of follower pins (332, 334) through two separate actuation sequences. In the present example, outer articulation barrel (2012) includes an outer cam profile (2031). As best seen in FIG. 51, outer cam profile (2031) of the present example is generally configured to provide a selective locking feature to selectively lock articulation of end effector (214) in a predetermined articulation configuration.

Outer cam profile (2031) of the present example includes a lock zone (2070) and a free travel zone (2072). Lock zone (2070) extends from a first end (2033) toward free travel zone (2072). The extension of lock zone (2070) is generally perpendicular to the axis of rotation of outer articulation barrel (2012). This perpendicular extension generally defines a zero slope. As will be described in greater detail below, such a zero slope permits lock zone (2070) to act as an articulation lock without requiring substantial torque to be applied to outer articulation barrel (2012).

Free travel zone (2072) extends from lock zone (2070) both laterally and longitudinally. Free travel zone (2072) is generally configured to provide free movement of one or more of follower pins (332, 334) within free travel zone (2072). As such, free travel zone (2072) defines a large open area with a height and width multiple times the diameter of each follower pin (332, 334). As will be described in greater detail below, this height and width may be configured to permit complete travel of one or more of follower pins (332, 334) through a complete articulation sequence when one or more of follower pins are driven by inner articulation barrel (2010).

Figure 52:
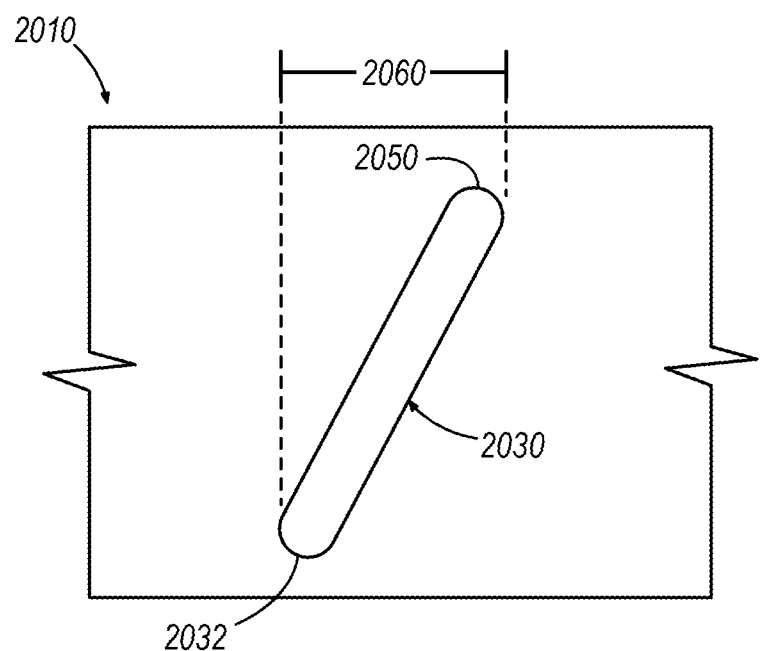
FIG. 52 depicts a schematic view of an inner articulation barrel of the barrel cam assembly of FIG. 50.

FIG. 52 shows inner cam profile (2030) in greater detail below. As can be seen, inner cam profile (2030) defines an articulation zone (2060) extending from a first end (2032) to a second end (2050). Inner cam profile (2030) is configured substantially similarly to cam profiles (328, 330) described above in that inner cam profile (2030) is configured to drive one or more of follower pins (332, 334) through an articulation sequence to drive articulation of end effector (214).

Although articulation barrels (2010, 2012) of the present example are shown as including a single cam profile (2030, 2031) per articulation barrel (2010, 2012), it should be understood that in practice each articulation barrel (2010, 2012) may include another opposite cam profile (2030, 2031) on an opposite side of each articulation barrel (2010, 2012). As noted above, this configuration may be desirable to provide a cam profile (2030, 2031) for each follower pin (332, 334) to drive follower pins (332, 334) through an articulation sequence.

In an exemplary use of articulation barrel assembly (2002), inner articulation barrel (2010) may be used to primarily drive articulation of end effector (214) by manipulating one or more of follower pins (332, 334). For instance, as noted above, inner articulation barrel (2010) may include inner cam profile (2030) as shown and another opposite inner cam profile (2030) on an opposite side of inner articulation barrel (2010). One inner cam profile (2030) may then be used to pull a given follower pin (332, 334) to drive articulation of end effector (214) in a first direction. Subsequently, the other inner cam profile (2030) may then be used to pull a given follower pin (334, 332) to drive articulation of end effector (214) in a second direction opposite the first direction.

During articulation of end effector (214) via inner articulation barrel (2010), outer articulation barrel (2012) may be positioned to align free travel zone (2072) with inner cam profile (2030). This alignment may permit full travel of each follower pin (332, 334) when driven by inner cam profile (2030). Although not shown, it should be understood that in the dual inner cam profile (2030) configuration described above, outer articulation barrel (2012) may likewise include another opposite outer cam profile (2031) on an opposite side of outer articulation barrel (2012).

During articulation of end effector (214), it may be desirable to lock end effector (214) in a predetermined articulation lock position. For instance, in some uses instrument (210) may be operated manually by a clinician or other professional. In such uses, it may be beneficial to lock articulation of end effector (214) to simplify such manual operations. To lock articulation in the present example, inner articulation barrel (2010) may be used to drive end effector (214) to the predetermined articulation lock position. The predetermined articulation lock position is generally determined by the position of lock zone (2070) of outer articulation barrel (2012) relative to articulation zone (2060) of inner articulation barrel (2010). For instance, in the present example, lock zone (2070) is positioned in the center of articulation zone (2060). Thus, the predetermined articulation lock position generally corresponds to an articulation center where end effector (214) is aligned with longitudinal axis (222). However, it should be understood that in other examples various other suitable predetermined articulation lock positions may be used.

Once end effector (214) is driven to the predetermined articulation lock position via inner articulation barrel (2010), outer articulation barrel (2012) may be rotated to engage lock zone (2070) with one or more of follower pins (332, 334). Once lock zone (2070) is engaged with one or more of follower pins (332, 334), the zero slope of lock zone (2070) may prevent proximal-distal movement of follower pins (332, 334), thereby locking articulation of end effector (214). Also due to the zero slope of lock zone (2070), this locking configuration may be maintained without having to apply torque to outer articulation barrel (2012). Thus, the present use may be desirable to avoid excess heat due to excessive motor operation, and/or to avoid excess wear.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: a drive housing having a first and second end; at least one spline extending between the first and second ends and including a drive gear, wherein the drive gear is configured to rotate with rotation of the at least one spline; a carriage movable relative to the at least one spline; an elongate shaft assembly extending from the carriage and through the first end; an end effector disposed at a distal end of the elongate shaft assembly; and an activating mechanism housed in the carriage, wherein the activating mechanism includes a barrel cam extending along a rotational axis and having a first cam profile radially extending about the rotational axis, wherein the barrel cam is operatively coupled to the drive gear such that rotation of the drive gear is configured to actuate the activating mechanism to move at least a portion of the end effector, wherein the first cam profile defines a plurality of slopes relative to the rotational axis such that the first cam profile is configured to drive movement of at least a portion of the end effector or the elongate shaft assembly at different rates according to the plurality of slopes.

Example 2

The surgical instrument of Example 1, wherein the first cam profile of the barrel cam defines a first zone and a second zone, wherein the first zone is configured to move the end effector at a high speed and with low force, wherein the second zone is configured to move the end effector at low speed and with high force.

Example 3

The surgical instrument of Example 1, wherein the first cam profile of the barrel cam defines a first zone, a second zone, and a third zone, wherein the first zone is configured to move the end effector at a high speed and with low force, wherein the second zone is configured to move the end effector at moderate speed and with moderate force, wherein the third zone is configured to move the end effector at low speed and with high force.

Example 4

The surgical instrument of Example 3, wherein the first cam profile defines an exponential shape, wherein the exponential shape defines the first zone, the second zone, and the third zone.

Example 5

The surgical instrument of Examples 3 or 4, wherein the end effector includes a first jaw and a second jaw, wherein the first cam profile is configured to drive movement of the first jaw of the end effector relative to the second jaw of the end effector, wherein movement of the first jaw from a fully open configuration towards a partially open configuration corresponds to movement via the first zone, wherein movement of the first jaw from the partially open configuration to a partially closed configuration corresponds to movement via the second zone, wherein movement of the first jaw from the partially closed configuration to a fully closed configuration corresponds to movement via the third zone.

Example 6

The surgical instrument of any one or more of Examples 1 through 5, wherein the first cam profile of the barrel cam defines a first operational section and a second operational section, wherein the first operational section is configured for use with low power input via the spline, wherein the second operational section is configured for use with high power input via the spline.

Example 7

The surgical instrument of Example 6, wherein the first operational section includes at least one zone including a relatively low slope, the relatively low slope being configured to drive movement of the end effector with relatively low power input via the spline.

Example 8

The surgical instrument of Examples 6 or 7, wherein the second operational section includes at least one zone including a relatively high slope, the relatively high slope being configured to drive movement of the end effector with relatively high power input via the spline.

Example 9

The surgical instrument of Example 6, wherein the first operational section includes at least one zone defining a first slope, wherein the second operational section includes at least one zone defining a second slope, wherein the second slope is greater than the first slope.

Example 10

The surgical instrument of any one or more of Examples 6 through 9, wherein the first cam profile of the barrel cam further defines a functional wall, wherein the functional wall is disposed between the first operational section and the second operational section.

Example 11

The surgical instrument of Example 10, wherein the functional wall defines a wall slope, wherein the wall slope is configured to be perceived by a clinician when the barrel cam is driven by the clinician via the spline.

Example 12

The surgical instrument of Example 10, wherein the wall slope is greater than one or more slopes of the plurality of slopes.

Example 13

The surgical instrument of any one or more of Examples 1 through 12, wherein the activating mechanism further includes a second cam profile, a first follower pin and a second follower pin, wherein the first follower pin is configured to engage the first cam profile, wherein the second follower pin is configured to engage the second cam profile.

Example 14

The surgical instrument of Example 13, wherein the first cam profile and the second cam profile define substantially similar shapes.

Example 15

The surgical instrument of any one or more of Examples 1 through 14, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, and any combination thereof.

Example 16

A surgical instrument, comprising: a drive housing having a first and second end; at least one spline extending between the first and second ends and including a drive gear, wherein the drive gear is configured to rotate with rotation of the at least one spline; a carriage movably mounted to the at least one spline; an elongate shaft assembly extending from the carriage and through the first end; an end effector disposed at a distal end of the elongate shaft assembly, wherein the end effector includes a first jaw and a second jaw; and a jaw activating mechanism housed in the carriage, wherein the jaw activating mechanism includes a closure barrel and a first follower pin, wherein the closure barrel extends along a rotational axis and defines a first cam profile radially extending about the rotational axis, wherein the first cam profile is configured to engage the first follower pin, wherein the drive gear is configured to rotate the closure barrel to drive movement of the first follower pin via the first cam profile, wherein the first follower pin is in communication with the end effector to drive movement of the first jaw of the end effector relative to the second jaw of the end effector, wherein the first cam profile defines a plurality of slopes relative to the rotational axis such that the first cam profile is configured to drive movement of the first jaw of the end effector relative to the second jaw of the end effector at different rates along a length of the first cam profile according to the plurality of slopes.

Example 17

The surgical instrument of Example 16, wherein the first cam profile defines a first operational section and a second operational section, wherein the first operational section and the second operational section extend in opposite directions from a central zone defined by the first cam profile.

Example 18

The surgical instrument of Example 17, wherein the first operational section of the first cam profile defines a first zone having a first slope, wherein the second operational section defines a second zone having a second slope and a third zone having a third slope, wherein the second slope is greater than the third slope, wherein the second slope is further greater than the first slope.

Example 19

The surgical instrument of Example 18, wherein the first cam profile further defines a functional well, wherein the functional well defines a fourth slope, wherein the fourth slope is greater than the second slope.

Example 20

A method of moving an end effector of a surgical instrument, comprising: locating the surgical instrument adjacent to a patient, the surgical instrument including: a drive housing having a first end and a second end, at least one spline extending between the first end and the second end and including a drive gear configured to rotate in response to rotation of the at least one spline, a carriage movably mounted to the at least one spline, an elongate shaft assembly extending from the carriage, wherein a portion of the elongate shaft assembly extends through the first end of the drive housing, the end effector disposed at a distal end of the elongate shaft assembly, and an activating mechanism associated with the carriage, wherein the activating mechanism includes a barrel cam configured to drive motion of at least a portion of the end effector in response to rotation of the drive gear; moving the end effector to an at least partially open position by rotating the barrel cam in a first direction; applying a disposable component to the end effector; and using the end effector to grasp tissue by rotating the barrel cam in a second direction, the second direction being opposite of the first direction.

Example 21

The method of Example 20, wherein the step of applying a disposable component to the end effector includes applying a staple cartridge to the end effector.

Example 22

The method of Examples 20 or 21, wherein the step of applying a disposable component to the end effector includes applying a buttress or other adjunct material to the end effector.

Example 23

The method of any one or more of Examples 20 through 22, wherein rotation of the barrel cam in the first direction is performed using a manual rotation input.

Example 24

The method of any one or more of Examples 20 through 23, wherein the step of using the end effector to grasp tissue is performed using a motor.

Example 25

The method of any one or more of Examples 20 through 24, further comprising using the end effector to compress tissue.

Example 26

The method of Example 25, wherein the step of using the end effector to grasp tissue includes applying a first power output to the end effector via the barrel cam, wherein the step of using the end effector to compress tissue includes applying a second power output to the end effector via the barrel cam.

Example 27

The method of Example 26, wherein the first power output is less than the second power output.

Example 28

The method of Examples 25 or 26, wherein the step of using the end effector to grasp tissue includes actuating the end effector at a first speed via the barrel cam, wherein the step of using the end effector to compress tissue includes actuating the end effector at a second speed via the barrel cam.

Example 29

The method of Example 28, wherein the first speed is greater than the second speed.

Example 30

The method of any one or more of Examples 26 through 29, wherein the steps of using the end effector to grasp tissue and using the end effector to compress tissue are both performed by rotating the barrel cam at a single speed.

Example 31

A carriage assembly for use with a surgical instrument, comprising: a carriage movably mounted to a spline; an elongate shaft extending from the carriage; and an activating mechanism housed in the carriage, wherein the activating mechanism includes a barrel cam having a first cam profile, wherein the barrel cam is operatively coupled to the drive gear such that rotation of the drive gear is configured to actuate the activating mechanism to move at least a portion of an end effector, wherein the first cam profile defines a plurality of slopes such that the first cam profile is configured to drive movement of the end effector at different rates at different points of movement of the end effector.

Example 32

The carriage assembly of Example 31, wherein the first cam profile of the barrel cam defines a first zone and a second zone, wherein the first zone is configured to move the end effector at a high speed and with low force, wherein the second zone is configured to move the end effector at low speed and with high force.

Example 33

The carriage assembly of Example 31, wherein the first cam profile of the barrel cam defines a first zone, a second zone, and a third zone, wherein the first zone is configured to move the end effector at a high speed and with low force, wherein the second zone is configured to move the end effector at moderate speed and with moderate force, wherein the third zone is configured to move the end effector at low speed and with high force.

Example 34

The carriage assembly of Example 33, wherein the first cam profile defines an exponential shape, wherein the exponential shape defines the first zone, the second zone, and the third zone.

Example 35

The carriage assembly of Examples 33 or 34, wherein the first cam profile is configured to drive movement of a first jaw of the end effector relative to a second jaw of the end effector, wherein movement via the first zone corresponds to movement of the first jaw from a fully open configuration towards a partially open configuration, wherein movement via the second zone corresponds to movement of the first jaw from the partially open configuration to a partially closed configuration, wherein movement via the third zone corresponds to movement of the first jaw from the partially closed configuration to a fully closed configuration.

Example 36

The carriage assembly of any one or more of Examples 31 through 35, wherein the first cam profile of the barrel cam defines a first operational section and a second operational section, wherein the first operational section is configured for use with low power input via the spline, wherein the second operational section is configured for use with high power input via the spline.

Example 37

The carriage assembly of Example 36, wherein the first operational section includes at least one zone including a relatively low slope, the relatively low slope being configured to drive movement of the end effector with relatively low power input via the spline.

Example 38

The carriage assembly of Examples 6 or 7, wherein the second operational section includes at least one zone including a relatively high slope, the relatively high slope being configured to drive movement of the end effector with relatively high power input via the spline.

Example 39

The carriage assembly of Example 6, wherein the first operational section includes at least one zone defining a first slope, wherein the second operational section includes at least one zone defining a second slope, wherein the second slope is greater than the first slope.

Example 40

The carriage assembly of any one or more of Examples 36 through 39, wherein the first cam profile of the barrel cam further defines a functional wall, wherein the functional wall is disposed between the first operational section and the second operational section.

Example 41

The carriage assembly of Example 40, wherein the functional wall defines a wall slope, wherein the wall slope is configured to be perceived by a clinician when the barrel cam is driven by the clinician via the spline.

Example 42

The carriage assembly of Example 10, wherein the wall slope is greater than one or more slopes of the plurality of slopes.

Example 43

The carriage assembly of any one or more of Examples 31 through 42, wherein the activating mechanism further includes a second cam profile, a first follower pin and a second follower pin, wherein the first follower pin is configured to engage the first cam profile, wherein the second follower pin is configured to engage the second cam profile.

Example 44

The carriage assembly of Example 13, wherein the first cam profile and the second cam profile define substantially similar shapes.

VI. Miscellaneous

Any one or more of the teaching, expressions, embodiments, examples, etc. described herein may be combined with any one or more of the teachings, expressions, embodiments, examples, etc. described in U.S. Pat. App. No. 17/245,340, entitled "Robotic Surgical System with an Articulation Lockout," filed on Apr. 30, 2021, published as U.S. Pub. No. 2022/0346891 on Nov. 3, 2022; U.S. Pat. App. No. 17/245,351, entitled "Multi-Zone Jaw Closure of a Robotic Surgical System," filed on Apr. 30, 2021, published as U.S. Pub. No. 2022/0346898 on Nov. 3, 2022; U.S. Pat. App. No. 17/245,111, entitled "Selectable Jaw Closure of a Robotic Surgical System," filed on Apr. 30, 2021, published as U.S. Pub. No. 2022/0346890 on Nov. 3, 2022; and/or U.S. Pat. App. No. 17,245,100, entitled "Translatable Barrel Cam of a Robotic Surgical System," filed on Apr. 30, 2021, issued as U.S. Pat. No. 11,607,218 on Mar. 21, 2023. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a drive housing having a first and second end;
   (b) at least one spline extending between the first and second ends and including a drive gear, wherein the drive gear is configured to rotate with rotation of the at least one spline;
   (c) a carriage movable relative to the at least one spline;
   (d) an elongate shaft assembly extending from the carriage and through the first end;
   (e) an end effector disposed at a distal end of the elongate shaft assembly; and
   (f) an activating mechanism housed in the carriage, wherein the activating mechanism includes a barrel cam extending along a rotational axis and having a first cam profile radially extending about the rotational axis, wherein the barrel cam is operatively coupled to the drive gear such that rotation of the drive gear is configured to actuate the activating mechanism to move at least a portion of the end effector, wherein the first cam profile defines a plurality of slopes relative to the rotational axis such that the first cam profile is configured to drive movement of at least a first portion of the end effector or the elongate shaft assembly at different rates according to the plurality of slopes, wherein the first cam profile of the barrel cam defines a first zone and a second zone, wherein the first zone is configured to move the end effector at a high speed and with a low force, and wherein the second zone is configured to move the end effector at a lower speed than the high speed and with a higher force than the low force.

2. The surgical instrument of claim 1, wherein the first cam profile of the barrel cam defines the first zone, the second zone, and a third zone, wherein the first zone is configured to move the end effector at the high speed and with the low force, wherein the second zone is configured to move the end effector at a moderate speed and with a moderate force, wherein the third zone is configured to move the end effector at a low speed and with a high force.

3. The surgical instrument of claim 2, wherein the first cam profile defines an exponential shape, wherein the exponential shape defines the first zone, the second zone, and the third zone.

4. The surgical instrument of claim 2, wherein the end effector includes a first jaw and a second jaw, wherein the first cam profile is configured to drive movement of the first jaw of the end effector relative to the second jaw of the end effector, wherein movement of the first jaw from a fully open configuration towards a partially open configuration corresponds to movement via the first zone, wherein movement of the first jaw from the partially open configuration to a partially closed configuration corresponds to movement via the second zone, wherein movement of the first jaw from the partially closed configuration to a fully closed configuration corresponds to movement via the third zone.

5. The surgical instrument of claim 1, wherein the first cam profile of the barrel cam defines a first operational section and a second operational section, wherein the first operational section is configured for use with low power input via the spline, wherein the second operational section is configured for use with high power input via the spline.

6. The surgical instrument of claim 5, wherein the first operational section includes at least one zone including a relatively low slope, the relatively low slope being configured to drive movement of the end effector with relatively low power input via the spline.

7. The surgical instrument of claim 5, wherein the second operational section includes at least one zone including a relatively high slope, the relatively high slope being configured to drive movement of the end effector with relatively high power input via the spline.

8. The surgical instrument of claim 5, wherein the first operational section includes at least one zone defining a first slope, wherein the second operational section includes at least one zone defining a second slope, wherein the second slope is greater than the first slope.

9. The surgical instrument of claim 5, wherein the first cam profile of the barrel cam further defines a functional wall, wherein the functional wall is disposed between the first operational section and the second operational section.

10. The surgical instrument of claim 9, wherein the functional wall defines a wall slope, wherein the wall slope is configured to be perceived by a clinician when the barrel cam is driven by the clinician via the spline.

11. The surgical instrument of claim 9, wherein the wall slope is greater than one or more slopes of the plurality of slopes.

12. The surgical instrument of claim 1, wherein the activating mechanism further includes a second cam profile, a first follower pin and a second follower pin, wherein the first follower pin is configured to engage the first cam profile, wherein the second follower pin is configured to engage the second cam profile.

13. The surgical instrument of claim 12, wherein the first cam profile and the second cam profile define substantially similar shapes.

14. The surgical instrument of claim 1, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, and any combination thereof.

15. A surgical instrument, comprising:
(a) a drive housing having a first and second end;
(b) at least one spline extending between the first and second ends and including a drive gear, wherein the drive gear is configured to rotate with rotation of the at least one spline;
(c) a carriage movably mounted to the at least one spline;
(d) an elongate shaft assembly extending from the carriage and through the first end;
(e) an end effector disposed at a distal end of the elongate shaft assembly, wherein the end effector includes a first jaw and a second jaw; and
(f) a jaw activating mechanism housed in the carriage, wherein the jaw activating mechanism includes a closure barrel and a first follower pin, wherein the closure barrel extends along a rotational axis and defines a first cam profile radially extending about the rotational axis, wherein the first cam profile is configured to engage the first follower pin, wherein the drive gear is configured to rotate the closure barrel to drive movement of the first follower pin via the first cam profile, wherein the first follower pin is in communication with the end effector to drive movement of the first jaw of the end effector relative to the second jaw of the end effector, wherein the first cam profile defines a plurality of slopes relative to the rotational axis such that the first cam profile is configured to drive movement of the first jaw of the end effector relative to the second jaw of the end effector at different rates along a length of the first cam profile according to the plurality of slopes, wherein the first cam profile defines a first operational section and a second operational section, wherein the first operational section and the second operational section extend in opposite directions from a central zone defined by the first cam profile, and wherein the first operational section of the first cam profile defines a first zone having a first slope, wherein the second operational section defines a second zone having a second slope and a third zone having a third slope, wherein the second slope is greater than the third slope, and wherein the second slope is further greater than the first slope.

16. The surgical instrument of claim 15, wherein the first cam profile further defines a functional well, wherein the functional well defines a fourth slope, wherein the fourth slope is greater than the second slope.

17. A surgical instrument, comprising:
(a) a drive housing having a first and second end;
(b) at least one spline extending between the first and second ends and including a drive gear, wherein the drive gear is configured to rotate with rotation of the at least one spline;
(c) a carriage movable relative to the at least one spline;
(d) an elongate shaft assembly extending from the carriage and through the first end;
(e) an end effector disposed at a distal end of the elongate shaft assembly; and
(f) an activating mechanism housed in the carriage, wherein the activating mechanism includes a barrel cam extending along a rotational axis and having a first cam profile radially extending about the rotational axis, wherein the barrel cam is operatively coupled to the drive gear such that rotation of the drive gear is configured to actuate the activating mechanism to move at least a portion of the end effector, wherein the first cam profile defines a plurality of slopes relative to the rotational axis such that the first cam profile is configured to drive movement of at least a first portion of the end effector or the elongate shaft assembly at different rates according to the plurality of slopes, wherein the first cam profile of the barrel cam defines a first operational section and a second operational section, wherein the first operational section is configured for use with low power input via the spline, and wherein the second operational section is configured for use with high power input via the spline.

18. The surgical instrument of claim 17, wherein the first operational section includes at least one zone including a relatively low slope, the relatively low slope being configured to drive movement of the end effector with relatively low power input via the spline.

19. The surgical instrument of claim 17, wherein the first operational section includes at least one zone defining a first slope, wherein the second operational section includes at least one zone defining a second slope, wherein the second slope is greater than the first slope.

20. The surgical instrument of claim 17, wherein the first cam profile of the barrel cam further defines a functional wall, wherein the functional wall is disposed between the first operational section and the second operational section.

* * * * *